US007524492B2

(12) United States Patent
Sharma

(10) Patent No.: US 7,524,492 B2
(45) Date of Patent: Apr. 28, 2009

(54) INSULIN RELATED TRANSCRIPTION FACTOR AND USES THEREOF

(75) Inventor: Arun Sharma, Cambridge, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 392 days.

(21) Appl. No.: 10/232,563

(22) Filed: Aug. 30, 2002

(65) Prior Publication Data

US 2003/0087394 A1 May 8, 2003

Related U.S. Application Data

(60) Provisional application No. 60/316,453, filed on Aug. 31, 2001.

(51) Int. Cl.
*A61K 48/00* (2006.01)
*C12N 15/00* (2006.01)
*C12N 5/00* (2006.01)
*C12N 5/02* (2006.01)

(52) U.S. Cl. .................. 424/93.21; 435/455; 435/325

(58) Field of Classification Search ................. 435/455
See application file for complete search history.

(56) References Cited

U.S. PATENT DOCUMENTS 6,274,338 B1   8/2001  Glimcher et al.
6,933,125 B2 * 8/2005  Glimcher et al. ........... 435/69.1

OTHER PUBLICATIONS

Anderson et al., Nature, vol. 392, pp. 25-30, 1998.*
Verma, Nature, vol. 389, pp. 239-242, 1997.*
Van Linthout et al. Current Pharmaceutical Design 2005, 11:2927-2940.*
Thomas et al. Nature, 4:346-358, 2003.*
Juengst, BMJ, 2003, 326:1410-11.*
Ngo et al, The Protein Folding Problem and Tertiary Structure Prediction, 1994, Merz et al (ed.), Birkhauser, Boston, MA, pp. 433 and 492-494.*
Ber et al., 2003, J. Biol. Chem, 278: 31950-31957.*
Ferber et al., 2000, Nature Medicine, 6: 568-572.*
Ben-Shushan, "A Pancreatic β-Cell-specific Enhancer . . . ", 2001 J. Biol Chem 276:17533-17540.
Benkelifa et.al, "*mafA*, a novel member of the *maf* . . . ", (1998) Oncogene 17:247-254.
Benkhelifa et al., "Phosphorylation of MafA Is Essential . . .", (2001) Mol. Cell Biol. 21:4441-4452.
Blank, V. & Andrews, N. C., "The Maf transcription factors: . . . ", (1997) *TIBS* 22, 437-441.
Carty et al., "Identification of cis- and trans-Active Factors . . . "(1997) J. Biol. Chem. 272:11986-93.
Crowe et al., "Mutagenesis of the Rat Insulin . . . ", (1989) Mol. Cell. Biol. 9, 1784-1789.
Dandoy-Dron et al., "Regulatory regions of rat insulin . . . ", (1991) Nucleic Acids Res. 19, 4925-4936.

Dignam, J. D., Lebovitz, R. M., & Roeder, R. G., "Accurate transcription initiatiation by RNA . . . ", (1983) *Nucleic Acids Res.* 11, 1475-1489.
Dlakic et.al., "DNA sequence-dependent folding determines . . . ", (2001) EMBO 20:828-840.
Edlund et al., "Cell-Specific Expression of the Rat Insulin . . . " (1985) Science 30, 912-916.
Gannon, "Regulatory Regions Driving Developmental . . . ", 2001. . Dev Biol 238:185-201.
Gerrish, "The role of Hepatic Nuclear Factor 1α . . . ", 2001. J Biol Chem 276 :47775-47784.
Gerrish, et al., "Pancreatic β Cell-specific Transcription . . . ", (2000) J. Biol. Chem. 275:3485-92.
Hanahan, "Heritable formation of pancreatic β-cell . . . ", (1985) Nature 315, 115-122.
Harrington, R. H. & Sharma, A., "Transcription Factors Recognizing Overlapping . . . "(2001) *J.Biol.Chem.* 276, 104-113.
Ho, I., "The Proto-Oncogene c-maf Is Responsible . . . ", (1996) Cell 85, 973-983.
Huang, "Regulation of the Pancreatic Islet-Specific Gene . . . ", 2000. Mol.Cell.Biol. 20:3292-3307.
Jonas, "Chronic Hyperglycemia Triggers Loss . . . " (1999) *J.Biol. Chem.* 274, 14112-14121.
Karlsson et al., "A mutational analysis of the insulin gene transcriptional control . . . ", 1987. . PNAS U S A 84:8819-8823.
Kim et.al., "Requirement for the c-Maf transcription factor . . . ", (1999) PNAS 96:3781-3785.
Manzanares, "Segmental regulation of Hoxb-3 by kreisler", (1997) *Nature* 387, 191-195.
Marshak, "Functional Conservation of Regulatory Elements . . . ", 2000. Mol Cell Biol 20:7583-7590.
Marshak., "Regulatory Elements Involved in Human . . . ", 2001. Diabetes 50 Suppl 1 :S37-38.
Matsushima-Hibiya, "Rat Maf-related factors: The specificities . . . ", (1998) *Biochem.Biophys.Res.Comm.* 245, 412-418.
Ogino and Yasuda, "Induction of Lens Differentiation by Activation . . . ", (1998) Science 280: 115-118.
Ring et.al., "Regulation of mouse lens fiber cell . . . ", (2000) Development 127:307-317.
Robinson et al., "Expression of the trans-Active factors that stimulate insulin . . . ", (1994) *J. Biol. Chem.* 269, 2452-2460.
Samaras, "Conserved Sequences in Tissue-Specific Regulatory Region . . . ", 2002. Mol Cell Biol 22:4702-4713.
Sander et al., "The β cell transcription factors and development of the pancreas", (1997) J. Mol. Med. 75, 327-340.
Sharma et al., "Glucose-Induced Transcription of the insulin gene is mediated . . . ", (1994) Mol. Cell. Biol. 14, 871-879.
Sharma et al., "The role of insulin control element and RIPE3b1 . . . ", (1995) Mol. Endocrinol. 9, 1468-1476.

(Continued)

*Primary Examiner*—Joanne Hama
(74) *Attorney, Agent, or Firm*—Fish & Richardson P.C.

(57) ABSTRACT

The invention provides isolated mMafA polypeptides, nucleic acids, vectors and host cells containing them, which encode a novel insulin related transcription factor. Diagnostic methods, methods of selecting and differentiating insulin-producing cells, and methods of treatment utilizing compositions of the invention are also provided.

49 Claims, 15 Drawing Sheets

OTHER PUBLICATIONS

Sharma, "Pancreatic Islet Expression of the Homeobox Factor . . . ", 1996. J Biol Chem 271:2294-2299.

Sharma, "Hormonal Regulation of an Islet-Specific Enhancer . . . ", 1997. Mol Cell Biol 17:2598-2604.

Shieh et al., "Cell-specific and Ubiquitous Factors Are responsible for the Enhancer . . . ", (1991) J. Biol. Chem. 266, 16708-16714.

Shieh et al., "Molecular characterization of the Rat Insulin Enhancer . . . ", (1995) J. Biol. Chem. 270, 21503-21508.

Sieweke, M. H., Tekotte, H., Frampton, J., & Graf, T., "MafB Is an Interaction Partner and Repressor . . . ", (1996) Cell 85, 49-60.

Silva et al., "Application of a protein-blotting procedure to the study . . . " (1987) Proc.Natl.Acad.Sci.USA 84, 1744-1748.

Stein, "Regulation of Insulin Gege Transcription", (1993) Trends Endocrinol. Metab. 4, 96-100.

Stellrecht et al., "Tissue-specific and Developmental Regulation of the Rat . . . ", (1997) J. Biol. Chem. 272, 3567-3572.

Wang et.al., "Human KRML (MAFB): cDNA Cloning, Genomic . . . ", Genomics 59: 275-281.

Watada, "Transcriptional and Translational Regulation . . . ", 2000. J Biol Chem 275:34224-34230.

Wu et al., "Hepatocyte Nuclear Factor 3β Is involved . . . ", 1997. Mol Cell Biol 17:6002-6013.

Zhao et al., "The RIPE3b1 Activator of the Insulin Gene is composed of a Protein . . . " (2000) J. Biol. Chem. 275, 10532-10537.

GenBank Accession No. AC116393; Mar. 13, 2003.

Olbrot et al., "Identification of beta-cell-specific insulin gene . . . ", May 14, 2002, PNAS, vol. 99(10);6737-6742.

Couzin, "Islet transplants face test of time," Science, 306(5693):34-37 (2004).

Harmon et al., "Oxidative Stress-mediated, Post-translational Loss of MafA Protein as a Contributing Mechanism to Loss of Insulin Gene Expression in Glucotoxic Beta Cells," J. Biol. Chem., 280(12):11107-11113, (2005).

Kaneto et al., "A Crucial Role of MafA as a Novel Therapeutic Target for Diabetes," J. Biol. Chem., 280(15):15047-15052, (2005).

Kataoka et al., "MafA Is a Glucose-regulated and Pancreatic β-Cell-specific Transcriptional Activator for the Insulin Gene," J. Biol. Chem., 277(51):49903-49910, (2002).

Matsuoka et al., "Members of the Large Maf Transcription Family Regulate Insulin Gene Transcription in Islet β Cells," Mol. Cell. Biol., 23(17):6049-6062, (2003).

Matsuoka et al., "The MafA transcription factor appears to be responsible for tissue-specific expression of insulin," Proc. Natl. Acad. Sci. U.S.A., 101(9):2930-2933, (2004).

Nishimura et al., "A switch from MafB to MafA expression accompanies differentiation to pancreatic β-cells," Dev. Biol., 293(2):526-539, (2006).

Zhao et al., "The Islet β Cell-enriched MafA Activator Is a Key Regulator of Insulin Gene Transcription," J. Biol. Chem., 280(12):11887-11894, (2005).

Benkhelifa et al., "*maf*A, a novel member of the *maf* proto-oncogene family, displays developmental regulation and mitogenic capacity in avian neuroretina cells," Oncogene, 17:247-254 (1998).

Benkhelifa et al., "Phosphorylation of MafA Is Essential for Its Transcriptional and Biological Properties," Molecular & Cellular Biology, 21(14):4441-4452 (Jul. 2001).

Lu et al., "Heterogeneity in predisposition of hepatic cells to be induced into pancreatic endocrine cells by PDX-1," World Journal of Gastroenterology, 11(15):2277-2282 (2005).

Matsuoka et al., "The MafA transcription factor appears to be responsible for tissue-specific expression of insulin," PNAS, 101(9):2930-2933 (Mar. 2004).

Vial et al., "Transcriptional control of SPARC by v-Jun and other members of the AP1 family of transcription factors," Oncogene, 19:5020-5029 (2000).

Yamada et al., "Differentiation of immature enterocytes into enteroendocrine cells by Pdx1 overexpression," Am. J. Physiol. Gastrointest. Liver Physiol., 281:G229-G236 (2001).

* cited by examiner

```
   1 TATAAAGGGG CGCGCGCGGC TTCGCGTTTA GCCGTGGGAG GCGGGGCCGG CCGGCGGCGC
  61 GGGTGGGGCG CGGGAGCGGT CCCGGAGCAG CCCGAGGCGG CGGCCGCGGG GAGGAGGCGG
 121 CGACGCGGGC CCGGGGTCGC CCGAGACACC TGGCCAGCGG TGCCCCTAGC GCGCCGCCCC
 181 GGAGTTGACC ACGTGAAACT TTTCCCTGCG CCCCTCGGCG CCGCCGCCCC GCGCCGGCGC
 241 CCCCCCGCCC CCGCCGGGAC CGCCGCCCGC GGGGAGCAGG GGGGGGAGAG GCCTGCAGCT
 301 CCCCCACCAC TCCCACGCCG CCCGTCGGGG CGCGGCCGGG CGCGGGCCCC GGGCGATGGC
 361 CGCGGAGCTG GCGATGGGCG CCGAGCTGCC CAGCAGCCCG CTGGCCATCG AGTACGTCAA
 421 CGACTTCGAC CTGATGAAGT TCGAGGTGAA GAAGGAGCCT CCCGAGGCCG AGCGCTTCTG
 481 CCACCGCCTG CCGCCAGGCT CGCTGTCCTC GACGCCGCTC AGCACGCCCT GCTCCTCCGT
 541 GCCCTCCTCG CCCAGCTTCT GCGCGCCCAG CCCGGGCACC GGCGGCGGCG GCGGCGCGGG
 601 GGGCGGCGGC GGCTCGTCTC AGGCCGGGGG CGCCCCCGGG CCGCCGAGCG GGGGCCCCGG
 661 CGCCGTCGGG GGCACCTCGG GGAAGCCGGC GCTGGAGGAT CTGTACTGGA TGAGCGGCTA
 721 CCAGCATCAC CTCAACCCCG AGGCGCTCAA CCTGACGCCC GAGGACGCGG TGGAGGCGCT
 781 CATCGGCAGC GGCCACCACG GCGCGCACCA CGGCGCGCAC CACCCGGCGG CCGCCGCAGC
 841 CTACGAGGCT TTCCGCGGCC CGGGCTTCGC GGGCGGCGGC GGAGCGGACG ACATGGGCGC
 901 CGGCCACCAC CACGGCGCGC ACCACGCCGC CCACCACCAC CACGCCGCCC ACCACCACCA
 961 CCACCACCAC CACCATGGCG GCGCGGGACA CGGCGGTGGC GCGGGCCACC ACGTGCGCCT
1021 GGAGGAGCGC TTCTCCGACG ACCAGCTGGT GTCCATGTCG GTGCGCGAGC TGAACCGGCA
1081 GCTCCGCGGC TTCAGCAAGG AGGAGGTCAT CCGGCTCAAG CAGAAGCGGC GCACGCTCAA
1141 GAACCGCGGC TACGCGCAGT CCTGCCGCTT CAAGCGGGTG CAGCAGCGGC ACATTCTGGA
1201 GAGCGAGAAG TGCCAACTCC AGAGCCAGGT GGAGCAGCTG AAGCTGGAGG TGGGGCGCCT
1261 GGCCAAAGAG CGGGACCTGT ACAAGGAGAA ATACGAGAAG CTGGCGGGCC GGGGCGGCCC
1321 CGGGAGCGCG GGCGGGGCCG GTTTCCCGCG GGAGCCTTCG CCGCCGCAGG CCGGTCCCGG
1381 CGGGGCCAAG GGCACGGCCG ACTTCTTCCT GTAGGCGCCG GACCCCGAGC CCGCGCCGCC
1441 GTCGCCGGGG ACAAGTTCGC GCAGGCCTCT CGGGGCCTCG GCTCGGACTC CGCGGTACAG
1501 GACGTGGACA CCAGGCCCGG CCCGGCCGTG CTGGCCCCGG TGCCAAGTCT GCGGGCGCGG
1561 GGCTGGAGGC CCCTTCGCTC CCGGTCCCCG TTCGCGCGCG TCGGCCCGGG TCGCCGTCCT
1621 GAGGTTGAGC GGAGAACGGT GATTTCTAAG GAAACTTGAG CCAGGTCTAA CTTCTTTCCA
1681 AGCGTCCGCT TGTACATACG TTGAACGTGG TTCTCCGTTC CCACCTTCGC CCTGCCAGCC
1741 TAGAGGGACC GCGCTGCCGT CCCTTCCCGG GTGGCCCCTG CCTGCCCCCG CCCTCCTTCG
1801 TTCTCTTCTC AGCCTCCCTT TCCTTGCCTT TTTTAACTTC CCCTCCCCGT TTTAAAATCG
1861 GTCTTATTTT CGAAGTATTT ATAATTATTA TGCTTGGTGA TTAGAAAAGA AAACCTTGGA
1921 GGAAGCCCCT TCTTTCCCCA GCCGGGGTCC GCCCTCAGTC GCGAGTCACA GCATGAGTCG
1981 CTCGCCAGGA GGGGCCCGGC CCTGCCTGC CCCCTCCCCG CTTGCCCCG ACCCTGCTAC
2041 CGGCGTTCCT TGGAGGTCGA AGCCAGGGAC GTCACCCGTG CTGTGTCCAG GCCTGCTGTC
2101 CTACTATGCT CAACCGGGG TGGGGGAGG GGGGTGAGTC CTGTGCTCAG TCGGGTGGGG
2161 GCTGGCCCGG ATCCCGAGCT GCTGTCTCTC TATGCACCAG AACATATCTG TAACTCCTGG
2221 GGAAATACAT CTTGTTTTAA CCTTCAAGAG AAGTGAAAGA AAAAAGTAAT GCACAGTATT
```

FIG. 1A

```
2281 TCTAGCAGAA AATTTTTTTT TTTAAGAGGA GGCTTGGGCC AGAGCCTTCT GGCATGGGGC
2341 GGGTGGAGAA AGTGTTTTTA TTTTAATTTA AATTGTGTTT CGTTTTGTTT GTGGAATCTT
2401 TCTTTAATGC TTCGTCGCTC TTTGGACTAG CCGGGAGAGA GGGCGAGGAG GCGGGTGCTC
2461 CAGGCCCTGT AGGCTGGGCC AGGCGCCTGG GGGATCTGCC CGTTTTCGGA GGCCCTCAGG
2521 GGCCATCAGT GGGATTCCAG CCGCTCCACA CCCCTCCCCT GAGCACTCGG AGTGGAAGGC
2581 GCGCCGACTC GTTGAAAGTT TTGTTGTGTA GTTGGTTTTC GTTGAGTTCT TTTTTCATTT
2641 GCTACGAAAC TGAGAAAAAG AAAAAAATAC ACAAAATAAA T
```

FIG. 1B

```
   1 ATGGCCGCGG AGCTGGCGAT GGGCGCCGAG CTGCCCAGCA GCCCGCTGGC CATCGAGTAC
  61 GTCAACGACT TCGACCTGAT GAAGTTCGAG GTGAAGAAGG AGCCTCCCGA GGCCGAGCGC
 121 TTCTGCCACC GCCTGCCGCC AGGCTCGCTG TCCTCGACGC CGCTCAGCAC GCCCTGCTCC
 181 TCCGTGCCCT CCTCGCCCAG CTTCTGCGCG CCCAGCCCGG GCACCGGCGG CGGCGGCGGC
 241 GCGGGGGGCG GCGGCGGCTC GTCTCAGGCC GGGGGCGCCC CCGGGCCGCC GAGCGGGGGC
 301 CCCGGCGCCG TCGGGGGCAC CTCGGGGAAG CCGGCGCTGG AGGATCTGTA CTGGATGAGC
 361 GGCTACCAGC ATCACCTCAA CCCCGAGGCG CTCAACCTGA CGCCCGAGGA CGCGGTGGAG
 421 GCGCTCATCG GCAGCGGCCA CCACGGCGCG CACCACGGCG CGCACCACCC GGCGGCCGCC
 481 GCAGCCTACG AGGCTTTCCG CGGCCCGGGC TTCGCGGGCG GCGGCGGAGC GGACGACATG
 541 GGCGCCGGCC ACCACCACGG CGCGCACCAC GCCGCCCACC ACCACCACGC CGCCCACCAC
 601 CACCACCACC ACCACCACCA TGGCGGCGCG GGACACGGCG GTGGCGCGGG CCACCACGTG
 661 CGCCTGGAGG AGCGCTTCTC CGACGACCAG CTGGTGTCCA TGTCGGTGCG CGAGCTGAAC
 721 CGGCAGCTCC GCGGCTTCAG CAAGGAGGAG GTCATCCGGC TCAAGCAGAA GCGGCGCACG
 781 CTCAAGAACC GCGGCTACGC GCAGTCCTGC CGCTTCAAGC GGGTGCAGCA GCGGCACATT
 841 CTGGAGAGCG AGAAGTGCCA ACTCCAGAGC CAGGTGGAGC AGCTGAAGCT GGAGGTGGGG
 901 CGCCTGGCCA AAGAGCGGGA CCTGTACAAG GAGAAATACG AGAAGCTGGC GGGCCGGGGC
 961 GGCCCCGGGA GCGCGGGCGG GGCCGGTTTC CCGCGGGAGC CTTCGCCGCC GCAGGCCGGT
1021 CCCGGCGGGG CCAAGGGCAC GGCCGACTTC TTCCTGTAG
```

FIG. 2A

```
   1 MAAELAMGAE LPSSPLAIEY VNDFDLMKFE VKKEPPEAER FCHRLPPGSL SSTPLSTPCS
  61 SVPSSPSFCA PSPGTGGGGG AGGGGGSSQA GGAPGPPSGG PGAVGGTSGK PALEDLYWMS
 121 GYQHHLNPEA LNLTPEDAVE ALIGSGHHGA HHGAHHPAAA AAYEAFRGPG FAGGGGADDM
 181 GAGHHHGAHH AAHHHHAAHH HHHHHHGGA GHGGGAGHHV RLEERFSDDQ LVSMSVRELN
 241 RQLRGFSKEE VIRLKQKRRT LKNRGYAQSC RFKRVQQRHI LESEKCQLQS QVEQLKLEVG
 301 RLAKERDLYK EKYEKLAGRG GPGSAGGAGF PREPSPPQAG PGGAKGTADF FL.
```

FIG. 2B

| 1 | | 75 | 106 | | 183 | 207 | 227 | 253 | | 281 | 316 | 352 |
|---|---|---|---|---|---|---|---|---|---|---|---|---|
| S/P/T-rich Acidic | | G | | | H | G | EHR | Basic | | L-Zip | | |

Activation Domain    Gly rich domain             His    Gly    DNA binding    Dimerization
                                                                                                                   LLLLYL Based on Blank and Andrew TIBS 22;437-441

FIG. 2C

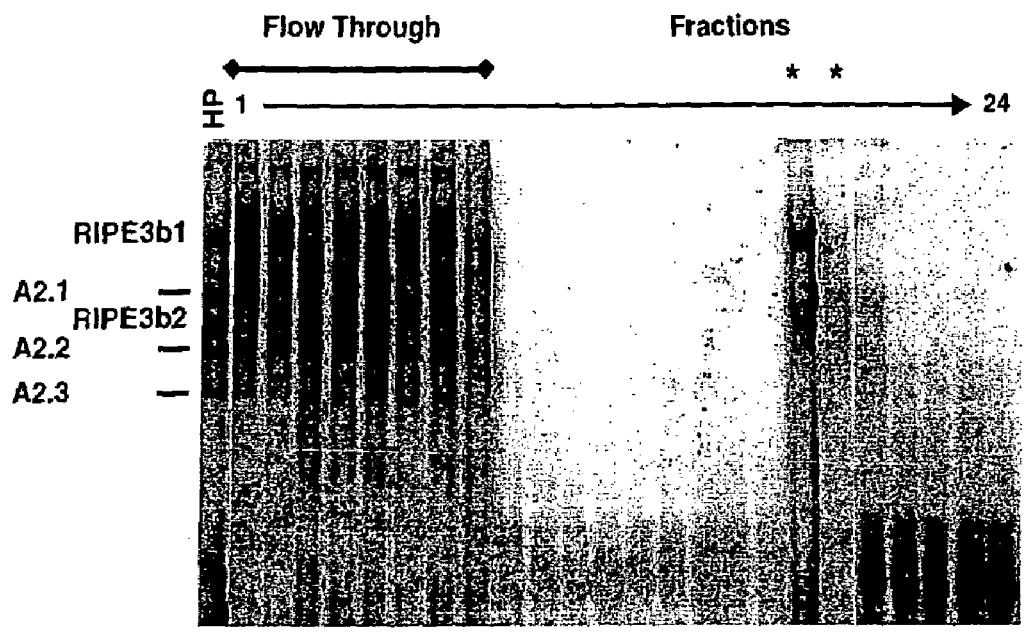
FIG. 3
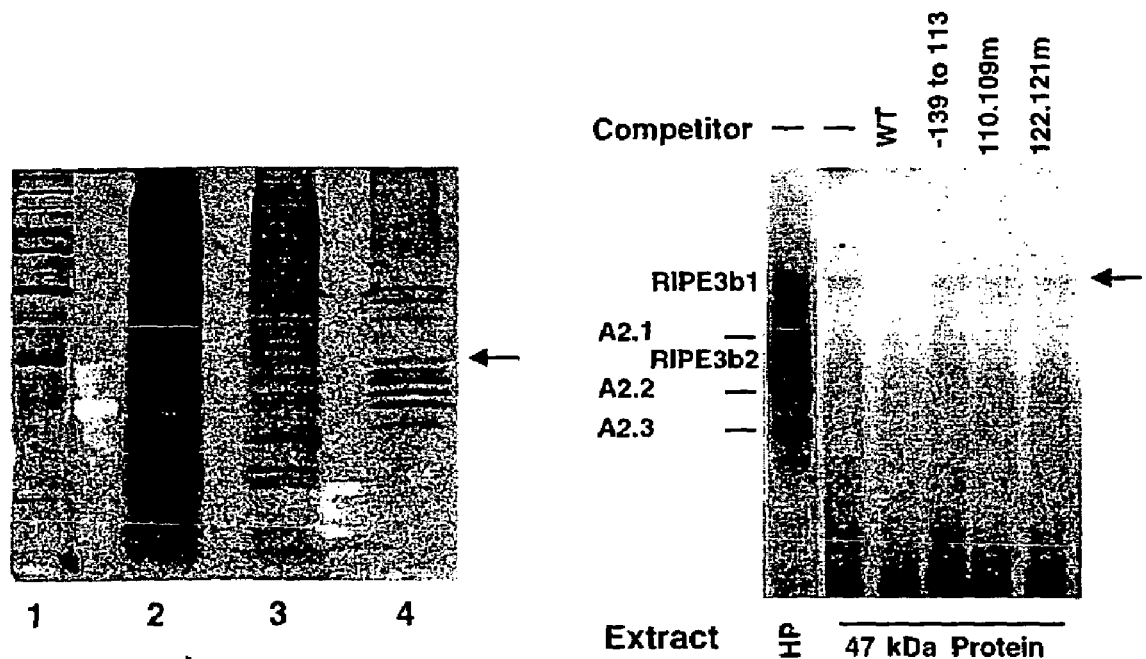
FIG. 4
FIG. 5

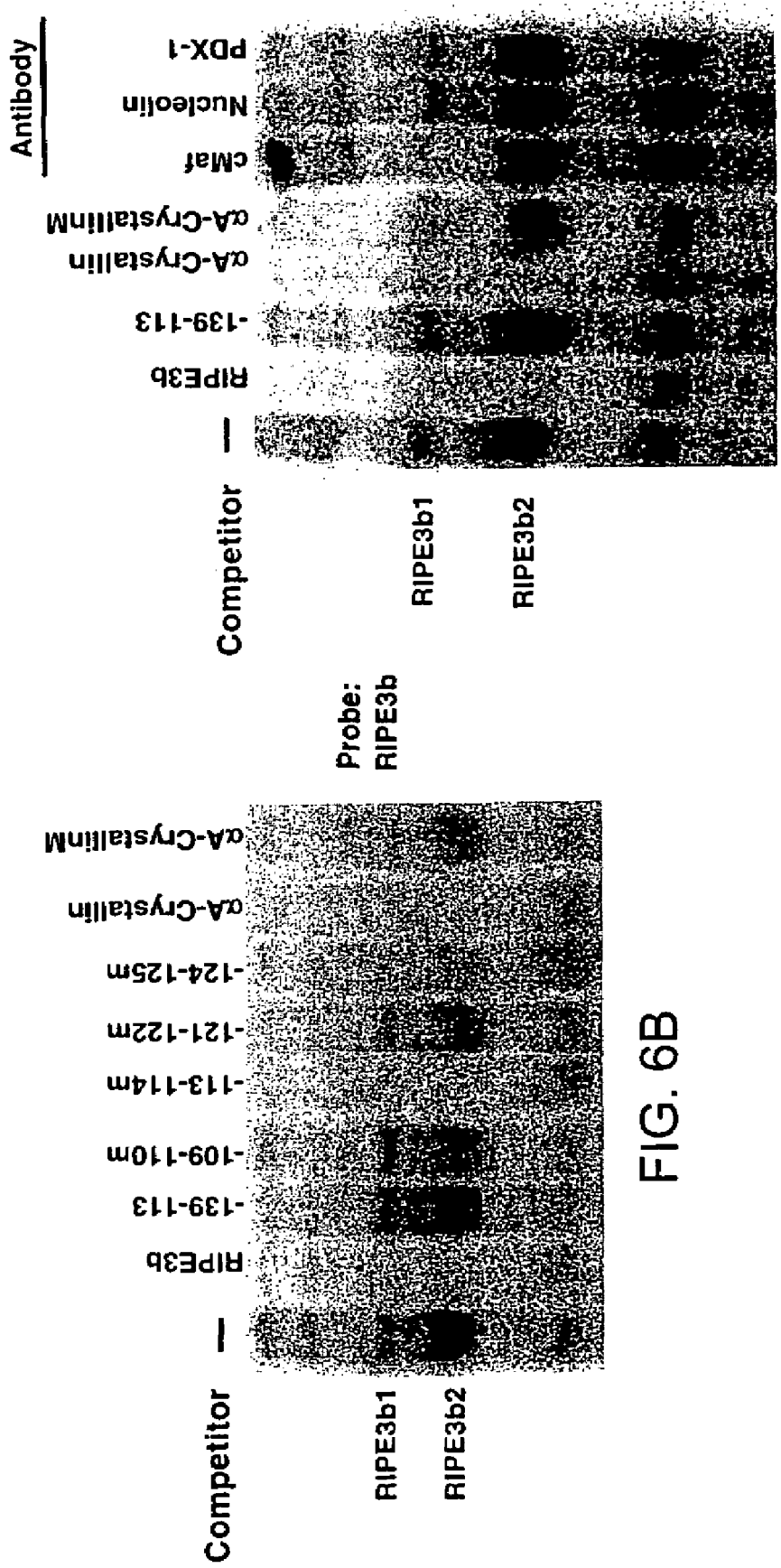

```
                   MAAELAMGAELPSSPLAIEYVNDFDLMKFEVKKEPPEAERFCHRLPPGSLSSTPLSTPCS
                   |        |        |        |        |        |
                   10       20       30       40       50       60
hMafA              MAAELAMGAELPSSPLAIEYVNDFDLMKFEVKKEPPEAERFCHRLPPGSLSSTPLSTPCS 60
mouse MafA AS-data MAAELAMGAELPSSPLAIEYVNDFDLMKFEVKKELPEAERFCHRLPPGSLSSTPLSTPCS 60
m.MafA MGD AS-Analy MAAELAMGAELPSSPLAIEYVNDFDLMKFEVKKEPPEAERFCHRLPPGSLSSTPLSTPCS 60
m.MafA MGD         MAAELAMGAELPSSPLAIEYVNDFDLMKFEVKKEPPEAERFCHRLPPGSLSSTPLSTPCS 60
L-Maf              MASELAMTAELPTSPLAIEYVNDFDLMKFEVKKEPAEAERLCHRLPAGSLSSTPLSTPCS 60
MafA               MASELAMTAELPTSPLAIEYVNDFDLMKFEVKKEPAEAERLCHRLPAGSLSSTPLSTPCS 60
SMaf1              MATDLAMSAELPNSPLAIEYVNDFDLMKFEIKKEPPEADRYCHRLPPGSLSSTPISTPCS 60

SVPSSPSFCAPSPGTGGG--AGGG-----AGGAPGPPSGGPGTVGGASGKPQLEDLYWMS
                   |        |        |        |        |        |
                   70       80       90       100      110      120
hMafA              SVPSSPSFCAPSPGTGGGGGAGGGGGSSQAGGAPGPPSGGPGAVGGTSGKPALEDLYWMS 120
mouse MafA AS-data SVPSSPSFCAPSPGTGGG--AGGGSSAAQAGGAPGPPSGGPGTVGGASGKAVLEDLYWMS 118
m.MafA MGD AS-Analy SVPSSPSFCAPSPGTGGG--AGGGGSAAQAGGAPGPPSGGPGTVGGASGKAVLEDLYWMS 118
m.MafA MGD         ------------------------------------------------------------ 61
L-Maf              SVPSSPSFCAPSPGGQPS-----------------AG----PTAAPLGSKPQLEELYWMS 99
MafA               SVPSSPSFCAPSPGGQPS-----------------AG----PTAAPLGSKPQLEELYWMS 99
SMaf1              SVPSSPSFCAPSPGSQPGQNLVNG-----VNNNNNNSGNGNNNTQGSSGKPQMEDLYWIP 115

GYQHHLNPEALNLTPEDAVEALIGSGHHGAHHGAHHPAAAAAYEAFRGQGFAGGGGADDM
                   |        |        |        |        |        |
                   130      140      150      160      170      180
hMafA              GYQHHLNPEALNLTPEDAVEALIGSGHHGAHHGAHHPAAAAAYEAFRGPGFAGGGGADDM 180
mouse MafA AS-data GYQHHLNPEALNLTPEDAVETLIGSGHHGAHHGAHHPAAAAAYEAFRGQNFASGGGADDM 178
m.MafA MGD AS-Analy GYQHHLNPEALNLTPEDAVEALIGSGHHGAHHGAHHPAAAAAYEAFRGQSFAGGGGADDM 178
m.MafA MGD         --SHHLNPEALNLTPEDAVEALIGSGHHGAHHGAHHPAAAAAYEAFRGQSFAGGGGADDM 118
L-Maf              GYQHHLNPEALNLTPEDAVEALIG----APHHHHHHQSYESFRPQPFGGEELPPAAHHH 155
MafA               GYQHHLNPEALNLTPEDAVEALIG----APHHHHHHQSYESFRPQPFGGEELPPAAHHH 155
SMaf1              NYQHHISPEALNLTPEDAVEALIGNAHHHHHHHHHQPYKGFRGQQYVGKNLSAATNGHHH 175

GAGHHHGAHH-------------------------------GGGGAGHHVRLEERFSDDQL
                   |        |        |        |        |        |
                   190      200      210      220      230      240
hMafA              GAGHHHGAHHAAHHHHAAHHHHHHHHGGAG---------HGGGAGHHVRLEERFSDDQL 231
mouse MafA AS-data GAGHHHGAHHTAHHHHSANHHHHHHHHGGSGHHGGGAGHGGGGAGHHVRLEERFSDDQL 238
m.MafA MGD AS-Analy GAGHHHGAHHTAHHHHSAHHHHHHHHHGGSGHHGGGAGHGGGGAGHHVRLEERFSDDQL 238
m.MafA MGD         GSGHHG----------------------------GGAGHGGGGAGHHVRLEERFSDDQL 149
L-Maf              NAHHHHHH-------------------------------------HHLRLEERFSDDQL 177
MafA               NAHHHHHH-------------------------------------HHLRLEERFSDDQL 177
SMaf1              PVHHHHHHHG-----------------------------------HHAHARLEDRFSDEQL 201

VSMSVRELNRQLRGFSKEEVIRLKQKRRTLKNRGYAQSCRFKRVQQRHILESEKCQLQSQ
                   |        |        |        |        |        |
                   250      260      270      280      290      300
hMafA              VSMSVRELNRQLRGFSKEEVIRLKQKRRTLKNRGYAQSCRFKRVQQRHILESEKCQLQSQ 291
mouse MafA AS-data VSMSVRELNRQLRGFSKEEVIRLKQKRRTLKNRGYAQSCRFKRVQQRHILESEKCQLQSQ 298
m.MafA MGD AS-Analy VSMSVRELNRQLRGFSKEEVIRLKQKRRTLKNRGYAQSCRFKRVQQRHILESEKCQLQSQ 298
m.MafA MGD         VSMSVRELNRQLRGFSKEEVIRLKQKRRTLKNRGYAQSCRFKRVQQRHILESEKCQLQSQ 209
L-Maf              VSMSVRELNRQLRGFSKEEVIRLKQNRRTLKNRGYAQSCRYKRVQQRHILENEKCQLQSQ 237
MafA               VSMSVRELNRQLRGFSKEEVIRLKQKRRTLKNRGYAQSCRYKRVQQRHILENEKCQLQSQ 237
SMaf1              VSMTVRELNRQLRGFSKEEVIRLKQKRRTLKNRGYAQSCRYKRVQQRHMLESEKCTLQSQ 261
```

FIG. 7A

```
                    VEQLKLEVGRLAKERDLYKEKYEKLAGRGGPGGAGGAGAPREPSPAQAGPGAAKG--DFF
                    310       320       330       340       350       360
hMafA               VEQLKLEVGRLAKERDLYKEKYEKLAGRGGPGSAGGAGFPREPSPPQAGPGGAKGTADFF   351
mouse MafA AS-data  VEQLKLEVGRLAKERDLYKEKYEKLAGRGGPGGAGGAGFPREPSPAQAGPGAAKGAPDFF   358
m.MafA MGD AS-Analy VEQLKLEVGRLAKERDLYKEKYEKLAGRGGPGGAGGAGFPREPSPAQAGPGAAKGAPDFF   358
m.MafA MGD          VEQLKLEVGRLAKERDLYKEKYENRSCRGHPVRHAHPAAKPQLQVPTAVRISRRAPVRAS   269
L-Maf               VEQLKQEVSRLAKERDLYKEKYEKLAARGFPREPSPPAAPKTTAADFFM              286
MafA                VEQLKQEVSRLAKERDLYKEKYEKLAARGFPRETSPPAAPKTTAADFFM              286
SMaf1               VEQLKQDVARLIKERDLYKEKYEKLASRAFNGGGNTRDPSSGNHVKTTSTDFFM         315

370 hMafA               L.                                                             353
mouse MafA AS-data  L.                                                             360
m.MafA MGD AS-Analy L.                                                             360
m.MafA MGD          SGSPDRLCRGPSAPRER.                                             287
L-Maf                                                                              286
MafA                                                                               286
SMaf1                                                                              315
```

FIG. 7B

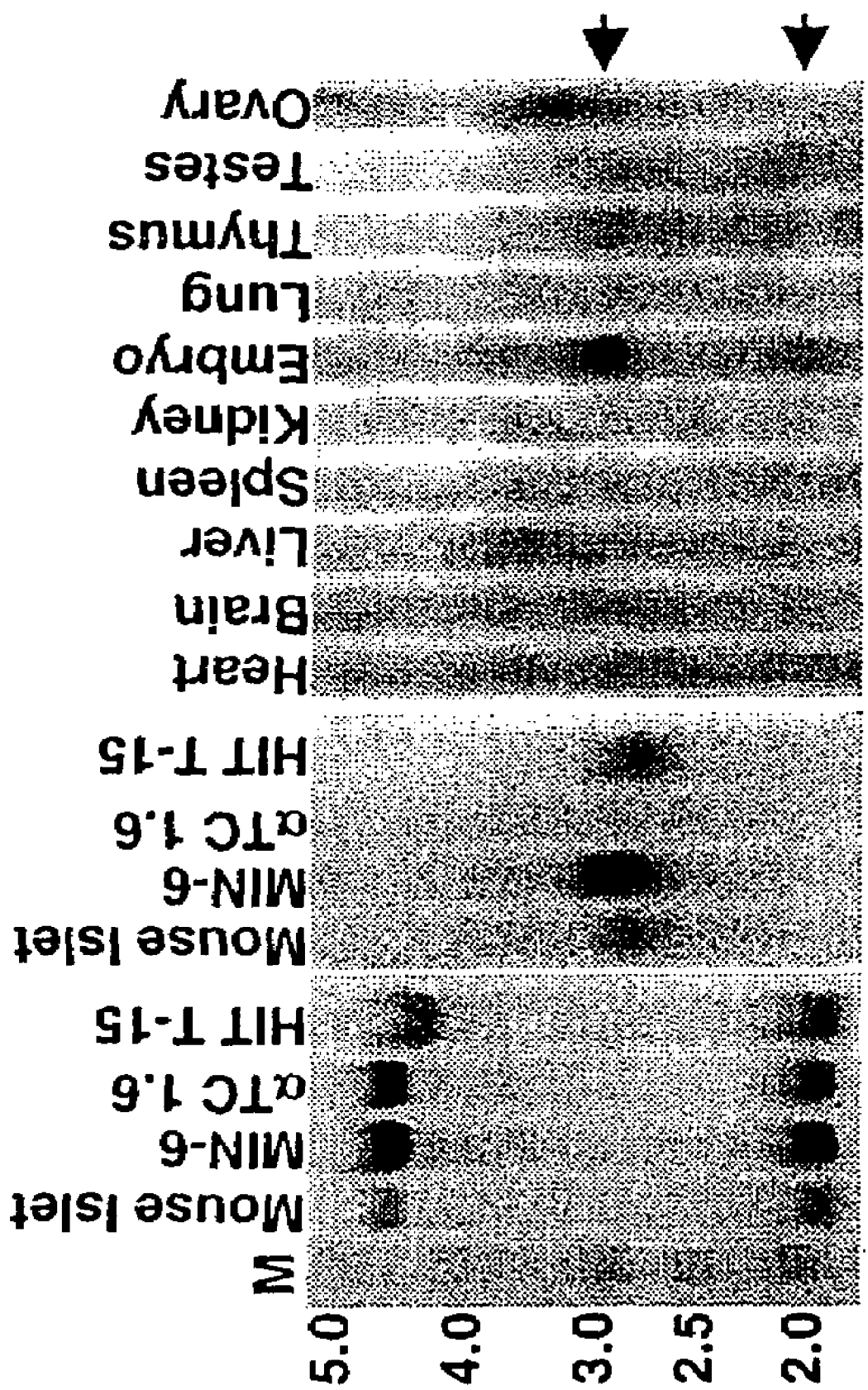

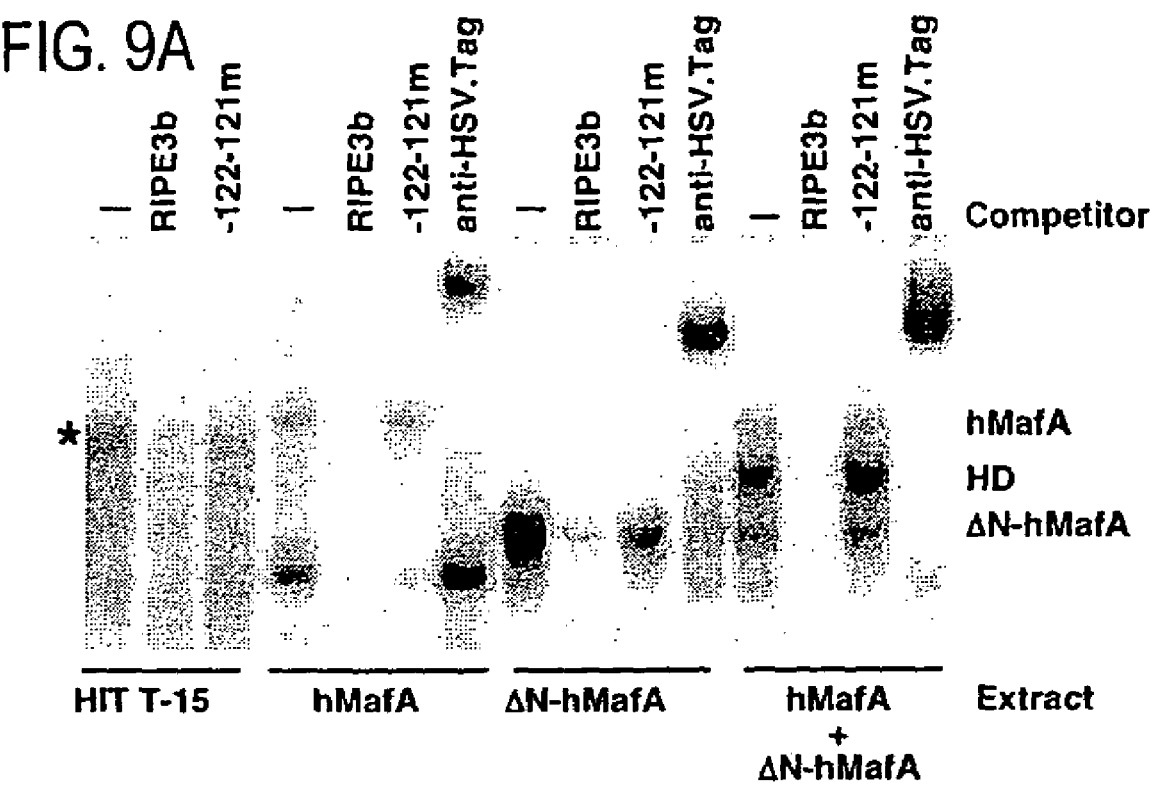
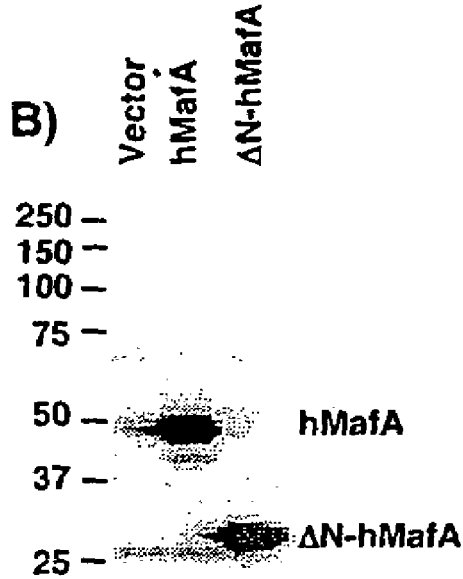
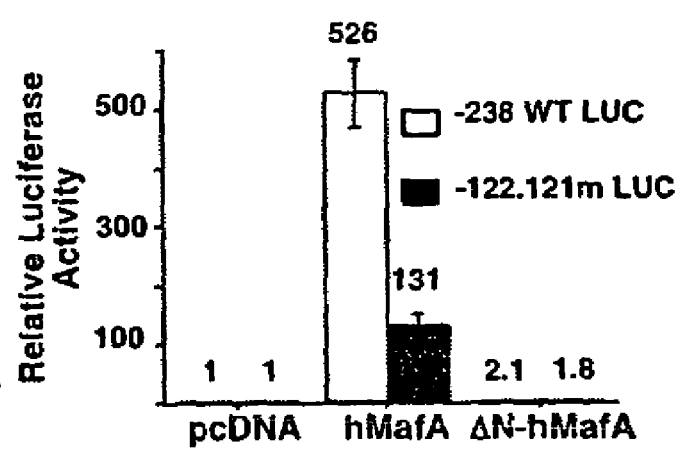
FIG. 9A
FIG. 9B
FIG. 9C

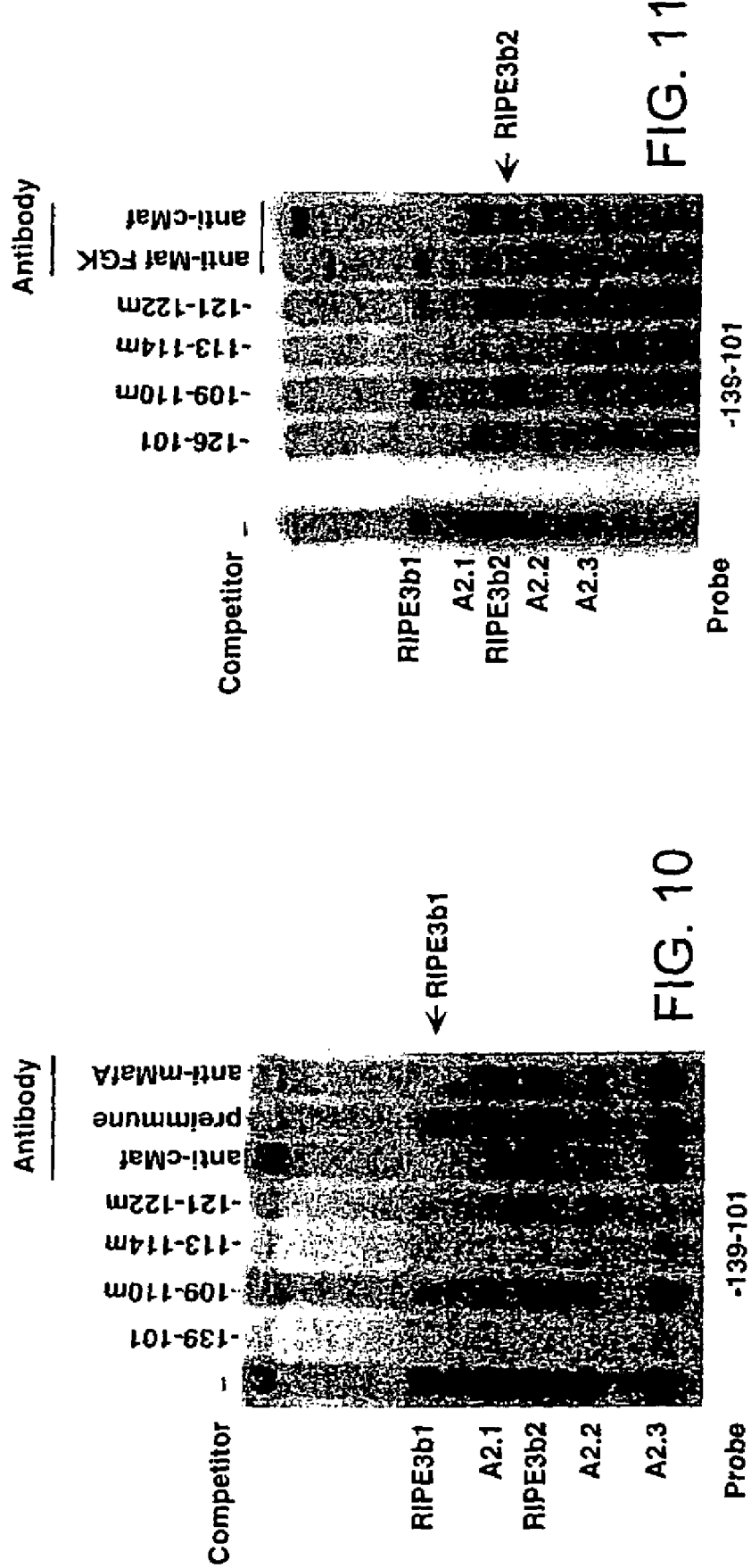

mouse MafA sequence identified based on homology to human MafA
coding sequence and confirmed by PCR amplification of
complete coding sequence from mouse genomic DNA and total RNA
from mouse insulin producing cell line MIN6 and mouse
pancreatic islet. The position of mouse MafA coding sequence
 corresponds to position, 255231 to 256310bp in the
Mus musculus WGS supercontig Mm15_WIFeb01_286

```
LOCUS       NW_000106              512209 bp    DNA     linear    CON 04-JUN-2C
DEFINITION  Mus musculus WGS supercontig Mm15_WIFeb01_286.
ACCESSION   NW_000106 REGION: complement(36916801..37429009)
VERSION     NW_000106.1  GI:20904322
KEYWORDS
SOURCE      house mouse.
  ORGANISM  Mus musculus
            Eukaryota; Metazoa; Chordata; Craniata; Vertebrata; Euteleostomi;
            Mammalia; Eutheria; Rodentia; Sciurognathi; Muridae; Murinae; Mus
REFERENCE   1  (bases 1 to 512209)
  AUTHORS   NCBI Annotation Project.
  TITLE     Direct Submission
  JOURNAL   Submitted (15-MAY-2002) National Center for Biotechnology
            Information, NIH, Bethesda, MD 20894, USA
COMMENT     GENOME ANNOTATION REFSEQ:  NCBI contigs are derived from assemble
            genomic sequence data. They may include both draft and finished
            sequence.

BASE COUNT   121167 a 121434 c 125222 g 132482 t 11904 others
ORIGIN
              10         20         30         40         50         60
atggccgcggagctggcgat gggcgcagagctgcccagca gcccactggccatcgagtac  60
gtcaacgacttcgacctgat gaagttcgaggtgaagaagg agccgcccgaggccgagcgc 120
ttctgccaccgcctgccgcc cggctcgctgtcctcgacgc ccctcagcacgcccctgctcc 180
tcggtgccctcttcgcccag cttctgcgcacccagcccgg gcacaggcggcggcgcgggc 240
ggcggggcagcgcggctca ggccggggcgccccggggc cgccgagtggaggccccggc 300
             310        320        330        340        350        360
actgtcgggggcgcctcagg aaaagcggtgctggaggatc tgtactggatgagcgggtac 360
cagcaccacctgaaccccga ggcgctcaacctgacgccgg aggacgcggtggaggcgctc 420
atcggcagcggccaccacgg cgcgcaccacggcgcgcatc accccggcggctgctgcggcc 480
tatgaggccttccggggtca gagcttcgcgggcggcggcg gcgcggacgacatgggtgcc 540
ggccaccaccacggcgcaca ccacactgcccaccatcatc actctgccaccatcaccat 600
```

```
caccaccatcaccaccacgg aggctctggccaccacggcg gaggcgcgggtcacggcgga 660
ggcggcgcggcaggccacacgt gcgcttggaggagcgcttct ccgacgaccagctggtatcc 720
atgtccgtgcgggagctgaa ccggcagctccgggcttca gcaaggaggtcatccga 780
ctgtcgtgcgggagctgaa ccggcagctccgggcttca gcaaggaggtcatccga 780
ctgaaacagaagcggcgcac gctcaagaaccgcggctacg cgcagtcgtgccgcttcaag 840
cgggtgcagcagcggcacat tctggagagcgagaagtgcc agctccagagccaggtgggag 900
                      910        920        930        940        950        960
cagctgaagctggaggtggg gcgtctggccaagagcggg acctgtacaaggagaaatac 960
gagaagtttggcggccgggg cggcccgggggcgcggggcg gggccggcttccctcgggag 1020
ccctcgccagcgcaggctgg ccccgggggcggccaaaggcg caccgactcttctgtga 1080
```

FIG. 12B

Annotation of mouse supercontig Mm15_WIFeb01_286 predicts a
gene similar to MafA. The gene contains four exons and the
following sequence represents the coding region of this gene.
However, the sequence is significantly different than the
mouse MafA gene as determined by sequence comparision
with human MafA coding sequence and experimentally identified
cDNA, both of which lack an intron within the coding region.

```
LOCUS       NW_000106             512209 bp    DNA     linear   CON 04-JUN-20
DEFINITION  Mus musculus WGS supercontig Mm15_WIFeb01_286.
ACCESSION   NW_000106 REGION: complement(36916801..37429009)
VERSION     NW_000106.1  GI:20904322 mRNA            join(255231..255413,255594..255765,255853..256195
                    ,256815..256977)
                    /gene="LOC239540"
                    /product="similar to bZip transcription factor MafA"
                    /note="Derived by automated computational analysis using
                    gene prediction method: GenomeScan."
                    /transcript_id="XM_139446.1"
                    /db_xref="GI:20903992"
                    /db_xref="InterimID:239540"
```

```
          10         20         30         40         50         60
atggccgcggagctggcgat gggcgcagagctgcccagca gcccactggccatcgagtac  60
gtcaacgacttcgacctgat gaagttcgcggtgcagaagg agccgcccgaggccgagcgc 120
ttctgccaccgcctgccgcc cggctcgctgtcctcgacgc ccctcagcacgccctgctcc 180
tcgcaccacctgaaccccga ggcgctcaacctgacgccgg aggacgcggtggaggcgctc 240
atcggcagcggccaccacgg cgcgcaccacggcgcgcatc acccggcggctgctgcggcc 300
         310        320        330        340        350        360
tatgaggccttccggggtca gagcttcgcgggcggcggcg gcgcggacgacatgggctct 360
ggccaccacggcggaggcgc gggtcacggcggaggcggcg caggccaccacgtgcgcttg 420
gaggagcgcttctccgacga ccagctggtatccatgtccg tgcgggagctgaaccggcag 480
ctccgcggcttcagcaagga ggggtcatccgactgaaac agaagcggcgcacgctcaag 540
aaccgcggctacgcgcagtc gtgccgcttcaagcgggtgc agcagcggcacttctggag 600
         610        620        630        640        650        660
agcgagaagtgccagctcca gagccaggtggagcagctga agctggaggtggggcgtctg 660
gccaaggagcgggacctgta caaggagaaatacgagaacc gcagctgccggggtcatcct 720
gtccgccatgcgcaccccgc cgccaagcccagctccagg tacctaccgcggtgcgcatc 780
tcccgccgggcccggtccg agcgtcttcggggtcgccgg ataqactttgccggggtccc 840
tcggcgccccgggaacggtg a 861
```

FIG. 13

SEQUENCE LISTING

<160> NUMBER OF SEQ ID NOS: 24

<210> SEQ ID NO 1
<211> LENGTH: 2681
<212> TYPE: DNA
<213> ORGANISM: Homo sapiens

<400> SEQUENCE: 1

| | | | | | |
|---|---|---|---|---|---|
| tataaagggg | cgcgcgcggc | ttcgcgttta | gccgtgggag | gcggggccgg | ccggcggcgc | 60 |
| gggtggggcg | cgggagcggt | cccggagcag | cccgaggcgg | cggccgcggg | gaggaggcgg | 120 |
| cgacgcgggc | ccggggtcgc | ccgagacacc | tggccagcgg | tgccctagc | gcgccgcccc | 180 |
| ggagttgacc | acgtgaaact | tttccctgcg | cccctcggcg | ccgccgcccc | cgccggcgc | 240 |
| ccccccgccc | ccgccgggac | cgccgcccgc | ggggagcagg | gggggagag | gcctgcagct | 300 |
| cccccaccac | tcccacgccg | cccgtcgggg | cgcggccggg | cgcgggcccc | gggcgatggc | 360 |
| cgcggagctg | gcgatggggcg | ccgagctgcc | cagcagcccg | ctggccatcg | agtacgtcaa | 420 |
| cgacttcgac | ctgatgaagt | tcgaggtgaa | gaaggagcct | cccgaggccg | agcgcttctg | 480 |
| ccaccgcctg | ccgccaggct | cgctgtcctc | gacgccgctc | agcacgccct | gctcctccgt | 540 |
| gccctcctcg | cccagcttct | gcgcgcccag | cccgggcacc | ggcggcggcg | gcggcgcggg | 600 |
| gggcggcggc | ggctcgtctc | aggccggggg | cgcccccggg | ccgccgagcg | ggggcccccgg | 660 |
| cgccgtcggg | ggcaccctcgg | ggaagccggc | gctggaggat | ctgtactgga | tgagcggcta | 720 |
| ccagcatcac | ctcaacccccg | aggcgctcaa | cctgacgccc | gaggacgcgg | tggaggcgct | 780 |
| catcggcagc | ggccaccacg | gcgcgcacca | cggcgcgcac | cacccggcgg | ccgccgcagc | 840 |
| ctacgaggct | ttccgcggcc | cgggcttcgc | gggcggcggc | ggagcggacg | acatgggcgc | 900 |
| cggccaccac | cacggcgcgc | accacgccgc | ccaccaccac | cacgccgccc | accaccaca | 960 |
| ccaccaccac | caccatggcg | gcgcgggaca | cggcggtggc | gcgggccacc | acgtgcgcct | 1020 |
| ggaggagcgc | ttctccgacg | accagctggt | gtccatgtcg | gtgcgcgagc | tgaaccggca | 1080 |
| gctccgcggc | ttcagcaagg | aggaggtcat | ccggctcaag | cagaagcggc | gcacgctcaa | 1140 |
| gaaccgcggc | tacgcgcagt | cctgccgctt | caagcgggtg | cagcagcggc | acattctgga | 1200 |
| gagcgagaag | tgccaactcc | agagccaggt | ggagcagctg | aagctggagg | tggggcgcct | 1260 |
| ggccaaagag | cgggacctgt | acaaggagaa | atacgagaag | ctggcggggcc | ggggcggccc | 1320 |
| cgggagcgcg | ggcggggccg | gtttcccgcg | ggagccttcg | ccgccgcagg | ccggtcccgg | 1380 |
| cggggccaag | ggcacggccg | acttcttcct | gtaggcgccg | gaccccgagc | ccgcgccgcc | 1440 |
| gtcgccgggg | acaagttcgc | gcaggcctct | cggggcctcg | gctcggactc | cgcggtacag | 1500 |
| gacgtggaca | ccaggcccgg | cccggccgtg | ctggccccgg | tgccaagtct | gcgggcgcgg | 1560 |
| ggctggaggc | cccttcgctc | ccggtcccgg | ttcgcgcgcg | tcggcccggg | tcgccgtcct | 1620 |
| gaggttgagc | ggagaacggt | gatttctaag | gaaacttgag | ccaggtctaa | cttctttcca | 1680 |
| agcgtccgct | tgtacatacg | ttgaacgtgg | ttctccgttc | ccaccttcgc | cctgccagcc | 1740 |
| tagagggacc | gcgctgccgt | cccttcccgg | gtggcccctg | cctgccccg | ccctccttcg | 1800 |
| ttctcttctc | agcctccctt | tccttgcctt | ttttaacttc | ccctcccgt | tttaaaatcg | 1860 |
| gtcttatttt | cgaagtattt | ataattatta | tgcttggtga | ttagaaaaga | aaaccttgga | 1920 |
| ggaagccccc | tctttcccca | gccggggtcc | gccctcagtc | gcgagtcaca | gcatgagtcg | 1980 |
| ctcgccagga | ggggcccggc | ccctgcctgc | ccctcccccg | cttgccccg | accctgctac | 2040 |

-continued

```
cggcgttcct tggaggtcga agccagggac gtcacccgtg ctgtgtccag gcctgctgtc    2100
ctactatgct caaccggggg tgggggagg ggggtgagtc ctgtgctcag tcgggtgggg    2160
gctggcccgg atcccgagct gctgtctctc tatgcaccag aacatatctg taactcctgg    2220
ggaaatacat cttgttttaa ccttcaagag aagtgaaaga aaaagtaat gcacagtatt    2280 tctagcagaa aattttttt tttaagagga ggcttgggcc agagccttct ggcatggggc    2340
gggtggagaa agtgttttta ttttaattta aattgtgttt cgttttgttt gtggaatctt    2400
tctttaatgc ttcgtcgctc tttggactag ccgggagaga gggcgaggag gcgggtgctc    2460
caggccctgt aggctgggcc aggcgcctgg gggatctgcc cgttttcgga ggccctcagg    2520
ggccatcagt gggattccag ccgctccaca cccctcccct gagcactcgg agtggaaggc    2580
gcgccgactc gttgaaagtt ttgttgtgta gttggttttc gttgagttct tttttcattt    2640
gctacgaaac tgagaaaaag aaaaaaatac acaaaataaa t                        2681
```

<210> SEQ ID NO 2
<211> LENGTH: 352
<212> TYPE: PRT
<213> ORGANISM: Homo sapiens

<400> SEQUENCE: 2

```
Met Ala Ala Glu Leu Ala Met Gly Ala Glu Leu Pro Ser Ser Pro Leu
  1               5                  10                  15

Ala Ile Glu Tyr Val Asn Asp Phe Asp Leu Met Lys Phe Glu Val Lys
             20                  25                  30

Lys Glu Pro Pro Glu Ala Glu Arg Phe Cys His Arg Leu Pro Pro Gly
         35                  40                  45

Ser Leu Ser Ser Thr Pro Leu Ser Thr Pro Cys Ser Ser Val Pro Ser
     50                  55                  60

Ser Pro Ser Phe Cys Ala Pro Ser Pro Gly Thr Gly Gly Gly Gly
 65                  70                  75                  80

Ala Gly Gly Gly Gly Ser Ser Gln Ala Gly Gly Ala Pro Gly Pro
                 85                  90                  95

Pro Ser Gly Gly Pro Gly Ala Val Gly Gly Thr Ser Gly Lys Pro Ala
            100                 105                 110

Leu Glu Asp Leu Tyr Trp Met Ser Gly Tyr Gln His His Leu Asn Pro
        115                 120                 125

Glu Ala Leu Asn Leu Thr Pro Glu Asp Ala Val Glu Ala Leu Ile Gly
    130                 135                 140

Ser Gly His His Gly Ala His Gly Ala His His Pro Ala Ala Ala
145                 150                 155                 160

Ala Ala Tyr Glu Ala Phe Arg Gly Pro Gly Phe Ala Gly Gly Gly Gly
                165                 170                 175

Ala Asp Asp Met Gly Ala Gly His His Gly Ala His His Ala Ala
            180                 185                 190

His His His His Ala Ala His His His His His His His His Gly
        195                 200                 205

Gly Ala Gly His Gly Gly Ala Gly His His Val Arg Leu Glu Glu
    210                 215                 220

Arg Phe Ser Asp Asp Gln Leu Val Ser Met Ser Val Arg Glu Leu Asn
225                 230                 235                 240

Arg Gln Leu Arg Gly Phe Ser Lys Glu Glu Val Ile Arg Leu Lys Gln
                245                 250                 255
```

```
Lys Arg Arg Thr Leu Lys Asn Arg Gly Tyr Ala Gln Ser Cys Arg Phe
            260                 265                 270

Lys Arg Val Gln Gln Arg His Ile Leu Glu Ser Glu Lys Cys Gln Leu
        275                 280                 285

Gln Ser Gln Val Glu Gln Leu Lys Leu Glu Val Gly Arg Leu Ala Lys
    290                 295                 300

Glu Arg Asp Leu Tyr Lys Glu Lys Tyr Glu Lys Leu Ala Gly Arg Gly
305                 310                 315                 320

Gly Pro Gly Ser Ala Gly Gly Ala Gly Phe Pro Arg Glu Pro Ser Pro
                325                 330                 335

Pro Gln Ala Gly Pro Gly Gly Ala Lys Gly Thr Ala Asp Phe Phe Leu
            340                 345                 350

<210> SEQ ID NO 3
<211> LENGTH: 861
<212> TYPE: DNA
<213> ORGANISM: Mus musculus

<400> SEQUENCE: 3
atggccgcgg agctggcgat gggcgcagag ctgcccagca gcccactggc catcgagtac      60
gtcaacgact cgacctgat gaagttcgag gtgaagaagg agccgcccga ggccgagcgc     120
ttctgccacc gcctgccgcc cggctcgctg tcctcgacgc ccctcagcac gccctgctcc     180
tcgcaccacc tgaaccccga ggcgctcaac ctgacgccgg aggacgcggt ggaggcgctc     240
atcggcagcg gccaccacgg cgcgcaccac ggcgcgcatc acccggcggc tgctgcggcc     300
tatgaggcct tccggggtca gagcttcgcg ggcggcggcg gcgcggacga catgggctct     360
ggccaccacg gcggaggcgc gggtcacggc ggaggcggcg caggccacca cgtgcgcttg     420
gaggagcgct tctccgacga ccagctggta tccatgtccg tgcgggagct gaaccggcag     480
ctccgcggct tcagcaagga ggaggtcatc cgactgaaac agaagcggcg cacgctcaag     540
aaccgcggct acgcgcagtc cgtgccgctt caagcgggtgc agcagcggca cattctggag     600
agcgagaagt gccagctcca gagccaggtg agcagctga agctggaggt ggggcgtctg     660
gccaaggagc gggacctgta caaggagaaa tacgagaacc gcagctgccg gggtcatcct     720
gtccgccatg cgcaccccgc cgccaagccc cagctccagg tacctaccgc ggtgcgcatc     780
tcccgccggg ccccggtccg agcgtcttcg gggtcgccgg atagactttg ccggggtccc     840
tcggcgcccc gggaacggtg a                                                861

<210> SEQ ID NO 4
<211> LENGTH: 1059
<212> TYPE: DNA
<213> ORGANISM: Homo sapiens

<400> SEQUENCE: 4
atggccgcgg agctggcgat gggcgccgag ctgcccagca gcccgctggc catcgagtac      60
gtcaacgact cgacctgat gaagttcgag gtgaagaagg agcctcccga ggccgagcgc     120
ttctgccacc gcctgccgcc aggctcgctg tcctcgacgc cgtcagcac gccctgctcc     180 tccgtgccct cctcgcccag cttctgcgcg cccagcccgg caccggcgg cggcggcggc     240 gcgggggggcg gcggcggctc gtctcaggcc ggggcgccc ccgggccgcc gagcggggggc     300 cccgcgccg tcgggggcac ctcggggaag ccggcgctgg aggatctgta ctggatgagc     360
ggctaccagc atcacctcaa ccccgaggcg ctcaacctga cgcccgagga cgcggtggag     420
gcgctcatcg gcagcggcca ccacggcgcg caccacggcg cgcaccaccc ggcggccgcc     480
```

-continued

```
gcagcctacg aggctttccg cggcccgggc ttcgcgggcg gcggcggagc ggacgacatg      540
ggcgccggcc accaccacgg cgcgcaccac gccgcccacc accaccacgc cgcccaccac      600
caccaccacc accaccacca tggcggcgcg ggacacggcg gtggcgcggg ccaccacgtg      660
cgcctggagg agcgcttctc cgacgaccag ctggtgtcca tgtcggtgcg cgagctgaac      720
cggcagctcc gcggcttcag caaggaggag gtcatccggc tcaagcagaa gcggcgcacg      780
ctcaagaacc gcggctacgc gcagtcctgc cgcttcaagc gggtgcagca gcggcacatt      840
ctggagagcg agaagtgcca actccagagc caggtggagc agctgaagct ggaggtgggg      900
cgcctggcca agagcgggga cctgtacaag gagaaatacg agaagctggc gggccggggc      960
ggccccggga gcgcgggcgg ggccggtttc ccgcgggagc cttcgccgcc gcaggccggt     1020
cccggcgggg ccaagggcac ggccgacttc ttcctgtag                           1059
```

<210> SEQ ID NO 5
<211> LENGTH: 1080
<212> TYPE: DNA
<213> ORGANISM: Mus musculus

<400> SEQUENCE: 5

```
atggccgcgg agctggcgat gggcgcagag ctgcccagca gcccactggc catcgagtac       60
gtcaacgact tcgacctgat gaagttcgag gtgaagaagg agccgcccga ggccgagcgc      120
ttctgccacc gcctgccgcc cggctcgctg tcctcgacgc ccctcagcac gccctgctcc      180
tcggtgccct cttcgcccag cttctgcgca cccagcccgg gcacaggcgg cggcgcgggc      240
ggcgggggca gcgcggctca ggccgggggc gccccggggc cgccgagtgg aggccccggc      300
actgtcgggg gcgcctcagg aaaagcggtg ctggaggatc tgtactggat gagcgggtac      360
cagcaccacc tgaaccccga ggcgctcaac ctgacgccgg aggacgcggt ggaggcgctc      420
atcggcagcg ccaccacgg cgcgcaccac ggcgcgcatc cccggcggc tgctgcggcc      480 tatgaggcct ccggggtca gagcttcgcg gcggcggcg cgcggacga catgggtgcc      540 ggccaccacc acgcgcaca ccacactgcc caccatcatc actctgccca ccatcaccat      600
caccaccatc accaccacgg aggctctggc caccacggcg gaggcgcggg tcacggcgga      660
ggcggcgcag gccaccacgt gcgcttggag gagcgcttct ccgacgacca gctggtatcc      720
atgtccgtgc gggagctgaa ccggcagctc cgcggcttca gcaaggagga ggtcatccga      780
ctgaaacaga gcggcgcac gctcaagaac gcggctacg cgcagtcgtg ccgcttcaag      840
cgggtgcagc agcggcacat tctggagagc gagaagtgcc agctccagag ccaggtggag      900
cagctgaagc tggaggtggg gcgtctggcc aaggagcggg acctgtacaa ggagaaatac      960
gagaagttgg cgggccgggg cggccccggg ggcgcgggcg gggccggctt ccctcgggag     1020
ccctcgccag cgcaggctgg ccccgggggcg gccaaaggcg cacccgactt ctttctgtga     1080
```

<210> SEQ ID NO 6
<211> LENGTH: 359
<212> TYPE: PRT
<213> ORGANISM: Mus musculus

<400> SEQUENCE: 6

```
Met Ala Ala Glu Leu Ala Met Gly Ala Glu Leu Pro Ser Ser Pro Leu
 1               5                   10                  15

Ala Ile Glu Tyr Val Asn Asp Phe Asp Leu Met Lys Phe Glu Val Lys
             20                  25                  30
```

```
Lys Glu Pro Pro Glu Ala Glu Arg Phe Cys His Arg Leu Pro Pro Gly
            35                  40                  45

Ser Leu Ser Ser Thr Pro Leu Ser Thr Pro Cys Ser Ser Val Pro Ser
        50                  55                  60

Ser Pro Ser Phe Cys Ala Pro Ser Pro Gly Thr Gly Gly Gly Ala Gly
65                  70                  75                  80

Gly Gly Gly Ser Ala Ala Gln Ala Gly Ala Pro Gly Pro Pro Ser
                85                  90                  95

Gly Gly Pro Gly Thr Val Gly Gly Ala Ser Gly Lys Ala Val Leu Glu
            100                 105                 110

Asp Leu Tyr Trp Met Ser Gly Tyr Gln His His Leu Asn Pro Glu Ala
            115                 120                 125

Leu Asn Leu Thr Pro Glu Asp Ala Val Glu Ala Leu Ile Gly Ser Gly
        130                 135                 140

His His Gly Ala His His Gly Ala His His Pro Ala Ala Ala Ala
145                 150                 155                 160

Tyr Glu Ala Phe Arg Gly Gln Ser Phe Ala Gly Gly Gly Gly Ala Asp
                165                 170                 175

Asp Met Gly Ala Gly His His Gly Ala His His Thr Ala His His
            180                 185                 190

His His Ser Ala His His His His His His His His Gly Gly
        195                 200                 205

Ser Gly His His Gly Gly Ala Gly His Gly Gly Gly Ala Gly
            210                 215                 220

His His Val Arg Leu Glu Glu Arg Phe Ser Asp Asp Gln Leu Val Ser
225                 230                 235                 240

Met Ser Val Arg Glu Leu Asn Arg Gln Leu Arg Gly Phe Ser Lys Glu
                245                 250                 255

Glu Val Ile Arg Leu Lys Gln Lys Arg Arg Thr Leu Lys Asn Arg Gly
            260                 265                 270

Tyr Ala Gln Ser Cys Arg Phe Lys Arg Val Gln Gln Arg His Ile Leu
        275                 280                 285

Glu Ser Glu Lys Cys Gln Leu Gln Ser Gln Val Glu Gln Leu Lys Leu
        290                 295                 300

Glu Val Gly Arg Leu Ala Lys Glu Arg Asp Leu Tyr Lys Glu Lys Tyr
305                 310                 315                 320

Glu Lys Leu Ala Gly Arg Gly Pro Gly Ala Gly Gly Ala Gly
            325                 330                 335

Phe Pro Arg Glu Pro Ser Pro Ala Gln Ala Gly Pro Gly Ala Ala Lys
                340                 345                 350

Gly Ala Pro Asp Phe Phe Leu
            355

<210> SEQ ID NO 7
<211> LENGTH: 359
<212> TYPE: PRT
<213> ORGANISM: Mus musculus

<400> SEQUENCE: 7

Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Leu Pro Glu Ala Glu Arg Phe Cys His Arg Leu Pro Pro Gly
            35                  40                  45
```

```
Ser Leu Ser Ser Thr Pro Leu Ser Thr Pro Cys Ser Ser Val Pro Ser
     50                  55                  60

Ser Pro Ser Phe Cys Ala Pro Ser Pro Gly Thr Gly Gly Ala Gly
 65                  70                  75                  80

Gly Gly Ser Ser Ala Ala Gln Ala Gly Ala Pro Gly Pro Pro Ser
                 85                  90                  95

Gly Gly Pro Gly Thr Val Gly Gly Ala Ser Gly Lys Ala Val Leu Glu
            100                 105                 110

Asp Leu Tyr Trp Met Ser Gly Tyr Gln His His Leu Asn Pro Glu Ala
            115                 120                 125

Leu Asn Leu Thr Pro Glu Asp Ala Val Glu Thr Leu Ile Gly Ser Gly
            130                 135                 140

His His Gly Ala His His Gly Ala His His Pro Ala Ala Ala Ala
145                 150                 155                 160

Tyr Glu Ala Phe Arg Gly Gln Asn Phe Ala Ser Gly Gly Gly Ala Asp
                165                 170                 175

Asp Met Gly Ala Gly His His His Gly Ala His His Thr Ala His His
            180                 185                 190

His His Ser Ala Asn His His His His His His His Gly Gly
            195                 200                 205

Ser Gly His His Gly Gly Ala Gly His Gly Gly Gly Ala Gly
            210                 215                 220

His His Val Arg Leu Glu Glu Arg Phe Ser Asp Asp Gln Leu Val Ser
225                 230                 235                 240

Met Ser Val Arg Glu Leu Asn Arg Gln Leu Arg Gly Phe Ser Lys Glu
                245                 250                 255

Glu Val Ile Arg Leu Lys Gln Lys Arg Arg Thr Leu Lys Asn Arg Gly
            260                 265                 270

Tyr Ala Gln Ser Cys Arg Phe Lys Arg Val Gln Gln Arg His Ile Leu
            275                 280                 285

Glu Ser Glu Lys Cys Gln Leu Gln Ser Gln Val Glu Gln Leu Lys Leu
            290                 295                 300

Glu Val Gly Arg Leu Ala Lys Glu Arg Asp Leu Tyr Lys Glu Lys Tyr
305                 310                 315                 320

Glu Lys Leu Ala Gly Arg Gly Gly Pro Gly Ala Gly Gly Ala Gly
                325                 330                 335

Phe Pro Arg Glu Pro Ser Pro Ala Gln Ala Gly Pro Gly Ala Ala Lys
            340                 345                 350

Gly Ala Pro Asp Phe Phe Leu
            355

<210> SEQ ID NO 8
<211> LENGTH: 286
<212> TYPE: PRT
<213> ORGANISM: Mus musculus

<400> SEQUENCE: 8

Met Ala Ala Glu Leu Ala Met Gly Ala Glu Leu Pro Ser Ser Pro Leu
 1               5                  10                  15

Ala Ile Glu Tyr Val Asn Asp Phe Asp Leu Met Lys Phe Glu Val Lys
                20                  25                  30

Lys Glu Pro Pro Glu Ala Glu Arg Phe Cys His Arg Leu Pro Pro Gly
            35                  40                  45

Ser Leu Ser Ser Thr Pro Leu Ser Thr Pro Cys Ser Ser His His Leu
```

```
                50                  55                  60
Asn Pro Glu Ala Leu Asn Leu Thr Pro Glu Asp Ala Val Glu Ala Leu
 65                  70                  75                  80

Ile Gly Ser Gly His His Gly Ala His His Gly Ala His His Pro Ala
                     85                  90                  95

Ala Ala Ala Ala Tyr Glu Ala Phe Arg Gly Gln Ser Phe Ala Gly Gly
                100                 105                 110

Gly Gly Ala Asp Asp Met Gly Ser Gly His His Gly Gly Gly Ala Gly
                115                 120                 125

His Gly Gly Gly Ala Gly His His Val Arg Leu Glu Glu Arg Phe
                130                 135                 140

Ser Asp Asp Gln Leu Val Ser Met Ser Val Arg Glu Leu Asn Arg Gln
145                 150                 155                 160

Leu Arg Gly Phe Ser Lys Glu Val Ile Arg Leu Lys Gln Lys Arg
                165                 170                 175

Arg Thr Leu Lys Asn Arg Gly Tyr Ala Gln Ser Cys Arg Phe Lys Arg
                180                 185                 190

Val Gln Gln Arg His Ile Leu Glu Ser Glu Lys Cys Gln Leu Gln Ser
                195                 200                 205

Gln Val Glu Gln Leu Lys Leu Glu Val Gly Arg Leu Ala Lys Glu Arg
                210                 215                 220

Asp Leu Tyr Lys Glu Lys Tyr Glu Asn Arg Ser Cys Arg Gly His Pro
225                 230                 235                 240

Val Arg His Ala His Pro Ala Ala Lys Pro Gln Leu Gln Val Pro Thr
                245                 250                 255

Ala Val Arg Ile Ser Arg Arg Ala Pro Val Arg Ala Ser Ser Gly Ser
                260                 265                 270

Pro Asp Arg Leu Cys Arg Gly Pro Ser Ala Pro Arg Glu Arg
                275                 280                 285

<210> SEQ ID NO 9
<211> LENGTH: 286
<212> TYPE: PRT
<213> ORGANISM: Gallus gallus

<400> SEQUENCE: 9

Met Ala Ser Glu Leu Ala Met Thr Ala Glu Leu Pro Thr Ser Pro Leu
 1               5                  10                  15

Ala Ile Glu Tyr Val Asn Asp Phe Asp Leu Met Lys Phe Glu Val Lys
                20                  25                  30

Lys Glu Pro Ala Glu Ala Glu Arg Leu Cys His Arg Leu Pro Ala Gly
                35                  40                  45

Ser Leu Ser Ser Thr Pro Leu Ser Thr Pro Cys Ser Ser Val Pro Ser
 50                  55                  60

Ser Pro Ser Phe Cys Ala Pro Ser Pro Gly Gly Gln Pro Ser Ala Gly
 65                  70                  75                  80

Pro Thr Ala Ala Pro Leu Gly Ser Lys Pro Gln Leu Glu Glu Leu Tyr
                85                  90                  95

Trp Met Ser Gly Tyr Gln His His Leu Asn Pro Glu Ala Leu Asn Leu
                100                 105                 110

Thr Pro Glu Asp Ala Val Glu Ala Leu Ile Gly Ala Pro His His His
                115                 120                 125

His His His His Gln Ser Tyr Glu Ser Phe Arg Pro Gln Pro Phe Gly
                130                 135                 140
```

```
Gly Glu Glu Leu Pro Pro Ala Ala His His His Asn Ala His His His
145                 150                 155                 160

His His His His His Leu Arg Leu Glu Glu Arg Phe Ser Asp Asp Gln
                165                 170                 175

Leu Val Ser Met Ser Val Arg Glu Leu Asn Arg Gln Leu Arg Gly Phe
            180                 185                 190

Ser Lys Glu Glu Val Ile Arg Leu Lys Gln Asn Arg Arg Thr Leu Lys
        195                 200                 205

Asn Arg Gly Tyr Ala Gln Ser Cys Arg Tyr Lys Arg Val Gln Gln Arg
    210                 215                 220

His Ile Leu Glu Asn Glu Lys Cys Gln Leu Gln Ser Gln Val Glu Gln
225                 230                 235                 240

Leu Lys Gln Glu Val Ser Arg Leu Ala Lys Glu Arg Asp Leu Tyr Lys
                245                 250                 255

Glu Lys Tyr Glu Lys Leu Ala Ala Arg Gly Phe Pro Arg Glu Pro Ser
            260                 265                 270

Pro Pro Ala Ala Pro Lys Thr Thr Ala Ala Asp Phe Phe Met
        275                 280                 285

<210> SEQ ID NO 10
<211> LENGTH: 286
<212> TYPE: PRT
<213> ORGANISM: Coturnix japonica

<400> SEQUENCE: 10

Met Ala Ser Glu Leu Ala Met Thr Ala Glu Leu Pro Thr Ser Pro Leu
1               5                   10                  15

Ala Ile Glu Tyr Val Asn Asp Phe Asp Leu Met Lys Phe Glu Val Lys
            20                  25                  30

Lys Glu Pro Ala Glu Ala Glu Arg Leu Cys His Arg Leu Pro Ala Gly
        35                  40                  45

Ser Leu Ser Ser Thr Pro Leu Ser Thr Pro Cys Ser Ser Val Pro Ser
    50                  55                  60

Ser Pro Ser Phe Cys Ala Pro Ser Pro Gly Gly Gln Pro Ser Ala Gly
65                  70                  75                  80

Pro Thr Ala Ala Pro Leu Gly Ser Lys Pro Gln Leu Glu Glu Leu Tyr
                85                  90                  95

Trp Met Ser Gly Tyr Gln His His Leu Asn Pro Glu Ala Leu Asn Leu
            100                 105                 110

Thr Pro Glu Asp Ala Val Glu Ala Leu Ile Gly Ala Pro His His His
        115                 120                 125

His His His His Gln Ser Tyr Glu Ser Phe Arg Pro Gln Pro Phe Gly
    130                 135                 140

Gly Glu Glu Leu Pro Pro Ala Ala His His His Asn Ala His His His
145                 150                 155                 160

His His His His His Leu Arg Leu Glu Glu Arg Phe Ser Asp Asp Gln
                165                 170                 175

Leu Val Ser Met Ser Val Arg Glu Leu Asn Arg Gln Leu Arg Gly Phe
            180                 185                 190

Ser Lys Glu Glu Val Ile Arg Leu Lys Gln Lys Arg Arg Thr Leu Lys
        195                 200                 205

Asn Arg Gly Tyr Ala Gln Ser Cys Arg Tyr Lys Arg Val Gln Gln Arg
    210                 215                 220

His Ile Leu Glu Asn Glu Lys Cys Gln Leu Gln Ser Gln Val Glu Gln
225                 230                 235                 240
```

```
Leu Lys Gln Glu Val Ser Arg Leu Ala Lys Glu Arg Asp Leu Tyr Lys
                245                 250                 255

Glu Lys Tyr Glu Lys Leu Ala Ala Arg Gly Phe Pro Arg Glu Thr Ser
            260                 265                 270

Pro Pro Ala Ala Pro Lys Thr Thr Ala Ala Asp Phe Phe Met
            275                 280                 285

<210> SEQ ID NO 11
<211> LENGTH: 315
<212> TYPE: PRT
<213> ORGANISM: Danio rerio

<400> SEQUENCE: 11

Met Ala Thr Asp Leu Ala Met Ser Ala Glu Leu Pro Asn Ser Pro Leu
1               5                   10                  15

Ala Ile Glu Tyr Val Asn Asp Phe Asp Leu Met Lys Phe Glu Ile Lys
            20                  25                  30

Lys Glu Pro Pro Glu Ala Asp Arg Tyr Cys His Arg Leu Pro Pro Gly
        35                  40                  45

Ser Leu Ser Ser Thr Pro Ile Ser Thr Pro Cys Ser Ser Val Pro Ser
50                  55                  60

Ser Pro Ser Phe Cys Ala Pro Ser Pro Gly Ser Gln Pro Gly Gln Asn
65                  70                  75                  80

Leu Val Asn Gly Val Asn Asn Asn Asn Asn Ser Gly Asn Gly Asn
                85                  90                  95

Asn Asn Thr Gln Gly Ser Ser Gly Lys Pro Gln Met Glu Asp Leu Tyr
            100                 105                 110

Trp Ile Pro Asn Tyr Gln His His Ile Ser Pro Glu Ala Leu Asn Leu
        115                 120                 125

Thr Pro Glu Asp Ala Val Glu Ala Leu Ile Gly Asn Ala His His His
130                 135                 140

His His His His His Gln Pro Tyr Lys Gly Phe Arg Gly Gln Gln
145                 150                 155                 160

Tyr Val Gly Lys Asn Leu Ser Ala Ala Thr Asn Gly His His His Pro
                165                 170                 175

Val His His His His His Gly His His Ala His Ala Arg Leu
            180                 185                 190

Glu Asp Arg Phe Ser Asp Glu Gln Leu Val Ser Met Thr Val Arg Glu
        195                 200                 205

Leu Asn Arg Gln Leu Arg Gly Phe Ser Lys Glu Glu Val Ile Arg Leu
210                 215                 220

Lys Gln Lys Arg Arg Thr Leu Lys Asn Arg Gly Tyr Ala Gln Ser Cys
225                 230                 235                 240

Arg Tyr Lys Arg Val Gln Gln Arg His Met Leu Glu Ser Glu Lys Cys
                245                 250                 255

Thr Leu Gln Ser Gln Val Glu Gln Leu Lys Gln Asp Val Ala Arg Leu
            260                 265                 270

Ile Lys Glu Arg Asp Leu Tyr Lys Glu Lys Tyr Glu Lys Leu Ala Ser
        275                 280                 285

Arg Ala Phe Asn Gly Gly Gly Asn Thr Arg Asp Pro Ser Ser Gly Asn
290                 295                 300

His Val Lys Thr Thr Ser Thr Asp Phe Phe Met
305                 310                 315
```

```
<210> SEQ ID NO 12
<211> LENGTH: 42
<212> TYPE: DNA
<213> ORGANISM: Artificial Sequence
<220> FEATURE:
<223> OTHER INFORMATION: Synthetically generated oligonucleotide

<400> SEQUENCE: 12
acgtagcatt ccagctgctg acggtgcagc ctctcccccg ag                    42

<210> SEQ ID NO 13
<211> LENGTH: 42
<212> TYPE: DNA
<213> ORGANISM: Artificial Sequence
<220> FEATURE:
<223> OTHER INFORMATION: Synthetically generated oligonucleotide

<400> SEQUENCE: 13
acgtagcatt ccagctgctg ccggtgcagc ctctcccccg ag                    42

<210> SEQ ID NO 14
<211> LENGTH: 51
<212> TYPE: DNA
<213> ORGANISM: Artificial Sequence
<220> FEATURE:
<223> OTHER INFORMATION: Synthetically generated oligonucleotide

<400> SEQUENCE: 14
tgactggaaa ctgcagcttc agccctctg gaaactgcag cttcagcccc a           51

<210> SEQ ID NO 15
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 15

Ser Asp Asp Gln Leu Val
 1               5

<210> SEQ ID NO 16
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 3, 15, 18
<223> OTHER INFORMATION: n = inosine

<400> SEQUENCE: 16
wsngaygayc arytngtnws                                             20

<210> SEQ ID NO 17
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 17

Leu Tyr Lys Glu Lys Tyr
 1               5

<210> SEQ ID NO 18
```

-continued

```
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 18
<223> OTHER INFORMATION: n = inosine

<400> SEQUENCE: 18
tcrtayttyt cyttrtanar                                               20

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
gatgtcggtg cgggagctga acc                                           23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
cccacctcca gcttcagctg ctc                                           23

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
atggccgcgg agctggcgat g                                             21

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
caggaagaag tcggccgtgc cct                                           23

<210> SEQ ID NO 23
<211> LENGTH: 14
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 5, 6, 7, 8, 9
<223> OTHER INFORMATION: n = a, t, c or g

<400> SEQUENCE: 23
ctgnnnnnnc agcc                                                     14
```

```
<210> SEQ ID NO 24
<211> LENGTH: 12
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 4, 5, 6, 7, 8, 9, 10
<223> OTHER INFORMATION: n = a, t, c, or g

<400> SEQUENCE: 24
tgcnnnnnnn gc                                                            12
```

INSULIN RELATED TRANSCRIPTION FACTOR AND USES THEREOF

CROSS REFERENCE TO RELATED APPLICATIONS

This application claims the benefit of provisional application No. 60/316,453, filed Aug. 31, 2001, the contents of which are incorporated herein by reference in their entirety.

BACKGROUND OF THE INVENTION

In adult mammals, the insulin gene is expressed only in the pancreatic β-cells in the islets of Langerhans. The proximal 5'-flanking region of the insulin promoter has been shown to be sufficient for directing β-cell-specific expression of the insulin gene (Dandoy-Dron et al. (1991) Nucleic Acids Res. 19, 4925-4936; Edlund et al. (1985) Science 30, 912-916; Hanahan (1985) Nature 315, 115-122; Crowe et al. (1989) Mol. Cell. Biol. 9, 1784-1789; Stellrecht et al. (1997) J. Biol. Chem. 272, 3567-3572; Stein (1993) Trends Endocrinol. Metab. 4, 96-100; Sander et al. (1997) J. Mol. Med. 75, 327-340). Further, mutational analysis of the promoter proximal region has identified several cis-acting enhancer elements that are important for insulin expression.

Three conserved insulin enhancer elements, A3 (−201 to −196 bp), E1 (−100 to −91 bp), and RIPE3b/C1-A2 (−126 to −101 bp) play an important role in regulating cell-specific expression of the insulin gene. Transcription factors that bind and activate expression from two of the three conserved insulin enhancer elements (A3 and E1) have been cloned. PDX-1, a member of the homeodomain family of transcription factor expressed in cells of the pancreas and duodenum, binds the A3 element. Heterodimers of ubiquitously distributed basic helix-loop-helix family members (E2A and HEB) and the cell type enriched basic helix-loop-helix member (BETA2) bind the E1 element. A RIPE3b binding activity has been detected in nuclear extracts from both insulin-producing and non-insulin-producing cell lines (Shieh et al. (1991) J. Biol. Chem. 266, 16708-16714; Robinson et al. (1994) *J. Biol. Chem.* 269, 2452-2460; Zhao et al. (2000) J. Biol. Chem. 275, 10532-10537; Shieh et al. (1995) J. Biol. Chem. 270, 21503-21508; Sharma et al. (1995) Mol. Endocrinol. 9, 1468-1476; Sharma et al. (1994) Mol. Cell. Biol. 14, 871-879. Two specific RIPE3b-binding complexes have been identified: 1) a cell-specific complex, RIPE3b1, which is detected only in pancreatic β-cell lines, and 2) the RIPE3b2 complex that is detected in nuclear extracts from all cell lines examined to date.

SUMMARY OF THE INVENTION

The present invention is based, in part, on the discovery, purification and cloning of a novel large Maf family β-cell transcription factor referred to herein as mammalian MafA (mMafA). mMafA is the β-cell specific insulin gene transcription factor RIPE3b1 that binds to the insulin gene enhancer element RIPE3b. It has also been found that the RIPE3b2 factor belongs to the family of small Maf genes. In addition, a related Maf, MafB, has been found to be expressed in insulin producing cells. Thus, Maf family transcription factors are important in the development and differentiation of insulin producing cells and in the regulation of pancreatic beta/endocrine cell function. Maf factors and the regulatory regions of Maf genes can thus be used, inter alia, to select cells that will differentiate into (or are) insulin-producing cells; to identify small molecules that can regulate expression of Maf, e.g., mMafA; to treat and/or develop treatments for type 2 diabetes and/or beta cell dysfunction; to modulate the development, differentiation, function and/or mass of insulin-producing cells; to induce differentiation of precursor cells or stem cells into insulin-producing cells; and to select therapeutic agents that modulate Maf expression, thereby modulating pancreatic beta/endocrine cell development or differentiation and/or insulin production and regulation.

The nucleotide sequence of the cDNA of human mMafA is shown as SEQ ID NO:1 (FIG. 1). The coding sequence of mMafA extends from amino acid 356-1414 of SEQ ID NO:1 (also shown as SEQ ID NO:4, FIG. 2A). The amino acid sequence of the human mMafA polypeptide is shown as SEQ ID NO:2 (FIG. 2B). In addition, the mMafA gene 5' flanking region containing the enhancer-promoter region of mMafA is found at 245231 to 266631 of the mouse supercontig $Mm15_{13}WIFeb01_{13}286$. The coding sequence of mouse mMafA is shown as SEQ ID NO:5, and the predicted amino acid sequence of mouse mMafA is shown as SEQ ID NO:6.

Accordingly, in one aspect, the invention features a nucleic acid molecule that encodes a mammalian MafA (mMafA) protein or polypeptide, e.g., a biologically active portion of the mMafA protein. In one embodiment the isolated nucleic acid molecule encodes a polypeptide having the amino acid sequence of SEQ ID NO:2 or 6. In other embodiments, the invention provides isolated mMafA nucleic acid molecules having the nucleotide sequence shown in SEQ ID NO:1, 3, or 5. In still other embodiments, the invention provides nucleic acid molecules that are substantially identical (e.g., naturally occurring allelic variants) to the nucleotide sequence shown in SEQ ID NO:1, or an alternatively spliced variant thereof, or SEQ ID NO:3. In other embodiments, the invention provides a nucleic acid molecule which hybridizes under a stringency condition described herein to a nucleic acid molecule comprising the nucleotide sequence of SEQ ID NO:1, wherein the nucleic acid encodes a full length mMafA protein, or an active fragment thereof.

In a related aspect, the invention further provides nucleic acid constructs that include a mMafA nucleic acid molecule described herein. In certain embodiments, the nucleic acid molecules are operatively linked to native or heterologous regulatory sequences. In some embodiments, the construct includes a nucleic acid sequence encoding a fragment, e.g., a biologically active or functional fragment, of mMafA linked to a heterologous nucleic acid sequence. For example, the construct can include: the mMafA transcriptional activation domain linked to the DNA binding domain of a heterologous transcription factor or the DNA binding domain of mMafA linked to the transcriptional activation domain of a heterologous transcription factor. Also included are vectors and host cells containing the mMafA nucleic acid molecules of the invention e.g., vectors and host cells suitable for producing mMafA nucleic acid molecules and polypeptides.

In a related aspect, the invention features an isolated nucleotide comprising an mMafA regulatory region, e.g., a promoter or enhancer or other cis-acting element.

In a preferred embodiment, the regulatory region comprises the mMafA 5' flanking sequence or a functional fragment thereof. A functional fragment of the mMafA 5' flanking sequence is a fragment of that has the ability to promote transcription of an operably linked gene compared to a reference or control sequence or a predetermined basal value. Techniques for identifying functional fragments, e.g., specific regulatory domains, within a promoter region are routine in the art once the coding region of a gene has been identified. For example, regulatory regions can be identified and mapped by assaying the ability of specific mutations in a 5' DNA sequence to modulate transcription of an operably linked reporter gene. See, e.g., references 37-51 cited herein, e.g., Carty et al. (1997) J. Biol. Chem. 272:11986-93 (identifying cis- and trans-active factors regulating human islet amyloid polypeptide gene expression in pancreatic beta-cells); and Gerrish et al. (2000) J. Biol. Chem. 275:3485-92 (identifying control regions in the pdx-1 gene).

In a preferred embodiment, the regulatory sequence is coupled to a nucleic acid encoding a heterologous protein, e.g., a reporter molecule as described herein.

In another related aspect, the invention provides nucleic acid fragments suitable as primers or hybridization probes for the detection of mMafA-encoding nucleic acids.

In still another related aspect, isolated nucleic acid molecules that are antisense to a mMafA encoding nucleic acid molecule are provided.

In another aspect, the invention features, mMafA polypeptides, and biologically active or antigenic fragments thereof that are useful, e.g., as reagents or targets in assays applicable to treatment and diagnosis of mMafA-mediated or -related disorders. In another embodiment, the invention provides mMafA polypeptides having a mMafA activity described herein. Preferred polypeptides are mMafA proteins having at least one mMafA activity, e.g., transcriptional activation (e.g., transcriptional enhancer activity), DNA binding activity, basic-leucine zipper (bZIP) protein binding activity (e.g., homodimerization or heterodimerization activity) formation of a coiled-coil structure, nuclear localization, or another mMafA activity as described herein.

In other embodiments, the invention provides mMafA polypeptides, e.g., a mMafA polypeptide having the amino acid sequence shown in SEQ ID NO:2 or 6; an amino acid sequence that is substantially identical to the amino acid sequence shown in SEQ ID NO:2 or 6; or an amino acid sequence encoded by a nucleic acid molecule having a nucleotide sequence which hybridizes under a stringency condition described herein to a nucleic acid molecule comprising the nucleotide sequence of SEQ ID NO:1 or 5 wherein the nucleic acid encodes a full length mMafA protein or an active fragment thereof.

In a related aspect, the invention further provides nucleic acid constructs and host cells, e.g., mammalian, e.g., human host cells, which include a mMafA nucleic acid molecule described herein.

In another aspect, the invention provides an isolated polypeptide that includes an mMafA, or a functional fragment thereof, and a heterologous amino acid sequence, e.g., an mMafA polypeptide or fragment operatively linked to a non-mMafA polypeptide to form a fusion protein. For example, in one embodiment, an artificial transcriptional activator is constructed by using the mMafA DNA binding and dimerization region linked or fused to the transcriptional activation domain from another transcription factor. Such a fusion protein would be capable of turning on gene expression in insulin producing cells. In one embodiment, the DNA-binding and/or dimerization domain of mMafA is linked or fused to the transcriptional activation domain of simplex virus transcriptional regulatory protein (VP16).

In another aspect, the invention features antibodies and antigen-binding fragments thereof, that react with, or more preferably specifically bind mMafA polypeptides or fragments thereof, e.g., the mMafA bZIP domain or the transactivation domain.

In another aspect, the invention features a method of identifying an insulin producing cell or a precursor thereof, e.g., a beta cell or beta cell progenitor. The method includes providing a mammalian (e.g., human) cell, preferably a totipotent, pluripotent or multipotent cell, e.g., an ES cell; determining if the cell expresses a Maf gene; and selecting a cell that expresses a Maf gene. A cell that expresses a Maf gene is identified as an insulin producing cell or a precursor thereof. The method can include correlating the Maf expression with the ability of the selected cell or its descendant to produce insulin. Correlating means identifying the selected cell as an insulin producing cell or a precursor thereof, e.g., providing print material, e.g., informational, marketing or instructional print material related to selected cells or their use, identifying the selected cells as insulin producing cells or precursors thereof. In a preferred embodiment, the method can includes testing the selected cell or a descendant thereof for the ability to produce insulin.

In preferred embodiments, the cell is an adult or embryonic stem cell. In one embodiment, the cell is a stem cell, e.g., an ES cell, expressing an endodermal marker, e.g., hnF3B. The cell is preferably a human cell.

The Maf gene can be a large Maf gene, e.g., mMafA or c-Maf, or a small Maf gene, e.g., MafF, MafG, or MafK. Preferably, the Maf expressed is a mMafA gene, e.g., human MafA.

The determination that the cell expresses a Maf gene can include transfecting the Cell with a construct comprising a mammalian Maf regulatory region operably linked to a nucleotide sequence encoding a reporter polypeptide; evaluating the activity of the reporter polypeptide in the cell; and selecting a cell that exhibits increased reporter activity compared to a reference value, e.g., the level of reporter activity in a control cell, or a predetermined basal value. In a preferred embodiment, the regulatory region comprises a mammalian MafA regulatory region, e.g., a human MafA regulatory region, e.g., a nucleotide sequence comprising a fragment that is capable of increasing transcription. The reporter polypeptide can be any detectable protein, e.g., enzymes detectable by a color signal include fluorescent proteins, e.g., green fluorescent protein (GFP), or blue fluorescent protein; luciferase; chloramphenicol acetyl transferase (CAT); β-galactosidase; β-lactamase; or secreted placental alkaline phosphatase. Other reporter molecules and other enzymes whose function can be detected by appropriate chromogenic or fluorogenic substrates are known to those skilled in the art. An antibiotic resistance gene can also be used.

In another aspect, the invention features a method of providing an insulin producing cell, e.g., by inducing differentiation of precursor cells/stem cells into insulin-producing cells. The method includes: (a) providing a mammalian cell, e.g., a human cell; and (b) inducing the expression of a Maf (e.g., a large Maf, e.g., mMafA or c-Maf, or a small Maf, or a chimeric Maf described herein) in the cell. In a preferred embodiment, the method includes correlating the Maf expression with the ability of the cell or its descendant to produce insulin, e.g., providing print material, e.g., informational, marketing or instructional print material related to induced cells or their use, identifying the cells as insulin producing cells or precursors thereof. In a preferred embodiment, the method includes testing the cell or a descendant thereof for the ability to produce insulin.

In some embodiments, the method also includes the step of inducing the expression of PDX-1, E2A, HEB or BETA2 in the cell. The cell can be a cell type that normally expresses insulin in nature, or a cell type that does not normally express insulin in nature. The cell can be a totipotent, pluripotent or multipotent cell, e.g., an adult or embryonic stem cell. The cell can also be, e.g., a pancreatic cell, an endocrine cell, an enteroendocrine cell, a hepatic cell, a fibroblast, an endothelial cell, a β-cell or a muscle cell. The cell is preferably a secretory cell and preferably a human cell. In some embodiments, the cell includes an exogenous nucleic acid encoding insulin, e.g., human insulin. In one embodiment, the cell is a stem cell expressing an endodermal marker, e.g., hnF3B.

In one embodiment, the induced cell produces insulin in-vitro. In another embodiment, the induced cell produces insulin in vivo. For example, the cell can be transplanted into a subject, e.g., a human or non-human experimental animal. The transplanted cell can be autologous, allogeneic, or xenogeneic. The transplanted cell can thereby act, e.g., to modulate the function and/or mass of insulin-producing cells.

The expression of a Maf gene, e.g., mMafA, MafB, c-Maf, NRL, MafK, MafG, or MafF e.g., human MafA or mouse MafA, can be induced by a number of methods known in the art. In one embodiment, the cell can be genetically engineered to express the full length Maf or a chimeric Maf described herein, e.g., a chimeric Maf gene can be made by transfecting the cell with a nucleotide sequence encoding the DNA binding and/or dimerization region of a first Maf factor, e.g., MafA, MafB, c-Maf, NRL, MafK, MafF or MafG, linked to a sequence encoding a transcriptional activation domain from another factor (e.g., a different Maf protein or another transcription factor, e.g., VP16). In another embodiment, a Maf polypeptide (e.g., MafA) or chimeric Maf polypeptide is itself administered to the cell. In yet another embodiment, expression of a Maf gene is induced by contacting the cell with a small molecule that increases the expression of a Maf gene, e.g., a mMafA gene.

In a preferred embodiment, the cell is genetically engineered to express or misexpress at least one polypeptide that enhances glucose responsiveness, for example, a glucose processing enzyme and/or a receptor. Examples of such polypeptides include hexokinase, glucokinase, GLUT-2, GLP-1, IPI1, PC2, PC3, PAM, glucagon-like peptide I receptor, glucose-dependent insulinotropic polypeptide receptor, BIR, SUR, GHRFR and GHRHR.

In another aspect, the invention features a method of providing an insulin producing cell or a progenitor thereof. The method includes: (a) providing a plurality of mammalian cells, e.g., human cells; (b) inducing the expression of a Maf gene in the cells; and (c) selecting a cell capable of producing insulin from the plurality, to provide an insulin producing cell. In a preferred embodiment, the method includes correlating the Maf expression with the ability of the selected cell or its descendant to produce insulin, e.g., providing print material, e.g., informational, marketing or instructional print material related to induced cells or their use, identifying the cells as insulin producing cells or precursors thereof. In a preferred embodiment, the method includes testing the selected cell or a descendant thereof for the ability to produce insulin. Assays for evaluating insulin production are routine in the art and include, e.g., antibody based insulin detection assays, many of which are commercially available.

In some embodiments, the method also includes the step of inducing the expression of PDX-1, E2A, HEB or BETA2 in the plurality of cells or in the selected cell. The cells can be of a cell type that normally expresses insulin in nature, or of a cell type that does not normally express insulin in nature. The cells can be a totipotent, pluripotent or multipotent cell, e.g., adult or embryonic stem cells. The cell can also be, e.g., pancreatic cells, endocrine cells, enteroendocrine cells, hepatic cells, fibroblasts, endothelial cells, β-cells or muscle cells. The cell is preferably a secretory cell and preferably a human cell. In some embodiments, the cell includes an exogenous nucleic acid encoding insulin, e.g., human insulin. In one embodiment, the cell is a stem cell expressing an endodermal marker, e.g., hnF3B.

In one embodiment, the selected cell produces insulin in-vitro. In another embodiment, the selected cell produces insulin in vivo. For example, the cell can be transplanted into a subject, e.g., a human or non-human experimental animal. The transplanted cell can be autologous, allogeneic, or xenogeneic. The transplanted cell can thereby act, e.g., to modulate the function and/or mass of insulin-producing cells.

The expression of a Maf gene, e.g., mMafA, MafB, c-Maf, NRL, MafK, MafG, or MafF e.g., human MafA or mouse MafA, can be induced by a number of methods known in the art. In one embodiment, the cell can be genetically engineered to express the full length Maf or a chimeric Maf described herein, e.g., a chimeric Maf gene can be made by transfecting the cell with a nucleotide sequence encoding the DNA binding and/or dimerization region of a first Maf factor, e.g., MafA, MafB, c-Maf, NRL, MafK, MafF or MafG, linked to a sequence encoding a transcriptional activation domain from another factor (e.g., a different Maf protein or another transcription factor, e.g., VP16). In another embodiment, a Maf polypeptide (e.g., MafA) or chimeric Maf polypeptide is itself administered to the cell. In yet another embodiment, expression of a Maf gene is induced by contacting the cell with a small molecule that increases the expression of a Maf gene, e.g., a MafA gene.

In a preferred embodiment, the cell is genetically engineered to express or misexpress at least one polypeptide that enhances glucose responsiveness, for example, a glucose processing enzyme and/or a receptor. Examples of such polypeptides include hexokinase, glucokinase, GLUT-2, GLP-1, IPI1, PC2, PC3, PAM, glucagon-like peptide I receptor, glucose-dependent insulinotropic polypeptide receptor, BIR, SUR, GHRFR and GHRHR.

In another aspect, the invention features a method of producing an insulin Responsive cell or evaluating a cell for insulin responsiveness. The method includes providing a cell, e.g., a mammalian cell, e.g., a human cell, e.g., a human neuroendocrine cell, embryonic or adult stem cell, pancreatic ductal cell or cell line, pancreatic acinar cells or cell line, pancreatic endocrine cell or cell line, enteroendocrine cell or cell line, hepatic cell, fibroblast, endothelial cell, β-cell or muscle cell; and transfecting the cell with a nucleic acid containing a Maf regulatory region, e.g., a mMafA, MafB, c-Maf, NRL, MafK, MafG, or MafF regulatory region, e.g., the mMafA 5' flanking sequence or a functional fragment thereof. A functional fragment, e.g., a specific regulatory domain, of the mMafA 5' flanking sequence is a fragment that has the ability to promote transcription of an operably linked gene compared to a reference or control sequence or a predetermined basal value. Methods for identifying specific regulatory domains within a gene sequence are routine in the art. In a preferred embodiment, the mMafA 5' flanking sequence or functional fragment thereof is operably linked to a heterologous nucleic acid sequence, e.g., a reporter gene. These cells can be used, inter alia, to screen for compounds that may modulate insulin synthesis and/or regulation.

In a preferred embodiment, the cell is a mammalian cell, e.g., a human cell.

In a preferred embodiment, the method further includes transfecting the cell with a nucleic acid encoding at least one polypeptide that enhances glucose responsiveness, for example, a glucose processing enzyme and/or a receptor. Examples of such polypeptides include hexokinase; glucokinase; GLUT-2; Glucagon-like Peptide 1 (GLP-1); Insulin Promoter Factor I (IPF1); Proprotein Convertases PC2 and PC3; peptidylglycine alpha-amidating monooxygenase (PAM); glucagon-like peptide I receptor; glucose-dependent insulinotropic polypeptide receptor; β-cell-specific inwardly rectifying potassium channel (BIR), which is involved in release of the secretory granule contents upon glucose stimulation; sulfonylurea receptor (SUR); Growth Hormone Releasing Factor Receptor (GHRFR); Growth Hormone Releasing Hormone Receptor (GHRHR), and ATP-sensitive channel.

In a related aspect, the invention features a method of screening for compounds that regulate insulin synthesis and/or function, e.g., insulin responsiveness, in a cell, tissue, or subject. The method includes: (1) providing a genetically engineered cell, tissue, or subject, e.g., a transgenic animal, e.g., an experimental rodent, having a nucleic acid which encodes a reporter molecule functionally linked to a control region of a Maf gene, e.g., mMafA, e.g., the sequence nucleotides 24523to 255231 of the mouse supercontig $Mm15_{13}WIFeb01_{13}286$ or a functional fragment thereof, (2) contacting the cell, tissue or subject with a test agent; (3) and evaluating a signal produced by the reporter molecule, the presence or strength of which is correlated with the effect of the test agent on the Maf, e.g., mMafA control region. The cell can be a pancreatic β-cell, precursor cell, adult or embryonic stem cell, a human neuroendocrine cell, pancreatic ductal cell or cell line, pancreatic acinar cell or cell line, pancreatic endocrine cell or cell line, enteroendocrine cell or cell line, hepatic cell, fibroblast, endothelial cell, or muscle cell. The cell can be an insulin-expressing or non-insulin expressing cell. In one embodiment, the cell is a stem cell expressing an endodermal marker, e.g., hnF3B.

Examples of reporter molecules, e.g., enzymes detectable by a color signal, include fluorescent proteins, e.g., green fluorescent protein (GFP), or blue fluorescent protein; luciferase; chloramphenicol acetyl transferase (CAT); β-galactosidase; β-lactamase; or secreted placental alkaline phosphatase. Other reporter molecules and other enzymes whose function can be detected by appropriate chromogenic or fluorogenic substrates are known to those skilled in the art.

In a preferred embodiment, the cell, tissue or subject can include a second transgene having a second control sequence from a second gene linked to the same or a different reporter molecule sequence.

In a preferred embodiment, the method further includes administering the test agent to an animal and determining the effect of the test agent on the animal, e.g., determining a parameter of insulin function or beta cell function in the animal.

In another aspect, the invention provides a method of screening for a compound, e.g., a compound that modulates insulin function or β-cell development or differentiation in a subject, e.g., a mammal. The methods include screening for compounds that modulate the expression, level or activity of a Maf protein, e.g., mMafA, MafB, c-Maf, NRL, MafK, MafG, MafF.

In one embodiment, the method includes: providing a Maf protein or nucleic acid, e.g., mMafA, MafB, c-Maf, NRL, MafK, MafG or MafF protein or nucleic acid or a functional fragment thereof; contacting the Maf protein or nucleic acid with a test compound, and determining if the test compound modulates, e.g., binds, the Maf protein or nucleic acid.

In one embodiment, the test compound binds to the Maf protein and modulates a Maf activity. For example, the compound binds to the Maf protein and facilitates or inhibits any of: Maf homo or heterodimerization; Maf DNA binding; Maf transcriptional activation. In a preferred embodiment, the compound is an antibody, e.g., an inhibitory Maf antibody or an antibody that stabilizes or assists Maf binding to DNA or another bZip protein.

In a preferred embodiment, the Maf is MafA, e.g., mMafA, e.g., mouse or human mMafA.

In another embodiment, the test compound binds to a Maf nucleic acid or fragment thereof, e.g., the test compound binds to the Maf promoter region and increases Maf transcription; the test compound binds to a Maf nucleic acid and inhibits transcription of the Maf gene; or the test compound binds to a Maf nucleic acid and inhibits translation of the Maf mRNA. In a preferred embodiment, the compound is a small molecule that binds to the Maf promoter region to modulate transcription.

In another embodiment, the test compound competes with the endogenous Maf protein for binding to a Maf binding partner g., DNA or a bZip protein, thereby inhibiting a Maf activity. For example, the test compound can be a dominant negative Maf protein or nucleic acid or a dominant negative Maf binding partner, e.g., a dominant negative bZip protein. In a preferred embodiment, the compound is a dominant negative Maf protein, e.g., a Maf protein containing a functional DNA binding domain and a non-functional, absent or heterologous transcriptional activation domain, or a Maf protein containing a functional transcriptional activation domain and a non-functional, absent, or heterologous DNA binding domain.

In yet another embodiment, the test compound modulates Maf nuclear localization, e.g., the compound binds to a Maf protein and inhibits or facilitates the passage of the Maf protein through the nuclear pores.

In a preferred embodiment, the test agent is one or more of: a protein or peptide, an antibody, a small molecule, a nucleotide sequence. For example, the agent can be an agent identified through a library screen described herein.

In a preferred embodiment, the contacting step is performed in vitro.

In a preferred embodiment, the method further includes administering the test compound to an experimental animal.

In another preferred embodiment, the contacting step is performed in vivo.

In another embodiment, the method includes: providing a test cell, tissue, or subject; administering a test agent to the cell, tissue, or subject; and determining whether the test agent modulates Maf, e.g., MafA (e.g., mMafA), MafB, c-Maf, NRL, MafK, MafG or MafF expression, level or activity in the cell, tissue, or subject. An agent that is found to modulate Maf in the cell, tissue, or subject is identified as an agent that can modulate β-cell function, β cell mass and/or insulin expression or production in a mammal.

In a preferred embodiment, the cell is a pancreatic β-cell, β-cell precursor cell, adult or embryonic stem cell, a human neuroendocrine cell, pancreatic ductal cell or cell line, pancreatic acinar cell or cell line, pancreatic endocrine cell or cell line, enteroendocrine cell or cell line, hepatic cell, fibroblast, endothelial cell, or muscle cell. The cell can be an insulin-expressing or non-insulin expressing cell. In another preferred embodiment, the tissue is a pancreatic tissue. In a preferred embodiment, the subject is a non-human animal, e.g., an animal model for a pancreatic or insulin related disorder, e.g., a nod mouse, a Zucker rat, a fructose fed rodent, an Israeli sand rat.

In a preferred embodiment, the test cell, tissue, or subject is a wild-type cell, tissue or subject.

In another preferred embodiment, the cell or tissue is from a transgenic mammal described herein, or the subject is a transgenic mammal described herein.

In a preferred embodiment, the method further includes administering the test agent to an animal and determining the effect of the test agent on the animal, e.g., determining a parameter of insulin function or beta cell function in the animal.

The effect of the test agent a Maf in the cell, tissue or subject can be assayed by numerous methods known in the art. For example, Maf interactions with other proteins can be assayed, e.g., by standard immunodetection and protein separation techniques, e.g., using an anti-mMafA antibody described herein. Maf dimerization or binding to other bZip proteins can be detected, e.g., by standard size exclusion, size separation, or immunoprecipitation techniques. Maf subcellular localization can be detected, e.g., using standard immunofluorescence techniques to distinguish cytoplasmic vs. nuclear localization. Maf binding to DNA can be assayed, e.g., by antibody super-shift analysis or by electrophoretic mobility shift analysis (EMSA). To assay for Maf transactivation activity, a construct comprising a nucleotide sequence encoding a Maf, e.g., mMafA responsive regulatory element, e.g., RIPE3b, operably linked to a nucleotide sequence encoding a reporter molecule can be introduced into the test cell, tissue or subject and transcriptional activation activity can be measured using the reporter molecule as a surrogate.

In a preferred embodiment, the subject is further evaluated for one or more of the following parameters of insulin function: (1) insulin metabolism, e.g., insulin responsiveness or resistance; (2) glucose levels; (3) pancreatic β-cell morphology, function or development.

In still another aspect, the invention provides a process for modulating insulin expression and/or production, e.g., modulating the function and/or mass of insulin-producing cells. The process includes modulating a Maf, e.g., MafA (e.g., mMafA), MafB, c-Maf, NRL, MafK, MafG or MafF, polypeptide or nucleic acid expression, levels or activity, e.g. using the screened compounds described herein.

In a preferred embodiment, Maf is modulated ex-vivo, e.g., in a cell or tissue of a subject. In some embodiments, the cell or tissue can be transplanted into a subject. The transplanted cell or tissue can be autologous, allogeneic, or xenogeneic.

In another preferred embodiment, Maf, e.g., MafA, is modulated in vivo in a subject.

In a preferred embodiment, Maf, e.g., MafA, expression, levels, or activity is increased to thereby increase insulin expression or production, e.g., by administering to the subject an agent that increases Maf expression, levels or activity. The agent can be, e.g., Maf polypeptide or a functional fragment or analog thereof, preferably a transcriptionally active Maf polypeptide or a functional fragment or analog thereof, a peptide or protein agonist of Maf that increases the activity, e.g., the transcriptional activity, of a Maf (e.g., by promoting or stabilizing dimerization of Maf or Maf binding to another bZip factor, by increasing nuclear translocation of Maf, by promoting or stabilizing Maf binding to DNA); a small molecule that increases expression of a Maf, e.g., by binding to the promoter region of a Maf gene; an antibody, e.g., an antibody that binds to and stabilizes or assists the binding of a Maf to a Maf binding partner (e.g., another bZip factor, or DNA); or a nucleotide sequence encoding a Maf polypeptide or functional fragment or analog thereof. The nucleotide sequence can be a genomic sequence or a cDNA sequence. The nucleotide sequence can include: a Maf coding region; a promoter sequence, e.g., a promoter sequence from a Maf gene or from another gene; an enhancer sequence; untranslated regulatory sequences, e.g., a 5' untranslated region (UTR), e.g., a 5'UTR from a Maf gene or from another gene, a 3' UTR, e.g., a 3'UTR from a Maf gene or from another gene; a polyadenylation site; an insulator sequence. In another embodiment, the nucleotide sequence includes a Maf functional domain linked to a functional domain from another molecule. For example, the mMafA DNA binding or dimerization domain can be linked to a transcriptional activation domain from another transcription factor (e.g., VP16) or the mMafA transcriptional activation domain can be linked to a DNA binding domain of another transcription factor.

In another preferred embodiment, the level of Maf protein is increased by increasing the level of expression of an endogenous Maf gene, e.g., by increasing transcription of the Maf gene or increasing Maf mRNA stability. In a preferred embodiment, transcription of the Maf gene is increased by: altering the regulatory sequence of the endogenous Maf gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Maf gene to be transcribed more efficiently.

In certain embodiments, the methods involve treatment of conditions related to aberrant activity or expression of the Maf polypeptides or nucleic acids, such as conditions involving aberrant or defective insulin expression or regulation. Such conditions include, e.g., diabetes (e.g., insulin-dependent diabetes mellitus or non insulin-dependent diabetes mellitus) and its associated disorders, e.g., hypertension, retinopathy, persistent hyperinsulinemic hypoglycaemia of infancy (PHHI), insulin resistance, hyperglycemia, glucose intolerance, glucotoxicity.

In another embodiment, Maf expression, levels or activity is decreased to thereby decrease insulin expression or production, e.g., by administering an agent that decreases Maf expression, levels, or activity. Negative regulation of mMafA can be useful to patient with PHHI (persistent hyperinsulinemic hypoglycaemia of infancy) that hypersecrete insulin. Inhibition of mMafA can reduce the insulin content and possibly reduce the hypersecretion. The current treatment for such patients is to perform sub-total pancretactomy.

In a preferred embodiment, the agent can be one or more of: a Maf binding protein, e.g., a soluble Maf binding protein that binds and inhibits a Maf activity, e.g., dimerization activity, nuclear translocation activity, DNA binding activity, or transcriptional activation activity; an antibody that specifically binds to the Maf protein, e.g., an antibody that disrupts a Maf's ability to bind to dimerize, to translocate to the nucleus, or bind DNA; a mutated inactive Maf or fragment thereof which, e.g., binds to a Maf binding partner (e.g., another Maf molecule, bZip protein or DNA) but disrupts a Maf activity, e.g., dimerization, nuclear translocation activity or transcriptional activation activity; a Maf nucleic acid molecule that can bind to a cellular Maf nucleic acid sequence, e.g., mRNA, and inhibit expression of the protein, e.g., an antisense molecule or Maf ribozyme; an agent which decreases Maf gene expression, e.g., a small molecule which binds the promoter of a Maf and decreases Maf gene expression. In another preferred embodiment, a Maf is inhibited by decreasing the level of expression of an endogenous Maf gene, e.g., by decreasing transcription of a Maf gene. In a preferred embodiment, transcription of the Maf gene can be decreased by: altering the regulatory sequences of the endogenous Maf gene, e.g., by the addition of a negative regulatory sequence (such as a DNA-biding site for a transcriptional repressor), or by the removal of a positive regulatory sequence (such as an enhancer or a DNA-binding site for a transcriptional activator). In another preferred embodiment, the antibody which binds mMafA is a monoclonal antibody, e.g., a humanized chimeric or human monoclonal antibody.

In still another aspect, the invention provides a process for modulating cellular development, e.g., modulating the differentiation and/or proliferation of insulin producing cells, e.g., pancreatic β-cells or other cell types with potential to differentiate into insulin producing cells (e.g., embryonic and adult stem cells, pancreatic ductal cells and cell lines, pancreatic acinar cells and cell lines, pancreatic endocrine cells and cell lines, enteroendocrine cells and cell lines, hepatic cells) or cells capable of differentiating into lens cells, e.g., neural retina cell culture neuroretina (NR) cells or neuroectodermal cells. The method includes modulating Maf, e.g., MafA (e.g., mMafA), MafB, c-Maf, NRL, MafK, MafG or MafF polypeptide or nucleic acid expression, levels or activity, e.g. using the screened compounds described herein.

In a preferred embodiment, Maf is modulated in-vitro, e.g., in a cell or tissue of a subject. In some embodiments, the cell or tissue can be transplanted into a subject. The transplanted cell or tissue can be autologous, allogeneic, or xenogeneic.

In another preferred embodiment, Maf is modulated in vivo in a subject.

In a preferred embodiment, Maf expression, levels, or activity is increased, e.g., by administering to the subject an agent that increases Maf activity. The agent can be, e.g., a Maf polypeptide or a functional fragment or analog thereof, preferably a transcriptionally active Maf polypeptide or a functional fragment or analog thereof, a peptide or protein agonist of Maf that increases the activity, e.g., the transcriptional activity, of Maf (e.g., by promoting or stabilizing dimerization of Maf or Maf binding to another bZip factor, by increasing nuclear translocation of Maf, by promoting or stabilizing Maf binding to DNA); a small molecule that increases expression of Maf, e.g., by binding to the promoter region of the Maf gene; an antibody, e.g., an antibody that binds to and stabilizes or assists the binding of Maf to a Maf binding partner (e.g., another bZip factor, or DNA); or a nucleotide sequence encoding a Maf polypeptide or functional fragment or analog thereof. The nucleotide sequence can be a genomic sequence or a cDNA sequence. The nucleotide sequence can include: a Maf coding region; a promoter sequence, e.g., a promoter sequence from a Maf gene or from another gene; an enhancer sequence; untranslated regulatory sequences, e.g., a 5' untranslated region (UTR), e.g., a 5'UTR from a Maf gene or from another gene, a 3' UTR, e.g., a 3'UTR from a Maf gene or from another gene; a polyadenylation site; an insulator sequence. In another embodiment, the nucleotide sequence includes a Maf functional domain linked to a functional domain from another molecule. For example, the Maf DNA binding or dimerization domain can be linked to a transcriptional activation domain from another transcription factor (e.g., VP16) or the Maf transcriptional activation domain can be linked to a DNA binding domain of another transcription factor.

In another preferred embodiment, the level of Maf protein is increased by increasing the level of expression of an endogenous Maf gene, e.g., by increasing transcription of the Maf gene or increasing Maf mRNA stability. In a preferred embodiment, transcription of the Maf gene is increased by: altering the regulatory sequence of the endogenous Maf gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Maf gene to be transcribed more efficiently.

In certain embodiments, the methods involve treatment of conditions related to aberrant activity or expression of the mMafA polypeptides or nucleic acids, such as conditions involving aberrant or defective pancreatic β-cell development, differentiation or function. Such conditions include, e.g., diabetes (e.g., insulin-dependent diabetes mellitus or non insulin-dependent diabetes mellitus) and its associated disorders, e.g., hypertension, retinopathy, persistent hyperinsulinemic hypoglycaemia of infancy (PHHI), insulin resistance, hyperglycemia, glucose intolerance, glucotoxicity.

In another embodiment, Maf expression, levels or activity is decreased, e.g., by administering an agent that decreases Maf expression, levels, or activity. In a preferred embodiment, the agent can be one or more of: a Maf binding protein, e.g., a soluble Maf binding protein that binds and inhibits a Maf activity, e.g., dimerization activity, nuclear translocation activity, DNA binding activity, or transcriptional activation activity; an antibody that specifically binds to the Maf protein, e.g., an antibody that disrupts Maf's ability to bind to dimerize, to translocate to the nucleus, or bind DNA; a mutated inactive Maf or fragment thereof which, e.g., binds to a Maf binding partner (e.g., another Maf molecule, bZip protein or DNA) but disrupts a Maf activity, e.g., dimerization, nuclear translocation activity or transcriptional activation activity; a Maf nucleic acid molecule that can bind to a cellular Maf nucleic acid sequence, e.g., mRNA, and inhibit expression of the protein, e.g., an antisense molecule or Maf ribozyme; an agent which decreases Maf gene expression, e.g., a small molecule which binds the promoter of a Maf and decreases Maf gene expression. In another preferred embodiment, Maf is inhibited by decreasing the level of expression of an endogenous Maf gene, e.g., by decreasing transcription of the Maf gene. In a preferred embodiment, transcription of the Maf gene can be decreased by: altering the regulatory sequences of the endogenous Maf gene, e.g., by the addition of a negative regulatory sequence (such as a DNA-biding site for a transcriptional repressor), or by the removal of a positive regulatory sequence (such as an enhancer or a DNA-binding site for a transcriptional activator). In another preferred embodiment, the antibody which binds mMafA is a monoclonal antibody, e.g., a humanized chimeric or human monoclonal antibody.

In another aspect, the invention provides a method of determining if a subject is at risk for or has a disorder, e.g., an insulin related disorder. The method includes: (a) evaluating the level, activity or expression of a Maf, e.g., MafA (e.g., mMafA), MafB, c-Maf, NRL, MafK, MafG or Maf, in a subject, e.g., in a biological sample of the subject, and (b) correlating an altered, e.g., increased, level of Maf levels, activity or expression with a risk for or presence of an insulin related disorder. In a preferred embodiment, the method includes determining the activity of or the presence or absence of Maf, e.g., MafA, nucleic acid molecules and/or polypeptides or in a biological sample. Such methods are useful, e.g., for diagnosis of pancreatic disorders or insulin related disorders, e.g., for diagnosis of diabetes or diabetes risk. Aberrant or deficient Maf expression, levels or activity is indicative of risk for the disorder or the presence of the disorder in the subject. The subject is preferably a human.

In a preferred embodiment, the method includes one or more of the following:
    detecting, in a tissue of the subject, the presence or absence of a mutation that affects the expression of a Maf gene, or detecting the presence or absence of a mutation in a region which controls the expression of the gene, e.g., a mutation in the 5' control region;

detecting, in a tissue of the subject, the presence or absence of a mutation that alters the structure or expression of a Maf gene, wherein the presence of a mutation is indicative of risk;

detecting, in a tissue of the subject, the misexpression of a Maf gene, at the mRNA level, e.g., detecting a non-wild type level of a mRNA, e.g., wherein non-wild type levels of Maf mRNA is associated with risk;

detecting, in a tissue of the subject, the misexpression of the Maf gene, at the protein level, e.g., detecting a non-wild type level of a Maf polypeptide, wherein decreased or increased levels of Maf protein (e.g., compared to a control) is indicative of a risk.

In preferred embodiments the method includes: ascertaining the existence of at least one of: a deletion of one or more nucleotides from the Maf gene; an insertion of one or more nucleotides into the gene; a point mutation, e.g., a substitution of one or more nucleotides of the gene; a gross chromosomal rearrangement of the gene, e.g., a translocation, inversion, duplication or deletion.

For example, detecting the genetic lesion can include: (i) providing a probe/primer, e.g., a labeled probe/primer, which includes a region of nucleotide sequence which hybridizes to a sense or antisense sequence from the Maf gene, or naturally occurring mutants thereof, or to the 5' or 3' flanking sequences naturally associated with the Maf gene; (ii) exposing the probe/primer to nucleic acid of the tissue; and detecting, by hybridization, e.g., in situ hybridization, of the probe/primer to the nucleic acid, the presence or absence of the genetic lesion.

In a preferred embodiment, detecting the misexpression includes ascertaining the existence of at least one of: an alteration in the level of a messenger RNA transcript of the Maf gene, e.g., as compared to levels in a subject not at risk for an insulin related disorder; the presence of a non-wild type splicing pattern of a messenger RNA transcript of the gene; or a non-wild type level of the Maf protein e.g., as compared to levels in a subject not at risk for an insulin related disorder.

Methods of the invention can be used prenatally or to determine if a subject's offspring will be at risk for a disorder.

In a preferred embodiment, the method includes determining the structure of a Maf gene, an abnormal structure being indicative of risk for the disorder.

In a preferred embodiment, the method includes contacting a sample from the subject with an antibody to the Maf protein or a nucleic acid, which hybridizes specifically with a portion of the gene.

In another aspect, the invention features a method of treating a subject. The method includes modulating the expression, level, or activity of a Maf protein, e.g., MafA (e.g., mMafA), MafB, c-Maf, NRL, MafK, MafG or MafF, in a cell (e.g., a pancreatic β-cell, β-cell precursor cell, adult or embryonic stem cell, a human neuroendocrine cell, pancreatic ductal cell or cell line, pancreatic acinar cell or cell line, pancreatic endocrine cell or cell line, enteroendocrine cell or cell line, hepatic cell, fibroblast, endothelial cell, muscle cell or dedifferentiated duct or exocrine cell) or tissue (e.g., pancreas) of the subject. The cell or tissue can be an insulin expressing or non-insulin expressing cell or tissue. The subject can be a human or a non-human animal, e.g., an animal model for an insulin related disorder, e.g., a nod mouse, a Zucker rat, a fructose fed rodent, an Israeli sand rat. In a preferred embodiment, the subject is identified as having or being at risk for an insulin related disorder or pancreatic β-cell dysfunction, e.g., diabetes (e.g., insulin-dependent diabetes mellitus or non insulin-dependent diabetes mellitus) or its associated disorders, e.g., hypertension, retinopathy, persistent hyperinsulinemic hypoglycaemia of infancy (PHHI), insulin resistance, hyperglycemia, glucose intolerance, glucotoxicity. The level of the Maf protein can be modulated by modulating any of: Maf expression (e.g., modulating rate of transcription or mRNA stability), protein levels, or protein activity.

In a preferred embodiment, the Maf is modulated in-vitro, e.g., in a cell or tissue of a subject. In some embodiments, the cell or tissue can be transplanted into a subject. The transplanted cell or tissue can be autologous, allogeneic, or xenogeneic.

In another preferred embodiment, the Maf is modulated in vivo in a subject.

In a preferred embodiment, Maf activity, level or expression is increased, e.g., by administering to the subject an agent that increases Maf activity, level or expression. Increasing Maf expression, levels or activity can, e.g., increase the production of insulin in a subject in need of increased insulin production (e.g., a diabetic subject); or regulate pancreatic β-cell differentiation and/or proliferation in a subject in need of regulating pancreatic β-cell differentiation and/or proliferation (e.g., a subject with β-cell dysfunction). The agent can be, e.g., a Maf polypeptide or a functional fragment or analog thereof, preferably a transcriptionally active Maf polypeptide or a functional fragment or analog thereof; a peptide or protein agonist of Maf that increases the activity, e.g., the transcriptional activity, of Maf (e.g., by promoting or stabilizing dimerization of Maf or Maf binding to another bZip factor, by increasing nuclear translocation of Maf, by promoting or stabilizing Maf binding to DNA); a small molecule that increases expression of a Maf, e.g., by binding to the promoter region of the Maf gene; an antibody, e.g., an antibody that binds to and stabilizes or assists the binding of Maf to a Maf binding partner (e.g., another bZip factor, or DNA); or a nucleotide sequence encoding a Maf polypeptide or functional fragment or analog thereof. The nucleotide sequence can be a genomic sequence or a cDNA sequence. The nucleotide sequence can include: a Maf coding region; a promoter sequence, e.g., a promoter sequence from a Maf gene or from another gene; an enhancer sequence; untranslated regulatory sequences, e.g., a 5' untranslated region (UTR), e.g., a 5'UTR from a Maf gene or from another gene, a 3' UTR, e.g., a 3'UTR from a Maf gene or from another gene; a polyadenylation site; an insulator sequence. In another embodiment, the nucleotide sequence includes a Maf functional domain linked to a functional domain from a heterologous molecule. In a preferred embodiment, a Maf, e.g., mMafA, DNA binding or dimerization domain can be linked to a transcriptional activation domain from another transcription factor (e.g., another Maf or VP16). In another preferred embodiment, a Maf, e.g., mMafA, transcriptional activation domain can be linked to a DNA binding domain of another transcription factor (e.g., another Maf or another transcription factor).

In another preferred embodiment, the level of Maf protein is increased by increasing the level of expression of an endogenous Maf gene, e.g., by increasing transcription of the Maf gene or increasing Maf mRNA stability. In a preferred embodiment, transcription of the Maf gene is increased by: altering the regulatory sequence of the endogenous Maf gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Maf gene to be transcribed more efficiently.

In some embodiments, Maf expression, levels or activity is increased in conjunction with another treatment, e.g., administration of insulin.

In another preferred embodiment, Maf can be decreased by administering to the subject an agent that inhibits Maf gene expression, mRNA stability, protein production levels and/or activity. Decreasing Maf expression, levels or activity can, e.g., decrease insulin production in a subject with aberrantly high levels of insulin. An agent that inhibits Maf can be one or more of: a Maf binding protein, e.g., a soluble Maf binding protein that binds and inhibits a Maf activity, e.g., DNA binding or transcription activation activity, or inhibits the ability of a Maf to interact with a binding partner, e.g., another bZip motif containing molecule; an antibody that specifically binds to the Maf protein, e.g., an antibody that disrupts a Maf s ability to bind to a binding partner; a mutated inactive Maf or fragment thereof which binds to a Maf but disrupts a Maf activity, e.g., a Maf fragment that is able to bind DNA but lacks or has a deficient transactivation domain; a Maf nucleic acid molecule that can bind to a cellular Maf nucleic acid sequence, e.g., mRNA, and inhibit expression of the protein, e.g., an antisense molecule or Maf ribozyme; an agent which decreases Maf gene expression, e.g., a small molecule which binds the promoter of Maf. In another preferred embodiment, Maf is inhibited by decreasing the level of expression of an endogenous Maf gene, e.g., by decreasing transcription of the Maf gene. In a preferred embodiment, transcription of the Maf gene can be decreased by: altering the regulatory sequences of the endogenous Maf gene, e.g., by the addition of a negative regulatory sequence (such as a DNA-biding site for a transcriptional repressor), or by the removal of a positive regulatory sequence (such as an enhancer or a DNA-binding site for a transcriptional activator). In another preferred embodiment, the antibody which binds the Maf is a monoclonal antibody, e.g., a humanized chimeric or human monoclonal antibody.

In yet another aspect, the invention features a method of treating a subject, e.g., a subject having an insulin related disorder. The method includes: (a) providing a mammalian cell, e.g., a human cell; inducing expression of a Maf protein, or functional fragment thereof, in the cell (e.g., a mammalian Maf, e.g., mMafA, e.g., human MafA); and transplanting the cell or its descendants into a subject in need of treatment for an insulin related disorder. The cell can be a pancreatic β-cell, β-cell precursor cell, adult or embryonic stem cell, a human neuroendocrine cell, pancreatic ductal cell or cell line, pancreatic acinar cell or cell line, pancreatic endocrine cell or cell line, enteroendocrine cell or cell line, hepatic cell, fibroblast, endothelial cell, muscle cell or dedifferentiated duct or exocrine cell. The cell can be autologous, allogeneic or xenogeneic, but is preferably allogeneic or autologous.

In a preferred embodiment, the cell is an adult or embryonic stem cell.

In a preferred embodiment, the cell is genetically engineered to express a Maf protein, e.g., a mammalian large Maf, e.g., mMafA (e.g., human MafA), or c-Maf, or a small Maf, e.g., a small Maf described herein. The Maf protein can be a full length Maf or a functional fragment thereof, e.g., the Maf protein can be a chimeric Maf described herein. In a preferred embodiment, the cell is also genetically engineered to express one or more of: PDX-1, E2A, HEB or BETA2.

In another aspect, the invention features a method of treating a subject, e.g., a subject in need of treatment for an insulin related disorder. The method includes: providing a population of cells, e.g., mammalian cells, e.g., human cells, genetically engineered to express a Maf protein or functional fragment thereof, selecting from the population a cell that expresses insulin; and transplanting the selected cell or its descendants into a subject in need of treatment for an insulin related disorder. The cells can be pancreatic β-cells, β-cell precursor cells, adult or embryonic stem cells, human neuroendocrine cells, pancreatic ductal cells or a cell line, pancreatic acinar cells or a cell line, pancreatic endocrine cells or a cell line, enteroendocrine cells or a cell line, hepatic cells, fibroblasts, endothelial cells, muscle cells or dedifferentiated duct or exocrine cells. The cells can be autologous, allogeneic or xenogeneic, but is preferably allogeneic or autologous.

In a preferred embodiment, the method includes culturing the insulin expressing cell under conditions that allow the differentiation of the cell into pancreatic islets. The cells can be differentiated into pancratic islet cells or tissue in vitro or in vivo. In a preferred embodiment, the cells are differentiated in vitro and then implanted into the subject.

In a further aspect, the invention provides methods for evaluating the efficacy of a treatment of a disorder, e.g., an insulin or pancreatic β-cell disorder, e.g., diabetes (e.g., insulin-dependent diabetes mellitus or non insulin-dependent diabetes mellitus) and its associated disorders, e.g., hypertension, retinopathy, persistent hyperinsulinemic hypoglycaemia of infancy (PHHI), insulin resistance, hyperglycemia, glucose intolerance, glucotoxicity. The method includes: treating a subject, e.g., a patient or an animal, with a protocol under evaluation (e.g., treating a subject with one or more of a compound identified using the methods described herein); and evaluating the expression or activity of a Maf (e.g., MafA (e.g., mMafA), MafB, c-Maf, NRL, MafK, MafG or MafF) nucleic acid or polypeptide before and after treatment. A change, e.g., a decrease or increase, in the level of a Maf nucleic acid (e.g., mRNA) or polypeptide or activity (e.g., transcriptional activation activity) after treatment, relative to the level of expression before treatment, is indicative of the efficacy of the treatment of the disorder.

In a preferred embodiment, the subject is also treated with, e.g., insulin or glucose, before and/or after the subject is treated with the protocol under evaluation. The level of mMafA nucleic acid or polypeptide expression or activity can be detected by any method described herein.

In a preferred embodiment, the evaluating step includes obtaining a sample (e.g., a tissue sample, e.g., a biopsy, or a fluid (e.g., blood) sample) from the subject, before and after treatment and comparing the level of expressing of a Maf nucleic acid (e.g., mRNA), polypeptide, or activity before and after treatment. In another aspect, the invention provides methods for evaluating the efficacy of a therapeutic or prophylactic agent. The method includes: contacting a sample with an agent (e.g., a compound identified using the methods described herein, a cytotoxic agent); and evaluating the expression of Maf nucleic acid or polypeptide in the sample before and after the contacting step. A change, e.g., a decrease or increase, in the level of the Maf nucleic acid (e.g., mRNA) or polypeptide in the sample obtained after the contacting step, relative to the level of expression in the sample before the contacting step, is indicative of the efficacy of the agent. The level of Maf nucleic acid or polypeptide expression can be detected by any method described herein.

In a preferred embodiment, the sample is from pancreatic tissue.

In a preferred embodiment, the sample is a pancreatic β-cell sample.

In another aspect, the invention features a cell which is genetically engineered to express, e.g., constitutively express, transiently express, or overexpress, mMafA or a functional fragment thereof, e.g., a fragment having DNA binding activity, dimerization activity, or transcriptional activation activity. The cell can be a cell type that normally expresses insulin in nature, or a cell type that does not normally express insulin in nature.

In a preferred embodiment, mMafA is linked or fused to a heterologous polypeptide, e.g., the cell is genetically engineered to constitutively express, transiently express, or overexpress a mMafA fusion protein as described herein.

In a preferred embodiment, the cell is a secretory cell, pancreatic β-cell, β-cell precursor cell, adult or embryonic stem cell, a human neuroendocrine cell, pancreatic ductal cell or cell line, pancreatic acinar cell or cell line, pancreatic endocrine cell or cell line, enteroendocrine cell or cell line, hepatic cell, fibroblast, endothelial cell, or muscle cell, a secretory cell, a pancreatic β-cell precursor cell or a pancreatic β-cell or duct cell or dedifferentiated duct or exocrine cell. In one embodiment, the cell is a stem cell expressing an endodermal marker, e.g., hnF3B.

In a preferred embodiment, the cell is genetically engineered to express or misexpress at least one polypeptide that enhances glucose responsiveness, for example, a glucose processing enzyme and/or a receptor. Examples of such polypeptides include hexokinase, glucokinase, GLUT-2, GLP-1, IPI1, PC2, PC3, PAM, glucagon-like peptide I receptor, glucose-dependent insulinotropic polypeptide receptor, BIR, SUR, GHRFR and GHRHR.

In a preferred embodiment, the cell is a secretory cell that includes a nucleic acid encoding insulin, e.g., human insulin.

In a related aspect, the invention features a method of producing insulin in or by a cell, e.g., a stem cell, a pancreatic precursor cell, a P cell. The method includes modulating the expression, level or activity of a Maf protein, e.g., MafA (e.g., mMafA), MafB, c-Maf, NRL, MafK, MafG or MafF, or a functional fragment thereof, in the cell. Maf expression, level or activity can be modulated, e.g., by administering to the cell an agent described herein that increases or decreases a Maf protein expression, level, or activity. The cell can be a cell type that normally expresses insulin in nature, or a cell type that does not normally express insulin in nature. In some embodiments, the method also includes the step of inducing the expression of PDX-1, E2A, HEB or BETA2 in the cell.

In a preferred embodiment, the cell is a pancreatic β-cell, β-cell precursor cell, adult or embryonic stem cell, a human neuroendocrine cell, pancreatic ductal cell or cell line, pancreatic acinar cell or cell line, pancreatic endocrine cell or cell line, enteroendocrine cell or cell line, hepatic cell, fibroblast, endothelial cell, muscle cell, or dedifferentiated duct or exocrine cell. The cell can be glucose responsive or non-glucose responsive. In the case of a non-glucose responsive cell, glucose responsiveness can be reconstituted by genetically engineering the cell to express at least one polypeptide that enhances glucose responsiveness, for example, a glucose processing enzyme and/or a receptor. Examples of such polypeptides include hexokinase, glucokinase, GLUT-2, GLP-1, IPI1, PC2, PC3, PAM, glucagon-like peptide I receptor, glucose-dependent insulinotropic polypeptide receptor, BIR, SUR, GHRFR and GHRHR. In a preferred embodiment, the cell is a secretory cell that includes a nucleic acid encoding human insulin.

In a preferred embodiment, the cell is not transfected.

In a preferred embodiment, the cell is transiently transfected or stably transfected, e.g., with a nucleic acid sequence that enhances glucose responsiveness as described above.

In a preferred embodiment, the agent is a Maf nucleic acid or fragment thereof (e.g., a MafA (e.g., mMafA), MafB, c-Maf, NRL, MafK, MafG or MafF). In one embodiment, the agent is a nucleic acid encoding a full length Maf. In another embodiment, the agent is a nucleic acid encoding a Maf fusion protein, e.g., a nucleic acid encoding the DNA binding domain of one Maf protein and the transcriptional activation domain of a heterologous transcription factor, e.g., another Maf or a different transcription factor. In another embodiment, the agent is a nucleic acid encoding a functional fragment of a Maf protein, e.g., a DNA binding domain of a Maf protein, e.g., MafA (e.g., mMafA), MafB, c-Maf, NRL, MafK, MafG or MafF.

In a preferred embodiment, insulin is produced in the cell in vitro.

In another preferred embodiment, insulin is produced in a cell in vivo.

In a preferred embodiment, the method further includes the step of introducing (e.g., transplanting) the cell into a subject, e.g., for the treatment of an insulin or β-cell related disorder, e.g., diabetes (e.g., insulin-dependent diabetes mellitus or non insulin-dependent diabetes mellitus) and its associated disorders, e.g., hypertension, retinopathy, persistent hyperinsulinemic hypoglycaemia of infancy (PHHI), insulin resistance, hyperglycemia, glucose intolerance, glucotoxicity. The transplanted cell or tissue can be autologous, allogeneic, or xenogeneic.

In another preferred embodiment, mMafA is modulated in vivo in a subject.

In some embodiments, the method can further include harvesting the insulin from the cell. The method can optionally include administering the harvested insulin to a subject, e.g., a human or non-human animal.

In another aspect, the invention features a transgenic non-human mammal, e.g., a primate, a rodent, e.g., a rat, mouse, or guinea pig, that contains a transgene, e.g., a mMafA transgene. In one embodiment, the non-human transgenic mammal has a genome being heterozygous or homozygous for an engineered disruption in a MafA gene, wherein the mammal has disrupted insulin function, e.g., the transgenic animal misexpresses mMafA, e.g., overexpresses, underexpresses, or is null for mMafA. An mMafA transgene refers to an exogenous mMafA nucleic acid (e.g., a mMafA cDNA, gene or fragment thereof) that is inserted into the animal. The nucleic acid is inserted into the genome of the animal, e.g., in the chromosomal DNA of the animal or in an episome, plasmid, or other non-chromosomal DNA element. In another embodiment, the mMafA gene is misexpressed in a tissue specific manner, e.g., the mMafA gene is misexpressed in pancreatic ductal cells and not misexpressed in a non pancreatic tissue.

In a first embodiment, the transgenic animal has a disruption in an mMafA gene wherein the disruption causes a reduction in mMafA expression, levels or activity. The disruption in the mMafA gene can be a deletion, addition, or substitution. In a preferred embodiment, the transgenic animal is a mMafA knockout. In another embodiment, the disruption is a disruption that decreases the level of expression of an endogenous mMafA gene, e.g., by decreasing transcription of the mMafA gene. In another preferred embodiment, the transgenic animal contains a transgene that decreases transcription of the endogenous mMafA gene, e.g., by the addition of a negative regulatory sequence (such as a DNA-biding site for a transcriptional repressor), or by the removal of a positive regulatory sequence (such as an enhancer or a DNA-binding site for a transcriptional activator).

The transgenic animal displays one or more of the following phenotypes: (1) it has decreased mMafA compared to a wild-type animal; (2) it has decreased insulin expression compared to a wild-type animal; (3) it has aberrant pancreatic cell function compared to a wild-type mammal; (4) it has a histologically abnormal pancreas compared to a wild-type animal; (5) it exhibits decreased ability to metabolize glucose compared to a wild-type mammal (e.g., it exhibits glucotoxicity). The transgenic animals are useful, e.g., as models for insulin related or pancreatic β-cell related disorders described herein. The transgenic animals are also useful as test subjects in the screening assays described herein In a preferred embodiment, the disruption is homozygous.

In another preferred embodiment, the disruption is heterozygous.

In a second embodiment, the transgenic animal overexpresses mMafA compared to a wild-type animal. In one embodiment, the animal expresses a heterologous mMafA nucleic acid in addition to its endogenous mMafA gene. In another embodiment, mMafA is overexpressed by increasing the level of expression of an endogenous mMafA gene, e.g., by increasing transcription of the mMafA gene or increasing mMafA mRNA stability. In a preferred embodiment, the transgenic animal contains a transgene that increases transcription of the transgenic animal's endogenous mMafA gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the mMafA gene to be transcribed more efficiently or in a regulated fashion (e.g., through use of a Tet on/off system).

The transgenic animal displays one or more of the following phenotypes: (1) it has increased mMafA compared to a wild-type animal; (2) it has increased insulin expression compared to a wild-type animal; (3) it has aberrant pancreatic cell function compared to a wild-type mammal; (4) it has a histologically abnormal pancreas compared to a wild-type animal; (5) it exhibits increased ability to metabolize glucose compared to a wild-type mammal. The transgenic animals are useful, e.g., as models for insulin related or pancreatic β-cell related disorders described herein. The transgenic animals are also useful as test subjects in the screening assays described herein.

In another preferred embodiment, the transgenic animal, e.g., rodent, expresses mMafA or a functional fragment thereof.

In another aspect, the invention features a method of evaluating a subject. The method includes: determining the sequence of at least one nucleotide within the mMafA gene, or flanking the mMafA gene (e.g., within 10, 100, 1000, 3000, 50000, 10,0000, or more base pairs of the gene); and comparing the determined sequence with a reference sequence.

In a preferred embodiment, the subject is at risk for an insulin or β-cell related disorder, e.g., β-cell dysfunction, diabetes (e.g., insulin-dependent diabetes mellitus or non insulin-dependent diabetes mellitus) and its associated disorders, e.g., hypertension, retinopathy, persistent hyperinsulinemic hypoglycaemia of infancy (PHHI), insulin resistance, hyperglycemia, glucose intolerance, glucotoxicity.

In a preferred embodiment, a difference between the determined sequence and the reference sequence indicates a difference in the subject's response to a therapeutic agent.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a mMafA molecule. In one embodiment, the capture probe is a nucleic acid, e.g., a probe complementary to a mMafA nucleic acid sequence or a nucleic acid, e.g., a DNA that the mMafA specifically binds. In another embodiment, the capture probe is a polypeptide, e.g., an antibody specific for mMafA polypeptides or a bZip protein. Also featured is a method of analyzing a sample by contacting the sample to the aforementioned array and detecting binding of the sample to the array.

Other features and advantages of the invention will be apparent from the following detailed description, and from the claims.

DESCRIPTION OF THE DRAWINGS

FIGS. 1A-B. The human mMafA cDNA sequence (SEQ ID NO:1). The coding sequence of human mMafA starts at nucleotide 356 (the start site ATG is underlined) and ends at nucleotide 1414 (including the stop codon) of SEQ ID NO:1.

FIG. 2. (A) human mMafA coding sequence (SEQ ID NO:4); (B) human mMafA amino acid sequence (SEQ ID NO:2); (C) diagram of the predicted domains of mMafA. The predicted transcriptional activation domain extends from about amino acid 1-75 of SEQ ID NO:2. Two glycine rich regions are present from about amino acids 75-106 and 207-227 of SEQ ID NO:2. (These glycine rich regions are not present in the avian MafA homologue). The DNA binding domain extends from about amino acid 227-281 of SEQ ID NO:2 and includes a basic region present from about amino acid 253-281 of SEQ ID NO:2 and an extended homology region (HER) present from about amino acid 227-253. A dimerization (leucine zipper) domain is present from about amino acid 281-316 of SEQ ID NO:2.

FIG. 3 shows the affinity purification of mMafA: 47-kDa protein constitutes the RIPE3b1 factor. A) Small aliquots from affinity purification fractions were incubated with $^{32}P$ radiolabelled rat insulin II-139 to -101 bp probe and binding activity was analyzed by EMSA. Asterisks denote fractions containing the RIPE3b1 factor and HP denotes partially purified heparin-pooled fraction used as the starting material for the affinity purification. Positions of RIPE3b and A2 binding complexes are shown FIG. 4 shows an SDS-PAGE analysis of purified mMafA: To determine the degree of purification, the concentrated and pooled purified fractions (0.4 µg, Lane 3) were run on a 10% SDS-PAGE gel along with the starting HIT T-15 nuclear extract (4.0 µg, Lane 1) and HP fraction (0.8 µg, Lane 2) and Silver stained. The positions and molecular weights (x$10^3$ Da) of protein standards are indicated; the arrow marks the position of the 47-kDa band.

FIG. 5. Verification of DNA binding activity of the purified RIPE3b1 factor: The 47-kDa protein band was eluted using SDS-PAGE fractionation; the eluted protein and HP fraction were analyzed for binding to –139 to –101 bp probe. Binding reactions were performed in the absence (–) or presence of 50-fold excess of the indicated competitors. Positions of the various binding complexes are shown.

FIGS. 6A-C. The RIPE3b1 factor is mammalian MafA. A) Ethidium bromide agarose gel electrophoretic analysis of PCR products amplified using cDNAs from insulin-producing (HIT T-15 and MIN-6) and glucagon-producing (aTC 1.6) cell lines. Degenerate oligonucleotide primers corresponding to peptide sequences of 47-kDa protein selectively amplify a PCR product (arrows) from cDNAs from insulin-producing cells. Gel electrophoretic analysis of PCR products amplified using internal primers and cyclophilin primers demonstrates that mMafA is expressed only in insulin-producing cells. HIT T-15 nuclear extract was incubated with radiolabelled RIPE3b probe (B) in the absence or presence of 50-fold excess of indicated unlabelled aA-crystallin wild type or mutant aA-crystallin competitors, or rat insulin II oligonucleotides; and C) in the absence or presence of ac-Maf, aNucleolin, or aPDX-1 antibodies. Binding reactions were analyzed by EMSA, and the positions of the RIPE3b1 and RIPE3b2 complexes are indicated. Wild type aA-Crystallin competitor successfully competed for both the RIPE3b1 and RIPE3b2 binding activities. However, ac-Maf antibody that detects only "large Maf" family members only recognized the RIPE3b1 complex.

FIGS. 7A-C. 7A-B show an amino acid sequence alignment performed with sequence alignment program MegAlign using ClustalW method with BLOSUM matrix (Lasergene) between (a) human mMafA sequence (hMafA) (SEQ ID NO:2); (b) mouse MafA sequence identified by cloning by RT-PCR from mouse insulinoma cell line MIN-6 and mouse islet RNAs and PCR from mouse genomic DNA followed by sequencing (mouse MafA As-data) (SEQ ID NO:7); (c) mouse MafA sequence identified by analyzing for the homology to the human MafA sequence in the mouse genome database—WGS super contig (m.MafA MGD AS-Analy) (SEQ ID NO:6); (d) MafA homologous gene as annotated and presented in the mouse genome database (m.MafA MGD) (SEQ ID NO:8) (the annotation was done by the public mouse genome database, while the sequence MafA MGD AS-Analy, was identified by the present inventors' analysis); (e) Chicken L-Maf (SEQ ID NO:9); (f) Quail MafA (SEQ ID NO:10); and (g) Zebra fish Smaf1 (SEQ ID NO:11). 7C is a phylogenetic tree and sequence identity/divergence determined from the alignment in FIGS. 7A-B. The results shows that the human and mouse MafA are more closely related to each other than the avian MafA/L-Maf, suggesting that mammalian MafA represents a distinct sub-species of MafA factors. Also, the mouse MafA sequence determined by the mouse genome database (m.MafA MGD) is significantly different than the experimentally identified mouse MafA sequence (mouse MafA As-data) or identified by us after analyzing the sequences in the public mouse genome database (m.MafA MGD AS-Analy) (see 7A-B).

FIG. 8. mMafA mRNA is expressed in insulin-producing cells. A) Total RNA from the indicated samples was run on an agarose-formaldehyde gel and stained with ethidium bromide to show 18S and 28S rRNA bands. B) Northern blot of the gel shown in A, hybridized with a hMafA probe (15 h exposure). C) A mouse Multiple Tissue Northern blot (Ambion, Austin, Tex.) containing 2 μg poly(A) RNA from 10 tissues hybridized to the same probe (72 h exposure). Arrows denote the positions of 1.9 and 2.8 Kb transcripts.

FIG. 9. hMafA can bind the RIPE3b element and activate insulin gene expression. A) HIT T-15 nuclear extract and lysates from indicated in vitro transcription-translation reactions were incubated with RIPE3b probe in the absence (−) or presence of indicated unlabelled wild-type RIPE3b oligonucleotide or one with mutations at positions −122 and 121 bp as competitor. In addition, binding reactions were also incubated with an αHSV.tag antibody. EMSA was performed as described before with minor modifications; the gels were run for an additional 30 minutes to resolve binding complexes. Position of the RIPE3b1 complex is denoted by an asterisk (*), and the positions of hMafA, ΔN-hMafA and heterodimer (HD) complexes are indicated. B) Equal volume of in vitro transcribed and translated lysates from hMafA, ΔN-hMafA or pETBlue-2 vector were run on 10% SDS-PAGE gel, expression of specific proteins were determined by immuno- blotting with αHSV-tag monoclonal antibody (Novagen, Madison, Wis.) and bands were detected by ECL kit (Amersham, Piscataway, N.J.). Positions and molecular weights (×$10^3$ Da) of protein standards are indicated. C) Non-insulin producing HeLa cells were transfected with luciferase reporter plasmid (−238 WT LUC or −122.121 m LUC) (24) and indicated expression plasmid (hMafA, ΔN-hMafA or pcDNA3.1). Luciferase activity was determined 48 h after transfection. Results are presented relative to −238 WT luciferase activity +/−S.E. (n=4), after normalization for internal control. HeLa cells were transfected with rat insulin I:GFP reporter (−410 rINSI:GFP) and indicated expression plasmids. 48 h after transfection, HeLa cells were fixed with 10% buffered formalin, and fusion proteins were detected using αHSV.tag monoclonal antibody and a secondary Texas Red conjugated anti mouse antibody. Expression of both hMafA and ΔN-hMafA were localized to the nuclei of the transfected cells. However only hMafA was able to activate GFP expression from the insulin reporter construct.

FIG. 10. mMafA is the endogenous constituent of the RIPE3b1 complex. HIT T-15 nuclear extract was incubated with the −139 to −101 bp rat insulin II probe in the absence or presence of indicated cold competitors, anti c-Maf, preimmune and anti mMafA specific antibodies. The position of various DNA binding complexes is shown. Antibodies against the "large-Maf" factors (anti cMaf antibody Santa Cruz Biotechnology, CA, Catalog #7866) and a mMafA specific antibody raised against a mMafA specific peptide (YEAFRGPGFAGGGGADDM amino acid 163-180) can selectively prevent the formation of the RIPE3b1 complex. These observations demonstrate that the endogenous factor present in the HIT T-15 nuclear extract that constitutes the RIPE3b1 complex is the mMafA.

FIG. 11. RIPE3b2 complex is formed by transcription factors belonging to the "small-Maf" family. HIT T-15 nuclear extract was incubated with the −139 to −101 bp rat insulin II probe in the absence or presence of indicated cold competitors, anti c-Maf and anti MafF/G/K antibodies (Santa Cruz Biotechnology, CA, Catalog # sc-7866 and sc-16278, respectively). The formation of RIPE3b2 complex was selectively prevented by "small-Maf" specific antibody (anti MafF/G/K) but not by the antibody that recognizes "large-Maf" factors (anti cMaf antibody). These observations demonstrate that the endogenous factor present in the HIT T-15 nuclear extract that constitutes the RIPE3b2 complex is a "small-Maf" family member.

FIGS. 12A-B. Mouse mMafA coding sequence (SEQ ID NO:5)was identified by the inventors by analysis of the mouse genome database based on homology to human MafA coding sequence (MafA MGD AS-Analy). The sequence was confirmed by PCR amplification and sequencing of the complete coding sequence from mouse genomic DNA and total RNA from mouse insulin producing cell line MIN6 and mouse pancreatic islet (mouse MafA AS-data). FIG. 12 shows the nucleotide sequence of mouse MafA MGD AS-Analy. This sequence predicts a protein having a sequence over 98% identical with experimentally identified sequence (mouse MafA AS-data) and less than 80% identical to the protein predicted by the annotated mouse genomic database (see FIG. 13). FIG. 12 also includes the information on the mouse WGS super contig containing the mMafA MGD AS-Analy sequence and the position of this sequence in the contig. The portion of mouse WGS super contig that contains the sequence of mMafA, and its regulatory regions, e.g., promoter, enhancer, and other cis action regions sequence, e.g., 10 Kb of sequence 5' and 3' to the coding sequence, corresponds to bp 245231 to 2666310 of the mouse supercontig Mm15_WIFeb01_286.

FIG. 13. Nucleotide sequence of the mouse MafA MGD (SEQ ID NO:3),as annotated in the publicly available mouse sequence database. This sequence is annotated based on combining the sequence of predicted exons. The annotated sequence predicts a protein only 79.8% identical to the protein predicted by analysis of the experimentally identified mouse mMafA coding sequence shown in FIG. 12 (see also FIG. 7C).

DETAILED DESCRIPTION

Figure 6A:
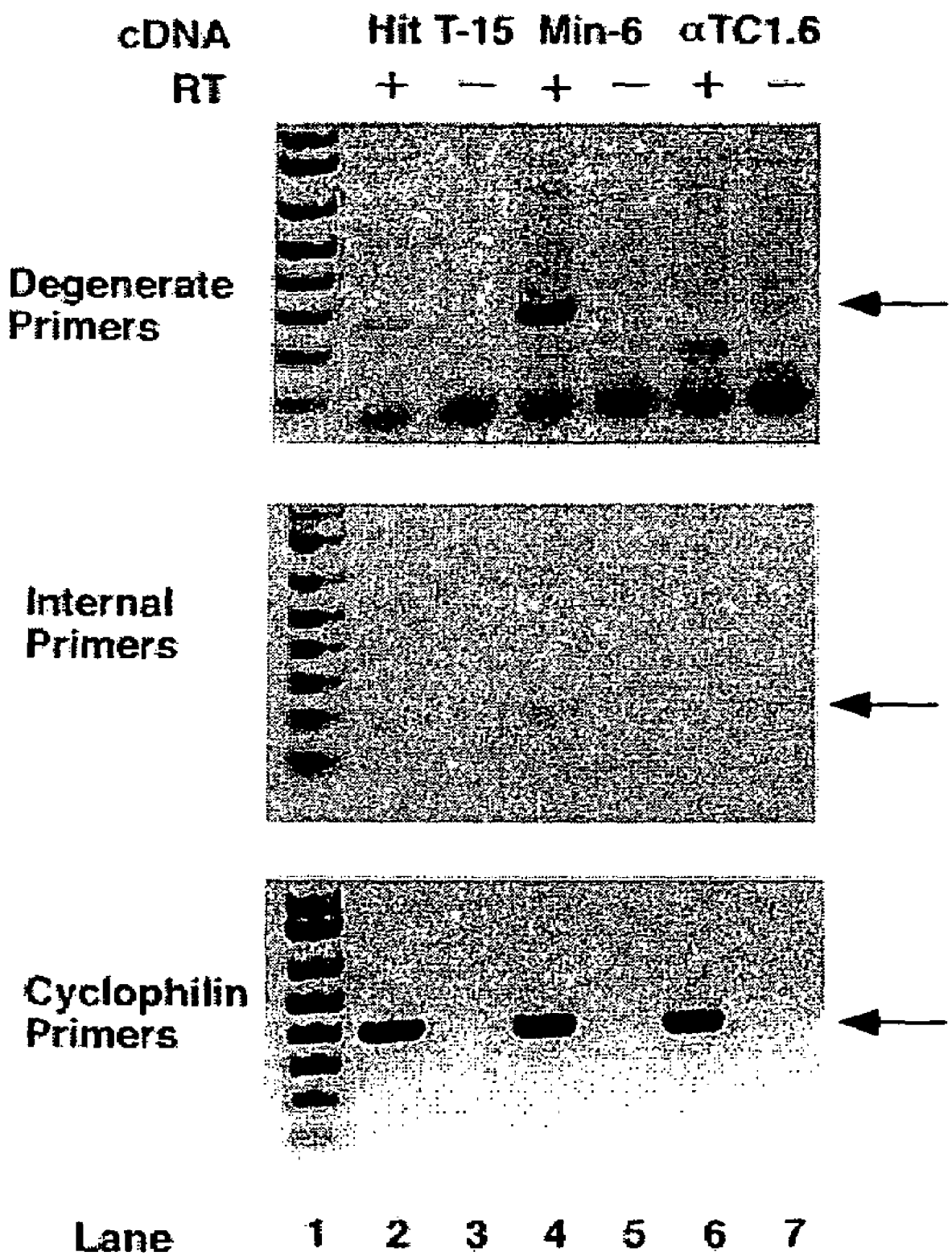

The human mMafA coding sequence which is approximately 1059 nucleotides long (see SEQ ID NO:1) codes for a 352 amino acid protein (SEQ ID NO:2). Human mMafA contains the following regions or other structural features: a transcriptional activation domain from about amino acid 1-75 of SEQ ID NO:2; two glycine rich regions from about amino acid 75-106 and 207-227 of SEQ ID NO:2; a basic region from about amino acid 253 to 281 of SEQ ID NO:2; a leucine zipper domain (dimerization region) from about amino acid 281316 of SEQ ID NO:2; a DNA binding domain from about amino acid 227-281 of SEQ ID NO:2.

The mMafA protein is a member of the broad family of Maf transcription factors. The term "family" when referring to the protein and nucleic acid molecules of the invention means two or more proteins or nucleic acid molecules having a common structural domain or motif. Maf transcription factors are characterized by a basic region-leucine zipper (bZip) motif and a N-terminal transcription activating motif. Maf proteins may be subdivided into large Mafs, which can be between 200-400 amino acids (e.g., MafA/L-Maf, Maf-c) and small Mafs (e.g., MafK, MafF, and MafG), which can be between 140 -170 amino acids and lack the N-terminal activation domain. mMafA is believed to be the mammalian homologue of avian MafA/L-Maf (described, e.g., in Ogino and Yasuda (1998) Science 280: 115-118; Benkelifa et. al (1998) Oncogene 17:247-254). Some Maf family members have been implicated in lens differentiation and are expressed, e.g., in retina (Ogino and Yasuda (1998) Science 280: 115-118, Benkhelifa et al. (2001) Mol. Cell Biol. 21:4441-4452, Ring et. al.(2000) Development 127307-317; Kim et. al. (1999) PNAS 96:3781-3785).

mMafA described herein is unlike other known Mafs in that it is expressed primarily in insulin expressing cells. In addition, the inventors have used human and mouse MafB (sequence available in GenBank) to amplify by PCR a MafB cDNA from hamster insulinoma cell line HIT T-15 and Mouse insulinoma cell line MIN-6. MafB is known to have a broad cellular distribution (Wang et. al. Genomics 59: 275-281). Additionally, RIPE3b2 factor recognizes MafA/L-Maf binding site in alpha A-crystallin promoter with the same binding specificity as the RIPE3b1 factor (suggesting that it belongs to same family). Yet, anti cMaf antibody that can recognize other large Maf family member only recognizes RIPE3b1 and not RIPE3b2, suggesting that RIPE3b2 is a small Maf transcription factor. Therefore, Maf family transcription factors play an important role in regulation of insulin expression.

As Maf factors have very conserved DNA binding and protein dimerization domains (Blank and Andrews TIBS 22:947, Matsishima-Hibiya et. al. BBRC 245:412-418; Dlakic et. al. EMBO 20:828-840) they can bind to sites recognized by other family members. Therefore, an artificial transcriptional activator can be made by using DNA binding and/or dimerization region of a Maf factor, e.g., MafA, MafB, c-Maf, NRL, MafK, MafF or MafG, linked to a transcriptional activation domain from another factor (e.g., a different Maf protein or another transcription factor, e.g., VP16). Such chimeric factors can be capable of turning on gene expression in insulin producing cells, thereby producing insulin expressing cells, e.g., for transplantation.

mMafAs described herein can be naturally or non-naturally occurring and can be from either the same or different species. For example, the mMafA subfamily can contain a first protein of human origin as well as other distinct proteins of human origin, or alternatively, can contain homologues of non-human mammalian origin, e.g., rat or mouse proteins. Members of the mMafA family can also have common functional characteristics.

To identify the presence of a functional domain, e.g., a bZip DNA binding domain or transcriptional activation domain, in a mMafA protein sequence, and make the determination that a polypeptide or protein of interest has a particular profile, the amino acid sequence of the protein can be searched against the Pfam database of HMMs (e.g., the Pfam database, release 2.1) using the default parameters sanger.ac.uk/Software/Pfam/Hmm$_{13}$search). For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al.(1990) *Meth. Enzymol.* 183:146-159; Gribskov et al.(1987) *Proc. Natl. Acad. Sci. USA* 84:4355-4358; Krogh et al.(1994) *J. Mol. Biol.* 235:1501-1531; and Stultz et al. (1993) *Protein Sci.* 2:305-314, the contents of which are incorporated herein by reference.

mMafA is expressed primarily in insulin producing cells. As the mMafA polypeptides of the invention can modulate insulin-related activities, they may be useful for developing novel diagnostic and therapeutic agents for insulin-related disorders, e.g., β-cell or insulin related disorder, e.g., diabetes (e.g., insulin-dependent diabetes mellitus or non insulin-dependent diabetes mellitus) and its associated disorders, e.g., hypertension, retinopathy, persistent hyperinsulinemic hypoglycaemia of infancy (PHHI), insulin resistance, hyperglycemia, glucose intolerance, glucotoxicity.

As used herein, a "mMafA activity", "biological activity of mMafA" or "functional activity of mMafA", refers to an activity exerted by a mMafA protein, polypeptide or nucleic acid molecule. For example, a mMafA activity can be an activity exerted by mMafA in a mMafA-responsive cell or tissue, e.g., an insulin producing cell or tissue. A mMafA activity can be determined in vivo or in vitro. In one embodiment, a mMafA activity is a direct activity, such as an association with a mMafA binding partner, e.g., another protein, e.g., a bZip protein, or DNA. A "target molecule" or "binding partner" is a molecule with which a mMafA protein binds or interacts in nature. A mMafA activity can also be an indirect activity, e.g., a cellular signaling activity mediated by interaction of the mMafA protein with a mMafA receptor. Therefore, the mMafA proteins of the present invention can have one or more of the following activities: (1) homo-dimerization; (2) dimerization with another bZip containing protein; (3) DNA binding, e.g., RIPE 3b enhancer element binding; (4) transcriptional activation, e.g., transcriptional activation of the insulin gene; (5) modulation of gene expression, e.g., insulin expression; (6) modulation of pancreatic β-cell function, development and/or differentiation.

The mMafA mRNA is selectively expressed in insulin producing cells. Thus, the mMafA molecules can act as novel diagnostic targets and therapeutic agents for controlling pancreatic or insulin related disorders or conditions. Examples of such disorders include diabetes (e.g., insulin-dependent diabetes mellitus or non insulin-dependent diabetes mellitus) and its associated disorders, e.g., hypertension, retinopathy, persistent hyperinsulinemic hypoglycaemia of infancy (PHHI), insulin resistance, hyperglycemia, glucose intolerance, glucotoxicity, β-cell dysfunction.

The mMafA protein, fragments thereof, and derivatives and other variants of the sequence in SEQ ID NO:2 or 6 are collectively referred to as "polypeptides or proteins of the invention" or "mMafA polypeptides or proteins". Nucleic acid molecules encoding such polypeptides or proteins are collectively referred to as "nucleic acids of the invention" or "mMafA nucleic acids." mMafA molecules refer to mMafA nucleic acids, polypeptides, and antibodies.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, but preferably is double-stranded DNA.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

Preferably, an isolated nucleic acid molecule of the invention that hybridizes under a stringency condition described herein to the sequence of SEQ ID NO:1 or SEQ ID NO:4, corresponds to a naturally-occurring nucleic acid molecule.

As used herein, a "naturally-occurring" nucleic acid molecule refers to an RNA or DNA molecule having a nucleotide sequence that occurs in nature. For example a naturally occurring nucleic acid molecule can encode a natural protein.

As used herein, the terms "gene" and "recombinant gene" refer to nucleic acid molecules which include at least an open reading frame encoding a mMafA protein. The gene can optionally further include non-coding sequences, e.g., regulatory sequences and introns. Preferably, a gene encodes a mammalian mMafA protein or derivative thereof.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that a preparation of mMafA protein is at least 10% pure. In a preferred embodiment, the preparation of mMafA protein has less than about 30%, 20%, 10% and more preferably 5% (by dry weight), of non-mMafA protein (also referred to herein as a "contaminating protein"), or of chemical precursors or non-mMafA chemicals. When the mMafA protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of mMafA without abolishing or substantially altering a mMafA activity. Preferably the alteration does not substantially alter the mMafA activity, e.g., the activity is at least 20%, 40%, 60%, 70% or 80% of wild-type. An "essential" amino acid residue is a residue that, when altered from the wild-type sequence of mMafA, results in abolishing a mMafA activity such that less than 20% of the wild-type activity is present. For example, conserved amino acid residues in mMafA are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a mMafA protein is preferably replaced with another amino acid residue from the same side chain family. Alternatively, in another embodiment, mutations can be introduced randomly along all or part of a mMafA coding sequence, such as by saturation mutagenesis, and the resultant mutants can be screened for mMafA biological activity to identify mutants that retain activity. Following mutagenesis of SEQ ID NO:1, the encoded protein can be expressed recombinantly and the activity of the protein can be determined.

As used herein, a "biologically active portion" of a mMafA protein includes a fragment of a mMafA protein which participates in an interaction, e.g., an intramolecular or an inter-molecular interaction. An inter-molecular interaction can be a specific binding interaction or an enzymatic interaction (e.g., the interaction can be transient and a covalent bond is formed or broken). An inter-molecular interaction can be between a mMafA molecule and a non-mMafA molecule or between a first mMafA molecule and a second and/or third mMafA molecule (e.g., a dimer or trimer interaction). Biologically active portions of a mMafA protein include peptides comprising amino acid sequences sufficiently homologous to or derived from the amino acid sequence of the mMafA protein, e.g., the amino acid sequence shown in SEQ ID NO:2 or 6, which include less amino acids than the full length mMafA proteins, and exhibit at least one activity of a mMafA protein. Typically, biologically active portions comprise a domain or motif with at least one activity of the mMafA protein, e.g., DNA binding or transactivation. A biologically active portion of a mMafA protein can be a polypeptide which is, for example, 10, 25, 50, 100, 200 or more amino acids in length. Biologically active portions of a mMafA protein can be used as targets for developing agents which modulate a mMafA mediated activity, e.g., insulin production.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453 ) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to mMafA nucleic acid molecules of the invention. BLAST protein searches can be performed with the XBLAST program, score=50, wordlength=3 to obtain amino acid sequences homologous to mMafA protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See ncbi.nlm.nih.gov.

Particularly preferred mMafA polypeptides of the present invention have an amino acid sequence substantially identical to the amino acid sequence of SEQ ID NO:2 or 6. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 80%, 85%, 90%. 91%, 92%, 93%, 94%, 95%, 96%, 97%, 98%, 98.5% or 99% identity to SEQ ID NO:2 or 6 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity to SEQ ID NO:1 or 3 are termed substantially identical.

"Misexpression or aberrant expression", as used herein, refers to a non-wild-type pattern of gene expression at the RNA or protein level. It includes: expression at non-wild type levels, i.e., over- or under-expression; a pattern of expression that differs from wild type in terms of the time or stage at which the gene is expressed, e.g., increased or decreased expression (as compared with wild type) at a predetermined developmental period or stage; a pattern of expression that differs from wild type in terms of altered, e.g., increased or decreased, expression (as compared with wild type) in a predetermined cell type or tissue type; a pattern of expression that differs from wild type in terms of the splicing size, translated amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

As used herein, "stem cells" are cells that have the ability to divide for indefinite periods in culture and to give rise to specialized cells. A "totipotent" stem cell can give rise to all types of cells in an organism. For example, a fertilized egg is a totitpotent cell. "Pluripotent" stem cells are capable of giving rise to most, but not all, tissues of an organism. For example, the inner cell mass cells of a blastocyst are pluripotent. "Multipotent" stem cells are stem cells that are committed to give rise to cells of a particular lineage. Examples of multipotent cells include blood stem cells which give rise to red blood cells, white blood cells and platelets; and skin stem cells that give rise to the various types of skin cells. While totipotent and pluripotent stem cells are primarily found in embryos (e.g., ES cells), multipotent stem cells are also found in children and adults.

Various aspects of the invention are described in further detail below.

Isolated Nucleic Acid Molecules

In one aspect, the invention provides, an isolated or purified, nucleic acid molecule that encodes a mMafA polypeptide described herein, e.g., a full-length mMafA protein or a fragment thereof, e.g., a biologically active portion of mMafA protein. Also included is a nucleic acid fragment suitable for use as a hybridization probe, which can be used, e.g., to identify a nucleic acid molecule encoding a polypeptide of the invention, mMafA mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of these nucleotide sequences. In one embodiment, the nucleic acid molecule includes sequences encoding the human mMafA protein (i.e., "the coding region" of SEQ ID NO:1, and alternatively spliced variants thereof), as well as 5' untranslated sequences (e.g., nucleotides 245231 to 255231 of the mouse supercontig Mm15$_{13}$WIFeb01$_{13}$ or a fragment thereof). Alternatively, the nucleic acid molecule can include only the coding region of SEQ ID NO:1 and, e.g., no flanking sequences which normally accompany the subject sequence.

In another embodiment, an isolated nucleic acid molecule of the invention includes a nucleic acid molecule which is a complement of the nucleotide sequence shown in SEQ ID NO:1 or SEQ ID NO:4, or a portion of any of these nucleotide sequences. In other embodiments, the nucleic acid molecule of the invention is sufficiently complementary to the nucleotide sequence shown in SEQ ID NO:1 or SEQ ID NO:4, such that it can hybridize (e.g., under a stringency condition described herein) to the nucleotide sequence shown in SEQ ID NO:1 or 4, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO: 1 or SEQ ID NO:3, or a portion, preferably of the same length, of any of these nucleotide sequences.

mMafA Nucleic Acid Fragments

A nucleic acid molecule of the invention can include only a portion of the nucleic acid sequence of SEQ ID NO:1 or 3 or 5. For example, such a nucleic acid molecule can include a fragment which can be used as a probe or primer or a fragment encoding a portion of a mMafA protein, e.g., an immunogenic or biologically active portion of a mMafA protein. A fragment can comprise those nucleotides of SEQ ID NO:1 or 5, which encode a bZip domain of human mMafA. The nucleotide sequence determined from the cloning of the mMafA gene allows for the generation of probes and primers designed for use in identifying and/or cloning other mMafA family members, or fragments thereof, as well as mMafA homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 50 amino acids in length. Fragments also include nucleic acid sequences corresponding to specific amino acid sequences described above or fragments thereof. Nucleic acid fragments should not be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a mMafA nucleic acid fragment can include a sequence corresponding to a bZip domain or a transactivation domain.

MMafA probes and primers are provided. Typically a probe/primer is an isolated or purified oligonucleotide. The oligonucleotide typically includes a region of nucleotide sequence that hybridizes under a stringency condition described herein to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3 or SEQ ID NO:5, or of a naturally occurring allelic variant or mutant of SEQ ID NO:1 or SEQ ID NO:3 or SEQ ID NO:5. Preferably, an oligonucleotide is less than about 200, 150, 120, or 100 nucleotides in length.

In one embodiment, the probe or primer is attached to a solid support, e.g., a solid support described herein.

One exemplary kit of primers includes a forward primer that anneals to the coding strand and a reverse primer that anneals to the non-coding strand. The forward primer can anneal to the start codon, e.g., the nucleic acid sequence encoding amino acid residue 1 of SEQ ID NO:2 or 5. The reverse primer can anneal to the ultimate codon, e.g., the codon immediately before the stop codon. In a preferred embodiment, the annealing temperatures of the forward and reverse primers differ by no more than 5, 4, 3, or 2° C.

In a preferred embodiment the nucleic acid is a probe which is at least 10, 12, 15, 18, 20 and less than 200, more preferably less than 100, or less than 50, nucleotides in length. It should be identical, or differ by 1, or 2, or less than 5 or 10 nucleotides, from a sequence disclosed herein. If alignment is needed for this comparison the sequences should be aligned for maximum homology. "Looped" out sequences from deletions or insertions, or mismatches, are considered differences.

A probe or primer can be derived from the sense or antisense strand of a nucleic acid which encodes, e.g., a bZip domain of SEQ ID NO:2 or 6.

In another embodiment a set of primers is provided, e.g., primers suitable for use in a PCR, which can be used to amplify a selected region of a mMafA sequence, e.g., a domain, region, site or other sequence described herein. The primers should be at least 5, 10, or 50 base pairs in length and less than 100, or less than 200, base pairs in length. The primers should be identical, or differs by one base from a sequence disclosed herein or from a naturally occurring variant. For example, primers suitable for amplifying all or a portion of any of the following regions are provided: a bZip domain, a transactivation domain as shown in SEQ ID NO:2 or 6.

A nucleic acid fragment can encode an epitope bearing region of a polypeptide described herein.

A nucleic acid fragment encoding a "biologically active portion of a mMafA polypeptide" can be prepared by isolating a portion of the nucleotide sequence of SEQ ID NO:1 or 3, or 5, which encodes a polypeptide having a mMafA biological activity (e.g., the biological activities of the mMafA proteins are described herein), expressing the encoded portion of the mMafA protein (e.g., by recombinant expression in vitro) and assessing the activity of the encoded portion of the mMafA protein. For example, a nucleic acid fragment encoding a biologically active portion of mMafA includes a bZip domain, a DNA binding domain or a transactivation domain. A nucleic acid fragment encoding a biologically active portion of a mMafA polypeptide, may comprise a nucleotide sequence which is greater than 300 or more nucleotides in length.

In preferred embodiments, a nucleic acid includes a nucleotide sequence which is about 300, 400, 500, 600, 700, 800, 900, 1000, 1100, 1200, 1300 or more nucleotides in length and hybridizes under a stringency condition described herein to a nucleic acid molecule of SEQ ID NO:1, 3 or 5.

mMafA Nucleic Acid Variants

The invention further encompasses nucleic acid molecules that differ from the nucleotide sequence shown in SEQ ID NO:1, 3 or 5. Such differences can be due to degeneracy of the genetic code (and result in a nucleic acid which encodes the same mMafA proteins as those encoded by the nucleotide sequence disclosed herein). In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2 or 6. If alignment is needed for this comparison the sequences should be aligned for maximum homology. The encoded protein can differ by no more than 5, 4, 3, 2, or 1 amino acid. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in E. Coli, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or 3, e.g., as follows: by at least one but less than 10, 20, 30, or 40 nucleotides; at least one but less than 1%, 5%, 10% or 20% of the nucleotides in the subject nucleic acid. The nucleic acid can differ by no more than 5, 4, 3, 2, or 1 nucleotide. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70-75%, more typically at least about 80-85%, and most typically at least about 90-95% or more identical to the amino acid sequence shown in SEQ ID NO:2 or 6 or a fragment of this sequence. Such nucleic acid molecules can readily be identified as being able to hybridize under a stringency condition described herein, to the nucleotide sequence encoding the sequence shown in SEQ ID NO 2 or 6 or a fragment of the sequence. Nucleic acid molecules corresponding to orthologs, homologs, and allelic variants of the mMafA cDNAs of the invention can further be isolated by mapping to the same chromosome or locus as the mMafA gene.

Preferred variants include those that are correlated with DNA binding or transactivating activity.

Allelic variants of mMafA, e.g., human mMafA, include both functional and nonfunctional proteins. Functional allelic variants are naturally occurring amino acid sequence variants of the mMafA protein within a population that maintain the ability bind DNA or increase transcription of a responsive gene. Functional allelic variants will typically contain only conservative substitution of one or more amino acids of SEQ ID NO:2 or 6, or substitution, deletion or insertion of non-critical residues in non-critical regions of the protein. Non-functional allelic variants are naturally-occurring amino acid sequence variants of the mMafA, e.g., human mMafA, protein within a population that do not have the ability to bind DNA or transactivate a responsive gene. Non-functional allelic variants will typically contain a non-conservative substitution, a deletion, or insertion, or premature truncation of the amino acid sequence of SEQ ID NO:2 or 6, or a substitution, insertion, or deletion in critical residues or critical regions of the protein.

Moreover, nucleic acid molecules encoding other mMafA family members and, thus, which have a nucleotide sequence which differs from the mMafA sequences of SEQ ID NO:1 or SEQ ID NO:3 are intended to be within the scope of the invention.

Antisense Nucleic Acid Molecules, Ribozymes and Modified mMafA Nucleic Acid Molecules In another aspect, the invention features, an isolated nucleic acid molecule which is antisense to mMafA. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire mMafA coding strand, or to only a portion thereof. In another embodiment, the antisense nucleic acid molecule is antisense to a "noncoding region" of the coding strand of a nucleotide sequence encoding mMafA (e.g., the 5' and 3' untranslated regions).

An antisense nucleic acid can be designed such that it is complementary to the entire coding region of mMafA mRNA, but more preferably is an oligonucleotide which is antisense to only a portion of the coding or noncoding region of mMafA mRNA. For example, the antisense oligonucleotide can be complementary to the region surrounding the translation start site of mMafA mRNA, e.g., between the –10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a mMafA protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. A ribozyme having specificity for a mMafA-encoding nucleic acid can include one or more sequences complementary to the nucleotide sequence of a mMafA nucleic acid disclosed herein (i.e., SEQ ID NO:1 or SEQ ID NO:3), and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a mMafA-encoding mRNA. See, e.g., Cech et al. U.S. Pat. No. 4,987,071; and Cech et al. U.S. Pat. No. 5,116,742. Alternatively, mMafA mRNA can be used to select a catalytic RNA having a specific ribonuclease activity from a pool of RNA molecules. See, e.g., Bartel, D. and Szostak, J. W. (1993) *Science* 261:1411-1418.

MMafA gene expression can be inhibited by targeting nucleotide sequences complementary to the regulatory region of the mMafA (e.g., the mMafA promoter and/or enhancers) to form triple helical structures that prevent transcription of the mMafA gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A mMafA nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of mMafA nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of mMafA nucleic acid molecules can also be used in the analysis of single base pair mutations in a gene, (e.g., by PNA-directed PCR clamping); as 'artificial restriction enzymes' when used in combination with other enzymes, (e.g., SI nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958-976) or intercalating agents. (see, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a mMafA nucleic acid of the invention, two complementary regions one having a fluorophore and one a quencher such that the molecular beacon is useful for quantitating the presence of the mMafA nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

RNAi

Double stranded nucleic acid molecules that can silence a mMafA gene can also be used as an agent that inhibits expression of mMafA. RNA interference (RNAi) is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an extremely powerful method for making targeted knockouts or "knockdowns" at the RNA level. RNAi has proven successful in human-cells, including human embryonic kidney and HeLa cells (see, e.g., Elbashir et al. Nature May 24, 2001;411(6836):494-8). In one embodiment, gene silencing can be induced in mammalian cells by enforcing endogenous expression of RNA hairpins (see Paddison et al., 2002, PNAS USA 99:1443-1448). In another embodiment, transfection of small (21-23 nt) dsRNA specifically inhibits gene expression (reviewed in Caplen (2002) Trends in Biotechnology 20:49-51).

Briefly, RNAi is thought to work as follows. dsRNA corresponding to a portion of a gene to be silenced is introduced into a cell. The dsRNA is digested into 21-23 nucleotide siRNAs, or short interfering RNAs. The siRNA duplexes bind to a nuclease complex to form what is known as the RNA-induced silencing complex, or RISC. The RISC targets the homologous transcript by base pairing interactions between one of the siRNA strands and the endogenous mRNA. It then cleaves the mRNA ~12 nucleotides from the 3' terminus of the siRNA (reviewed in Sharp et al (2001) *Genes Dev* 15: 485-490; and Hammond et al. (2001) *Nature Rev Gen* 2: 110-119).

RNAi technology in gene silencing utilizes standard molecular biology methods. dsRNA corresponding to the sequence from a target gene to be inactivated can be produced by standard methods, e.g., by simultaneous transcription of both strands of a template DNA (corresponding to the target sequence) with T7 RNA polymerase. Kits for production of dsRNA for use in RNAi are available commercially, e.g., from New England Biolabs, Inc. Methods of transfection of dsRNA or plasmids engineered to make dsRNA are routine in the art.

Gene silencing effects similar to those of RNAi have been reported in mammalian cells with transfection of a mRNA-cDNA hybrid construct (Lin et al., Biochem Biophys Res Commun Mar. 2, 2001;281(3):639-44), providing yet another strategy for gene silencing.

Isolated mMafA Polypeptides

In another aspect, the invention features, an isolated mMafA protein, or fragment, e.g., a biologically active portion, for use as immunogens or antigens to raise or test (or more generally to bind) anti-mMafA antibodies. mMafA protein can be isolated from cells or tissue sources using standard protein purification techniques. mMafA protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when expressed the polypeptide is expressed in a native cell, or in systems which result in the alteration or omission of post-translational modifications, e.g., glycosylation or cleavage, present when expressed in a native cell.

In a preferred embodiment, a mMafA polypeptide has one or more of the following characteristics:
  (i) it has the ability to homo-dimerize;
  (ii) it has the ability to form a dimer with another bZip protein;
  (iii) it has the ability to bind DNA, e.g., a RIPE 3b1 element;
  (iv) it has the ability to increase transcription of a responsive gene, e.g., an insulin gene.
  (v) it modulates insulin expression;
  (vi) it modulates pancreatic β-cell function, development and/or differentiation;
  (vii) it is recognized by an anti-mMafA antibody described herein;
  (viii) it has a molecular weight, e.g., a deduced molecular weight, preferably ignoring any contribution of post translational modifications, amino acid composition or other physical characteristic of SEQ ID NO:2 or 6;
  (ix) it has an overall sequence similarity of at least 50%, preferably at least 60%, more preferably at least 70, 80, 90, or 95%, with a polypeptide a of SEQ ID NO:2 or 6 or an alternatively spliced variant thereof;
  (x) it can be found in insulin producing cells or cell lines;
  (xi) it has a bZip domain;
  (xii) it has one, preferably 2 glycine rich regions as described herein.

In a preferred embodiment the mMafA protein, or fragment thereof, differs from the corresponding sequence in SEQ ID:2. In one embodiment it differs by at least one but by less than 15, 10 or 5 amino acid residues. In another it differs from the corresponding sequence in SEQ ID NO:2 or 6 by at least one residue but less than 20%, 15%, 10% or 5% of the residues in it differ from the corresponding sequence in SEQ ID NO:2 or 6. (If this comparison requires alignment the sequences should be aligned for maximum homology. "Looped" out sequences from deletions or insertions, or mismatches, are considered differences.) The differences are, preferably, differences or changes at a non essential residue or a conservative substitution. In a preferred embodiment the differences are not in the bZip motif, the transactivation domain, or the DNA binding domain. In another preferred embodiment one or more differences are in these domains.

Other embodiments include a protein that contain one or more changes in amino acid sequence, e.g., a change in an amino acid residue which is not essential for activity. Such mMafA proteins differ in amino acid sequence from SEQ ID NO:2 or 6, yet retain biological activity.

In one embodiment, the protein includes an amino acid sequence at least about 50%, 55%, 60%, 65%, 70%, 75%, 80%, 85%, 90%, 95%, 98% or more homologous to SEQ ID NO:2 or 6 or an alternatively spliced variant thereof described herein.

In one embodiment, a biologically active portion of a mMafA protein includes a bZip domain or other mMafA domain described herein. Moreover, other biologically active portions, in which other regions of the protein are deleted, can be prepared by recombinant techniques and evaluated for one or more of the functional activities of a native mMafA protein.

In a preferred embodiment, the mMafA protein has an amino acid sequence shown in SEQ ID NO:2 or 6. In other embodiments, the mMafA protein is substantially identical to SEQ ID NO:2 or 6. In yet another embodiment, the mMafA protein is substantially identical to SEQ ID NO:2 or 6 and retains the functional activity of the protein of SEQ ID NO:2 or 6, as described in detail in the subsections above.

mMafA Chimeric or Fusion Proteins

In another aspect, the invention provides mMafA chimeric or fusion proteins. As used herein, a mMafA "chimeric protein" or "fusion protein" includes a mMafA polypeptide, or functional fragment thereof, linked to a non-mMafA polypeptide. For example, a DNA binding and/or dimerization region of a Maf factor, e.g., MafA, MafB, c-Maf, NRL, MafK, MafF or MafG, can be linked to a transcriptional activation domain from another factor (e.g., a different Maf protein or another transcription factor, e.g., VP16). Such chimeric factors can be capable of turning on gene expression in insulin producing cells, thereby producing insulin expressing cells, e.g., for transplantation.

A "non-mMafA polypeptide" refers to a polypeptide having an amino acid sequence corresponding to a protein which is not substantially homologous to the mMafA protein, e.g., a protein which is different from the mMafA protein and which is derived from the same or a different organism. The mMafA polypeptide of the fusion protein can correspond to all or a portion e.g., a fragment described herein of a mMafA amino acid sequence. In a preferred embodiment, a mMafA fusion protein includes at least one (or two) biologically active portion of a mMafA protein. The non-mMafA polypeptide can be fused to the N-terminus or C-terminus of the mMafA polypeptide.

The fusion protein can include a moiety which has a high affinity for a ligand. For example, the fusion protein can be a GST-mMafA fusion protein in which the mMafA sequences are fused to the C-terminus of the GST sequences. Such fusion proteins can facilitate the purification of recombinant mMafA. Alternatively, the fusion protein can be a mMafA protein containing a heterologous signal sequence at its N-terminus. In certain host cells (e.g., mammalian host cells), expression and/or secretion of mMafA can be increased through use of a heterologous signal sequence.

Fusion proteins can include all or a part of a serum protein, e g., an IgG constant region, or human serum albumin.

The mMafA fusion proteins of the invention can be incorporated into pharmaceutical compositions and administered to a subject in vivo. The mMafA fusion proteins can be used to affect the bioavailability of a mMafA substrate. mMafA fusion proteins may be useful therapeutically for the treatment of disorders caused by, for example, (i) aberrant modification or mutation of a gene encoding a mMafA protein; (ii) mis-regulation of the mMafA gene; and (iii) aberrant post-translational modification of a mMafA protein.

Moreover, the mMafA-fusion proteins of the invention can be used as immunogens to produce anti-mMafA antibodies in a subject, to purify mMafA ligands and in screening assays to identify molecules which inhibit the interaction of mMafA with a mMafA substrate.

Expression vectors are commercially available that already encode a fusion moiety (e.g., a GST polypeptide). A mMafA-encoding nucleic acid can be cloned into such an expression vector such that the fusion moiety is linked in-frame to the mMafA protein.

Variants of mMafA Proteins

In another aspect, the invention also features a variant of a mMafA polypeptide, e.g., which functions as an agonist (mimetics) or as an antagonist. Variants of the mMafA proteins can be generated by mutagenesis, e.g., discrete point mutation, the insertion or deletion of sequences or the truncation of a mMafA protein. An agonist of the mMafA proteins can retain substantially the same, or a subset, of the biological activities of the naturally occurring form of a mMafA protein. An antagonist of a mMafA protein can inhibit one or more of the activities of the naturally occurring form of the mMafA protein by, for example, competitively modulating a mMafA-mediated activity of a mMafA protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the mMafA protein.

Variants of a mMafA protein can be identified by screening combinatorial libraries of mutants, e.g., truncation mutants, of a mMafA protein for agonist or antagonist activity.

Libraries of fragments e.g., N terminal, C terminal, or internal fragments, of a mMafA protein coding sequence can be used to generate a variegated population of fragments for screening and subsequent selection of variants of a mMafA protein. Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of mMafA proteins. Recursive ensemble mutagenesis (REM), a new technique which enhances the frequency of functional mutants in the libraries, can be used in combination with the screening assays to identify mMafA variants (Arkin and Yourvan (1992) *Proc. Natl. Acad. Sci. USA* 89:7811-7815; Delgrave et al. (1993) *Protein Engineering* 6:327-331).

Cell based assays can be exploited to analyze a variegated mMafA library. For example, a library of expression vectors can be transfected into a cell line, e.g., a cell line, which ordinarily responds to mMafA in a substrate-dependent manner. The transfected cells are then contacted with mMafA and the effect of the expression of the mutant on signaling by the mMafA substrate can be detected, e.g., by measuring DNA binding or transactivation activity. Plasmid DNA can then be recovered from the cells which score for inhibition, or alternatively, potentiation of signaling by the mMafA substrate, and the individual clones further characterized.

In another aspect, the invention features a method of making a mMafA polypeptide, e.g., a peptide having a non-wild type activity, e.g., an antagonist, agonist, or super agonist of a naturally occurring mMafA polypeptide, e.g., a naturally occurring mMafA polypeptide. The method includes: altering the sequence of a mMafA polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a mMafA polypeptide a biological activity of a naturally occurring mMafA polypeptide. The method includes: altering the sequence, e.g., by substitution or deletion of one or more residues, of a mMafA polypeptide, e.g., altering the sequence of a non-conserved region, or a domain or residue described herein, and testing the altered polypeptide for the desired activity.

Anti-mMafA Antibodies

In another aspect, the invention provides an anti-mMafA antibody, or a fragment thereof (e.g., an antigen-binding fragment thereof). The term "antibody" as used herein refers to an immunoglobulin molecule or immunologically active portion thereof, i.e., an antigen-binding portion. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition,* U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The anti-mMafA antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH—terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or simply "antibody portion," or "fragment"), as used herein, refers to one or more fragments of a full-length antibody that retain the ability to specifically bind to the antigen, e.g., mMafA polypeptide or fragment thereof. Examples of antigen-binding fragments of the anti-mMafA antibody include, but are not limited to: (i) a Fab fragment, a monovalent fragment consisting of the VL, VH, CL and CHI domains; (ii) a F(ab')$_2$ fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding fragment" of an antibody. These antibody fragments are obtained using conventional techniques known to those with skill in the art, and the fragments are screened for utility in the same manner as are intact antibodies.

The anti-mMafA antibody can be a polyclonal or a monoclonal antibody. In other embodiments, the antibody can be recombinantly produced, e.g., produced by phage display or by combinatorial methods.

Phage display and combinatorial methods for generating anti-mMafA antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-

1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the anti-mMafA antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An anti-mMafA antibody can be one in which the variable region, or a portion thereof, e.g., the CDR's, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a mMafA or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a mMafA polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

A full-length mMafA protein or, antigenic peptide fragment of mMafA can be used as an immunogen or can be used to identify anti-mMafA antibodies made with other immunogens, e.g., cells, membrane preparations, and the like. The antigenic peptide of mMafA should include at least 8 amino acid residues of the amino acid sequence shown in SEQ ID NO:2 or 6 and encompasses an epitope of mMafA. Preferably, the antigenic peptide includes at least 10 amino acid residues, more preferably at least 15 amino acid residues, even more preferably at least 20 amino acid residues, and most preferably at least 30 amino acid residues.

Antibodies reactive with, or specific for, any of these regions, or other regions or domains described herein are provided.

Antibodies which bind only native mMafA protein, only denatured or otherwise normative mMafA protein, or which bind both, are with in the invention. Antibodies with linear or conformational epitopes are within the invention. Conformational epitopes can sometimes be identified by identifying antibodies which bind to native but not denatured mMafA protein.

Preferred epitopes encompassed by the antigenic peptide are regions of mMafA are located on the surface of the protein, e.g., hydrophilic regions, as well as regions with high antigenicity. For example, an Emini surface probability analysis of the human mMafA protein sequence can be used to indicate the regions that have a particularly high probability of being localized to the surface of the mMafA protein and are thus likely to constitute surface residues useful for targeting antibody production.

The anti-mMafA antibody can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target mMafA protein.

In a preferred embodiment the antibody has effector function and/or can fix complement. In other embodiments the antibody does not recruit effector cells; or fix complement.

In a preferred embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

In a preferred embodiment, an anti-mMafA antibody alters (e.g., increases or decreases) a mMafA activity described herein.

The antibody can be coupled to a toxin, e.g., a polypeptide toxin, e,g, ricin or diphtheria toxin or active fragment hereof, or a radioactive nucleus, or imaging agent, e.g. a radioactive, enzymatic, or other, e.g., imaging agent, e.g., a NMR contrast agent. Labels which produce detectable radioactive emissions or fluorescence are preferred.

An anti-mMafA antibody (e.g., monoclonal antibody) can be used to isolate mMafA by standard techniques, such as affinity chromatography or immunoprecipitation. Moreover, an anti-mMafA antibody can be used to detect mMafA protein (e.g., in a cellular lysate or cell supernatant) in order to evaluate the abundance and pattern of expression of the protein. Anti-mMafA antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The invention also includes a nucleic acid which encodes an anti-mMafA antibody, e.g., an anti-mMafA antibody described herein. Also included are vectors which include the nucleic acid and cells transformed with the nucleic acid, particularly cells which are useful for producing an antibody, e.g., mammalian cells, e.g. CHO or lymphatic cells.

The invention also includes cell lines, e.g., hybridomas, which make an anti-mMafA antibody, e.g., and antibody described herein, and method of using said cells to make a mMafA antibody.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a mMafA nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., mMafA proteins, mutant forms of mMafA proteins, fusion proteins, and the like).

The recombinant expression vectors of the invention can be designed for expression of mMafA proteins in prokaryotic or eukaryotic cells. For example, polypeptides of the invention can be expressed in *E. coli,* insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in mMafA activity assays, (e.g., direct assays or competitive assays described in detail below), or to generate antibodies specific for mMafA proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in E. coli is to express the protein in a host bacteria with an impaired capacity to proteolytically cleave the recombinant protein (Gottesman, S., (1990) Gene Expression Technology. Methods in Enzymology 185, Academic Press, San Diego, Calif. 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

The mMafA expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) Proc. Natl. Acad. Sci. USA 89:5547, and Paillard (1989) Human Gene Therapy 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a mMafA nucleic acid molecule within a recombinant expression vector or a mMafA nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a mMafA protein can be expressed in bacterial cells (such as E. coli), insect cells, yeast or mammalian cells (such as Chinese hamster ovary cells (CHO) or COS cells (African green monkey kidney cells CV-1 origin SV40 cells; Gluzman (1981) Cell123:175-182)). Other suitable host cells are known to those skilled in the art.

Host cells for methods of producing insulin as described herein can include glucose responsive and non-glucose responsive cells. Embryonic stem cells, pancreatic precursor cells, primary beta-cells or cell lines derived from islet beta-cells or insulinomas are examples of cells that can be used for glucose responsive production of insulin. Expression of glucokinase and glucose transporter activity (e.g., GLUT-2) in these cells can aid in glucose sensing. In addition, cells that normally lack glucose-stimulated peptide release may be engineered for this function. The use of these genes as a general tool for engineering of glucose sensing has been described in, e.g., Newgard, U.S. Pat. No. 5,427,940. Neuroendocrine cells that can be engineered to be glucose sensitive include AtT-20 cells, which are derived from ACTH secreting cells of the anterior pituitary; PC 12, a neuronal cell line (ATCC CRL 1721); and GH3, an anterior pituitary cell line that secretes growth hormone (ATCC CCL82.1).

Vector DNA can be introduced into host cells via conventional transformation or transfection techniques. As used herein, the terns "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a mMafA protein. Accordingly, the invention further provides methods for producing a mMafA protein using the host cells of the invention. In one embodiment, the method includes culturing the host cell of the invention (into which a recombinant expression vector encoding a mMafA protein has been introduced) in a suitable medium such that a mMafA protein is produced. In another embodiment, the method further includes isolating a mMafA protein from the medium or the host cell.

In another aspect, the invention features, a cell or purified preparation of cells which include a mMafA transgene, or which otherwise misexpress mMafA. The cell preparation can consist of human or non-human cells, e.g., rodent cells, e.g., mouse or rat cells, rabbit cells, or pig cells. In preferred embodiments, the cell or cells include a mMafA transgene, e.g., a heterologous form of a mMafA, e.g., a gene derived from humans (in the case of a non-human cell). The mMafA transgene can be misexpressed, e.g., overexpressed or underexpressed. In other preferred embodiments, the cell or cells include a gene that mis-expresses an endogenous mMafA, e.g., a gene the expression of which is disrupted, e.g., a knockout. Such cells can serve as a model for studying disorders that are related to mutated or mis-expressed mMafA alleles or for use in drug screening.

In another aspect, the invention features, a human cell (e.g., a pancreatic β-cell, β-cell precursor cell, adult or embryonic stem cell, a human neuroendocrine cell, pancreatic ductal cell or cell line, pancreatic acinar cell or cell line, pancreatic endocrine cell or cell line, enteroendocrine cell or cell line, hepatic cell, fibroblast, endothelial cell, or muscle cell) transformed with nucleic acid which encodes a subject mMafA polypeptide.

Also provided are cells, preferably human cells, e.g., stem cells, pancreatic cells, e.g., β-cells, or fibroblast cells, in which an endogenous mMafA is under the control of a regulatory sequence that does not normally control the expression of the endogenous mMafA gene. The expression characteristics of an endogenous gene within a cell, e.g., a cell line or microorganism, can be modified by inserting a heterologous DNA regulatory element into the genome of the cell such that the inserted regulatory element is operably linked to the endogenous mMafA gene. For example, an endogenous mMafA gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

In a preferred embodiment, recombinant cells described herein can be used for replacement therapy in a subject. For example, a nucleic acid encoding a mMafA polypeptide operably linked to an inducible promoter (e.g., a steroid hormone receptor-regulated promoter) is introduced into a human or nonhuman, e.g., mammalian, e.g., porcine recombinant cell. The cell is cultivated and encapsulated in a biocompatible material, such as poly-lysine alginate, and subsequently implanted into the subject. See, e.g., Lanza (1996) *Nat. Biotechnol.* 14:1107; Joki et al. (2001) *Nat. Biotechnol.* 19:35; and U.S. Pat. No. 5,876,742. Production of mMafA polypeptide can be regulated in the subject by administering an agent (e.g., a steroid hormone) to the subject. In another preferred embodiment, the implanted recombinant cells express and secrete an antibody specific for a mMafA polypeptide. The antibody can be any antibody or any antibody derivative described herein.

Transgenic Animals

The invention provides nonhuman transgenic animals. Such animals are useful for studying the function and/or activity of a mMafA protein and for identifying and/or evaluating modulators of mMafA activity. As used herein, a "transgenic animal" is a nonhuman animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous mMafA gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a mMafA protein to particular cells. A transgenic founder animal can be identified based upon the presence of a mMafA transgene in its genome and/or expression of mMafA mRNA in tissues or cells of the animals. A transgenic founder animal can then be used to breed additional animals carrying the transgene. Moreover, transgenic animals carrying a transgene encoding a mMafA protein can further be bred to other transgenic animals carrying other transgenes.

mMafA proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); c) methods of treatment (e.g., therapeutic and prophylactic); and d) biomaterials.

The isolated nucleic acid molecules of the invention can be used, for example, to express a mMafA protein (e.g., via a recombinant expression vector in a host cell in gene therapy applications), to detect a mMafA mRNA (e.g., in a biological sample) or a genetic alteration in a mMafA gene, and to modulate mMafA activity, e.g., to induce beta cell development and/or differentiation, or provide an insulin producing cell as described herein. The mMafA proteins can be used to treat insulin related disorders. In addition, the mMafA proteins can be used to screen for naturally occurring mMafA substrates, to screen for drugs or compounds which modulate mMafA activity, as well as to treat disorders characterized by insufficient or excessive production of mMafA protein or production of mMafA protein forms which have decreased, aberrant or unwanted activity compared to mMafA wild type protein. Moreover, the anti-mMafA antibodies of the invention can be used to detect and isolate mMafA proteins, regulate the bioavailability of mMafA proteins, and modulate mMafA activity.

A method of evaluating a compound for the ability to interact with, e.g., bind, a subject mMafA polypeptide is provided. The method includes: contacting the compound with the subject mMafA polypeptide; and evaluating ability of the compound to interact with, e.g., to bind or form a complex with the subject mMafA polypeptide. This method can be performed in vitro, e.g., in a cell free system, or in vivo, e.g., in a two-hybrid interaction trap assay. This method can be used to identify naturally occurring molecules that interact with subject mMafA polypeptide. It can also be used to find natural or synthetic inhibitors of subject mMafA polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to mMafA proteins, have a stimulatory or inhibitory effect on, for example, mMafA expression or mMafA activity, or have a stimulatory or inhibitory effect on, for example, the expression or activity of a mMafA substrate. Compounds thus identified can be used to modulate the activity of target gene products (e.g., mMafA genes) in a therapeutic protocol, to elaborate the biological function of the target gene product, or to identify compounds that disrupt normal target gene interactions.

Such screening assays can include: providing a Maf protein or nucleic acid, e.g., mMafA, MafB, c-Maf, NRL, MafK, MafG or MafF protein or nucleic acid or a functional fragment thereof; contacting the Maf protein or nucleic acid with a test compound, and determining if the test compound modulates the Maf protein or nucleic acid. A test compound may modulate a Maf activity by, e.g., binding to the Maf protein and facilitating or inhibiting any of: Maf homo or heterodimerization; Maf DNA binding; Maf transcriptional activation. The compound can be, e.g., an antibody, e.g., an inhibitory Maf antibody or an antibody that stabilizes or assists Maf binding to DNA or another bZip protein. A test compound may also modulate a Maf activity by binding to a Maf nucleic acid or fragment thereof. for example, the test compound may bind to the Maf promoter region and increase Maf transcription; the test compound may bind to a Maf nucleic acid and inhibit transcription of the Maf gene; or the test compound may bind to a Maf nucleic acid and inhibit translation of the Maf mRNA. In a preferred embodiment, the compound is a small molecule that binds to the Maf promoter region to modulate transcription.

A test compound may also compete with the endogenous Maf protein for binding to a Maf binding partner g., DNA or a bZip protein, thereby inhibiting a Maf activity. For example, the test compound can be a dominant negative Maf protein or nucleic acid or a dominant negative Maf binding partner, e.g., a dominant negative bZip protein. In a preferred embodiment, the compound is a dominant negative Maf protein, e.g., a Maf protein containing a functional DNA binding domain and a non-functional, absent or heterologous transcriptional activation domain, or a Maf protein containing a functional transcriptional activation domain and a non-functional, absent, or heterologous DNA binding domain. The test compound may modulate Maf nuclear localization, e.g., the compound may bind to a Maf protein and inhibit or facilitate the passage of the Maf protein through the nuclear pores. The test agent can be, e.g., a protein or peptide, an antibody, a small molecule, a nucleotide sequence. For example, the agent can be an agent identified through a library screen described herein.

The screening assays described herein can be performed in vitro or in vivo. If performed in vitro, the assay can further include administering the test compound to an experimental animal.

The test compounds of the screening assays described herein can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; sec, e.g., Zuckermann, R. N. et al. (1994) *J. Med. Chem.* 37:2678-85); spatially addressable parallel solid phase or solution phase libraries; synthetic library methods requiring deconvolution; the 'one-bead onecompound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In one embodiment, an assay is a cell-based assay in which a cell which expresses a mMafA protein or biologically active portion thereof is contacted with a test compound, and the ability of the test compound to modulate mMafA activity is determined. Determining the ability of the test compound to modulate mMafA activity can be accomplished by monitoring, for example, DNA binding, complex formation or transcriptional activation activity. The cell, for example, can be of mammalian origin, e.g., human.

The ability of the test compound to modulate mMafA binding to a compound, e.g., a mMafA substrate, or to bind to mMafA can also be evaluated. This can be accomplished, for example, by coupling the compound, e.g., the substrate, with a radioisotope or enzymatic label such that binding of the compound, e.g., the substrate, to mMafA can be determined by detecting the labeled compound, e.g., substrate, in a complex. Alternatively, mMafA could be coupled with a radioisotope or enzymatic label to monitor the ability of a test compound to modulate mMafA binding to a mMafA substrate in a complex. For example, compounds (e.g., mMafA substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a mMafA substrate) to interact with mMafA with or without the labeling of any of the interactants can be evaluated. For example, a microphysiometer can be used to detect the interaction of a compound with mMafA without the labeling of either the compound or the mMafA. McConnell, H. M. et al. (1992) *Science* 257: 1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and mMafA.

In yet another embodiment, a cell-free assay is provided in which a mMafA protein or biologically active portion thereof is contacted with a test compound and the ability of the test compound to bind to the mMafA protein or biologically active portion thereof is evaluated. Preferred biologically active portions of the mMafA proteins to be used in assays of the present invention include fragments which participate in interactions with non-mMafA molecules, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the mMafA protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either mMafA, an anti-mMafA antibody or its target molecule to facilitate separation of complexed from uncomplexed forms of one or both of the proteins, as well as to accommodate automation of the assay. Binding of a test compound to a mMafA protein, or interaction of a mMafA protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/mMafA fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or mMafA protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of mMafA binding or activity determined using standard techniques.

Other techniques for immobilizing either a mMafA protein or a target molecule on matrices include using conjugation of biotin and streptavidin. Biotinylated mMafA protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with mMafA protein or target molecules but which do not interfere with binding of the mMafA protein to its target molecule. Such antibodies can be derivatized to the wells of the plate, and unbound target or mMafA protein trapped in the wells by antibody conjugation. Methods for detecting such complexes, in addition to those described above for the GST-immobilized complexes, include immunodetection of complexes using antibodies reactive with the mMafA protein or target molecule, as well as enzyme-linked assays which rely on detecting an enzymatic activity associated with the mMafA protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology,* J. Wiley: New York). Such resins and chromatographic techniques are known to one skilled in the art (see, e.g., Heegaard, N. H., (1998) *J Mol Recognit* 11: 141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the mMafA protein or biologically active portion thereof with a known compound which binds mMafA to form an assay mixture, contacting the assay mixture with a test compound, and determining the ability of the test compound to interact with a mMafA protein, wherein determining the ability of the test compound to interact with a mMafA protein includes determining the ability of the test compound to preferentially bind to mMafA or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the mMafA genes herein identified. In an alternative embodiment, the invention provides methods for determining the ability of the test compound to modulate the activity of a mMafA protein through modulation of the activity of a downstream effector of a mMafA target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the mMafA proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with mMafA ("mMafA-binding proteins" or "mMafA-bp") and are involved in mMafA activity. Such mMafA-bps can be activators or inhibitors of signals by the mMafA proteins or mMafA targets as, for example, downstream elements of a mMafA-mediated signaling pathway.

The two-hybrid system is based on the modular nature of most transcription factors, which consist of separable DNA-binding and activation domains. Briefly, the assay utilizes two different DNA constructs. In one construct, the gene that codes for a mMafA protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: mMafA protein can be the fused to the activator domain.) If the "bait" and the "prey" proteins are able to interact, in vivo, forming a mMafA-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the mMafA protein.

In another embodiment, modulators of mMafA expression are identified. For example, a cell or cell free mixture is contacted with a candidate compound and the expression of mMafA mRNA or protein evaluated relative to the level of expression of mMafA mRNA or protein in the absence of the candidate compound. When expression of mMafA mRNA or protein is greater in the presence of the candidate compound than in its absence, the candidate compound is identified as a stimulator of mMafA mRNA or protein expression. Alternatively, when expression of mMafA mRNA or protein is less (statistically significantly less) in the presence of the candidate compound than in its absence, the candidate compound is identified as an inhibitor of mMafA mRNA or protein expression. The level of mMafA mRNA or protein expression can be determined by methods described herein for detecting mMafA mRNA or protein.

In another aspect, the invention pertains to a combination of two or more of the assays described herein. For example, a modulating agent can be identified using a cell-based or a cell free assay, and the ability of the agent to modulate the activity of a mMafA protein can be confirmed in vivo, e.g., in an animal such as an animal model for a β-cell or insulin related disorder, e.g., β-cell dysfunction, diabetes (e.g., insulin-dependent diabetes mellitus or non insulin-dependent diabetes mellitus) and its associated disorders, e.g., hypertension, retinopathy, persistent hyperinsulinemic hypoglycaemia of infancy (PHHI), insulin resistance, hyperglycemia, glucose intolerance, glucotoxicity.

This invention further pertains to novel agents identified by the above-described screening assays. Accordingly, it is within the scope of this invention to further use an agent identified as described herein (e.g., a mMafA modulating agent, an antisense mMafA nucleic acid molecule, a mMafA-specific antibody, or a mMafA-binding partner) in an appropriate animal model to determine the efficacy, toxicity, side effects, or mechanism of action, of treatment with such an agent. Furthermore, novel agents identified by the above-described screening assays can be used for treatments as described herein.

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes mMafA, e.g., an insulin related disorder.

Such disorders include, e.g., a disorder associated with the misexpression of mMafA gene; a disorder of the insulin metabolism or pancreatic tissue system, e.g., diabetes (e.g., insulin-dependent diabetes mellitus or non insulin-dependent diabetes mellitus) and its associated disorders, e.g., hypertension and retinopathy, persistent hyperinsulinemic hypoglycaemia of infancy (PHHI), insulin resistance, hyperglycemia, glucose intolerance, glucotoxicity, or β-cell dysfunction.

The method includes one or more of the following:
  detecting, in a tissue of the subject, the presence or absence of a mutation which affects the expression of the mMafA gene, or detecting the presence or absence of a mutation in a region which controls the expression of the gene, e.g., a mutation in the 5' control region, intron, or 3' untranslated region;
  detecting, in a tissue of the subject, the presence or absence of a mutation which alters the structure of the mMafA gene;
  detecting, in a tissue of the subject, the misexpression of the mMafA gene, at the mRNA level, e.g., detecting a non-wild type level of a mRNA;
  detecting, in a tissue of the subject, the misexpression of the gene, at the protein level, e.g., detecting a non-wild type level of a mMafA polypeptide.

In preferred embodiments the method includes: ascertaining the existence of at least one of: a deletion of one or more nucleotides from the mMafA gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the mMafA gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the mMafA gene; the presence of a non-wild type splicing pattern of a messenger RNA transcript of the gene; or a non-wild type level of mMafA.

Methods of the invention can be used prenatally or to determine if a subject's offspring will be at risk for a disorder.

In preferred embodiments the method includes determining the structure of a mMafA gene, an abnormal structure being indicative of risk for the disorder.

In preferred embodiments the method includes contacting a sample from the subject with an antibody to the mMafA protein or a nucleic acid, which hybridizes specifically with the gene. These and other embodiments are discussed below.

Diagnostic and Prognostic Assays

Diagnostic and prognostic assays of the invention include method for assessing the expression level of mMafA molecules and for identifying variations and mutations in the sequence of mMafA molecules.

Expression Monitoring and Profiling. The presence, level, or absence of mMafA protein or nucleic acid in a biological sample can be evaluated by obtaining a biological sample from a test subject and contacting the biological sample with a compound or an agent capable of detecting mMafA protein or nucleic acid (e.g., mRNA, genomic DNA) that encodes mMafA protein such that the presence of mMafA protein or nucleic acid is detected in the biological sample. The term "biological sample" includes tissues, cells and biological fluids isolated from a subject, as well as tissues, cells and fluids present within a subject. A preferred biological sample is serum. The level of expression of the mMafA gene can be measured in a number of ways, including, but not limited to: measuring the mRNA encoded by the mMafA genes; measuring the amount of protein encoded by the mMafA genes; or measuring the activity of the protein encoded by the mMafA genes.

The level of mRNA corresponding to the mMafA gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length mMafA nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to mMafA mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the mMafA genes.

The level of mRNA in a sample that is encoded by one of mMafA can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the mMafA gene being analyzed.

In another embodiment, the methods further contacting a control sample with a compound or agent capable of detecting mMafA mRNA, or genomic DNA, and comparing the presence of mMafA mRNA or genomic DNA in the control sample with the presence of mMafA mRNA or genomic DNA in the test sample. In still another embodiment, serial analysis of gene expression, as described in U.S. Pat. No. 5,695,937, is used to detect mMafA transcript levels.

A variety of methods can be used to determine the level of protein encoded by mMafA. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect mMafA protein in a biological sample in vitro as well as in vivo. In vitro techniques for detection of mMafA protein include enzyme linked immunosorbent assays (ELISAs), immunoprecipitations, immunofluorescence, enzyme immunoassay (EIA), radioimmunoassay (RIA), and Western blot analysis. In vivo techniques for detection of mMafA protein include introducing into a subject a labeled anti-mMafA antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-mMafA antibody positioned on an antibody array (as described below). The sample can be detected, e.g., with avidin coupled to a fluorescent label.

In another embodiment, the methods further include contacting the control sample with a compound or agent capable of detecting mMafA protein, and comparing the presence of mMafA protein in the control sample with the presence of mMafA protein in the test sample.

The invention also includes kits for detecting the presence of mMafA in a biological sample. For example, the kit can include a compound or agent capable of detecting mMafA protein or mRNA in a biological sample; and a standard. The compound or agent can be packaged in a suitable container. The kit can further comprise instructions for using the kit to detect mMafA protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted mMafA expression or activity. As used herein, the term "unwanted" includes an unwanted phenomenon involved in a biological response such as pancreatic tissue formation and maintenace.

In one embodiment, a disease or disorder associated with aberrant or unwanted mMafA expression or activity is identified. A test sample is obtained from a subject and mMafA protein or nucleic acid (e.g., mRNA or genomic DNA) is evaluated, wherein the level, e.g., the presence or absence, of mMafA protein or nucleic acid is diagnostic for a subject having or at risk of developing a disease or disorder associated with aberrant or unwanted mMafA expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted mMafA expression or activity.

In another aspect, the invention features a computer medium having a plurality of digitally encoded data records. Each data record includes a value representing the level of expression of mMafA in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression of genes other than mMafA (e.g., other genes associated with a mMafA-disorder, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of mMafA expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a cell or insulin related disorder, e.g., diabetes (e.g., insulin-dependent diabetes mellitus or non insulin-dependent diabetes mellitus) and its associated disorders, e.g., hypertension, retinopathy, persistent hyperinsulinemic hypoglycaemia of infancy (PHHI), insulin resistance, hyperglycemia, glucose intolerance, glucotoxicity in a subject wherein an increase or decrease in mMafA expression is an indication that the subject has or is disposed to having a β-cell or insulin related disorder described herein. The method can be used to monitor a treatment for a β-cell or insulin related disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of mMafA expression. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of mMafA expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of mMafA expression.

Arrays and Uses Thereof

In another aspect, the invention features an array that includes a substrate having a plurality of addresses. At least one address of the plurality includes a capture probe that binds specifically to a mMafA molecule (e.g., a mMafA nucleic acid or a mMafA polypeptide). The array can have a density of at least than 10, 50, 100, 200, 500, 1,000, 2,000, or 10,000 or more addresses/cm$^2$, and ranges between. In a preferred embodiment, the plurality of addresses includes at least 10, 100, 500, 1,000, 5,000, 10,000, 50,000 addresses. In a preferred embodiment, the plurality of addresses includes equal to or less than 10, 100, 500, 1,000, 5,000, 10,000, or 50,000 addresses. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a mMafA nucleic acid, e.g., the sense or antisense strand. In one preferred embodiment, a subset of addresses of the plurality of addresses has a nucleic acid capture probe for mMafA. Each address of the subset can include a capture probe that hybridizes to a different region of a mMafA nucleic acid. In another preferred embodiment, addresses of the subset include a capture probe for a mMafA nucleic acid. Each address of the subset is unique, overlapping, and complementary to a different variant of mMafA (e.g., an allelic variant, or all possible hypothetical variants). The array can be used to sequence mMafA by hybridization (see, e.g., U.S. Pat. No. 5,695,940).

An array can be generated by various methods, e.g., by photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145).

In another preferred embodiment, at least one address of the plurality includes a polypeptide capture probe that binds specifically to a mMafA polypeptide or fragment thereof. The polypeptide can be a naturally-occurring interaction partner of mMafA polypeptide. Preferably, the polypeptide is an antibody, e.g., an antibody described herein (see "Anti-mMafA Antibodies," above), such as a monoclonal antibody or a single-chain antibody.

In another aspect, the invention features a method of analyzing the expression of mMafA. The method includes providing an array as described above; contacting the array with a sample and detecting binding of a mMafA-molecule (e.g., nucleic acid or polypeptide) to the array. In a preferred embodiment, the array is a nucleic acid array. Optionally the method further includes amplifying nucleic acid from the sample prior or during contact with the array.

In another embodiment, the array can be used to assay gene expression in a tissue to ascertain tissue specificity of genes in the array, particularly the expression of mMafA. If a sufficient number of diverse samples is analyzed, clustering (e.g., hierarchical clustering, k-means clustering, Bayesian clustering and the like) can be used to identify other genes which are co-regulated with mMafA. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on mMafA expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a mMafA-associated disease or disorder; and processes, such as a cellular transformation associated with a mMafA-associated disease or disorder. The method can also evaluate the treatment and/or progression of a mMafA-associated disease or disorder The array is also useful for ascertaining differential expression patterns of one or more genes in normal and abnormal cells. This provides a battery of genes (e.g., including mMafA) that could serve as a molecular target for diagnosis or therapeutic intervention.

In another aspect, the invention features an array having a plurality of addresses. Each address of the plurality includes a unique polypeptide. At least one address of the plurality has disposed thereon a mMafA polypeptide or fragment thereof. Methods of producing polypeptide arrays are described in the art, e.g., in De Wildt et al (2000). *Nature Biotech.* 18, 989-994; Lueking et al. (1999). *Anal. Biochem.* 270, 103-111; Ge, H. (2000). *Nucleic Acids Res.* 28, e3, I-VII; MacBeath, G., and Schreiber, S. L. (2000). *Science* 289, 1760-1763; and WO 99/51773A1. In a preferred embodiment, each addresses of the plurality has disposed thereon a polypeptide at least 60, 70, 80,85, 90, 95 or 99% identical to a mMafA polypeptide or fragment thereof. For example, multiple variants of a mMafA polypeptide (e.g., encoded by allelic variants, site-directed mutants, random mutants, or combinatorial mutants) can be disposed at individual addresses of the plurality. Addresses in addition to the address of the plurality can be disposed on the array.

The polypeptide array can be used to detect a mMafA binding compound, e.g., an antibody in a sample from a subject with specificity for a mMafA polypeptide or the presence of a mMafA-binding protein or ligand.

The array is also useful for ascertaining the effect of the expression of a gene on the expression of other genes in the same cell or in different cells (e.g., ascertaining the effect of mMafA expression on the expression of other genes). This provides, for example, for a selection of alternate molecular targets for therapeutic intervention if the ultimate or downstream target cannot be regulated.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express mMafA or from a cell or subject in which a mMafA mediated response has been elicited, e.g., by contact of the cell with mMafA nucleic acid or protein, or administration to the cell or subject mMafA nucleic acid or protein; providing a two dimensional array having a plurality of addresses, each address of the plurality being positionally distinguishable from each other address of the plurality, and each address of the plurality having a unique capture probe, e.g., wherein the capture probes are from a cell or subject which does not express mMafA (or does not express as highly as in the case of the mMafA positive plurality of capture probes) or from a cell or subject which in which a mMafA mediated response has not been elicited (or has been elicited to a lesser extent than in the first sample); contacting the array with one or more inquiry probes (which is preferably other than a mMafA nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing a plurality of probes or a sample. The method is useful, e.g., for analyzing gene expression. The method includes: providing a two dimensional array having a plurality of addresses, each address of the plurality being positionally distinguishable from each other address of the plurality having a unique capture probe, contacting the array with a first sample from a cell or subject which express or mis-express mMafA or from a cell or subject in which a mMafA-mediated response has been elicited, e.g., by contact of the cell with mMafA nucleic acid or protein, or administration to the cell or subject mMafA nucleic acid or protein; providing a two dimensional array having a plurality of addresses, each address of the plurality being positionally distinguishable from each other address of the plurality, and each address of the plurality having a unique capture probe, and contacting the array with a second sample from a cell or subject which does not express mMafA (or does not express as highly as in the case of the mMafA positive plurality of capture probes) or from a cell or subject which in which a mMafA mediated response has not been elicited (or has been elicited to a lesser extent than in the first sample); and comparing the binding of the first sample with the binding of the second sample. Binding, e.g., in the case of a nucleic acid, hybridization with a capture probe at an address of the plurality, is detected, e.g., by signal generated from a label attached to the nucleic acid, polypeptide, or antibody. The same array can be used for both samples or different arrays can be used. If different arrays are used the plurality of addresses with capture probes should be present on both arrays.

In another aspect, the invention features a method of analyzing mMafA, e.g., analyzing structure, function, or relatedness to other nucleic acid or amino acid sequences. The method includes: providing a mMafA nucleic acid or amino acid sequence; comparing the mMafA sequence with one or more preferably a plurality of sequences from a collection of sequences, e.g., a nucleic acid or protein sequence database; to thereby analyze mMafA.

Detection of Variations or Mutations

The methods of the invention can also be used to detect genetic alterations in a mMafA gene, thereby determining if a subject with the altered gene is at risk for a disorder characterized by misregulation in mMafA protein activity or nucleic acid expression, such as a β-cell or insulin related disorder described herein. In preferred embodiments, the methods include detecting, in a sample from the subject, the presence or absence of a genetic alteration characterized by at least one of an alteration affecting the integrity of a gene encoding a mMafA-protein, or the mis-expression of the mMafA gene. For example, such genetic alterations can be detected by ascertaining the existence of at least one of 1) a deletion of one or more nucleotides from a mMafA gene; 2) an addition of one or more nucleotides to a mMafA gene; 3) a substitution of one or more nucleotides of a mMafA gene, 4) a chromosomal rearrangement of a mMafA gene; 5) an alteration in the level of a messenger RNA transcript of a mMafA gene, 6) aberrant modification of a mMafA gene, such as of the methylation pattern of the genomic DNA, 7) the presence of a non-wild type splicing pattern of a messenger RNA transcript of a mMafA gene, 8) a non-wild type level of a mMafA-protein, 9) allelic loss of a mMafA gene, and 10) inappropriate post-translational modification of a mMafA-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the mMafA-gene. This method can include the steps of collecting a sample of cells from a subject, isolating nucleic acid (e.g., genomic, mRNA or both) from the sample, contacting the nucleic acid sample with one or more primers which specifically hybridize to a mMafA gene under conditions such that hybridization and amplification of the mMafA-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a mMafA gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in mMafA can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. A probe can be complementary to a region of a mMafA nucleic acid or a putative variant (e.g., allelic variant) thereof. A probe can have one or more mismatches to a region of a mMafA nucleic acid (e.g., a destabilizing mismatch). The arrays can have a high density of addresses, e.g., can contain hundreds or thousands of oligonucleotides probes (Cronin, M. T. et al. (1996) *Human Mutation* 7: 244-255; Kozal, M. J. et al. (1996) *Nature Medicine* 2: 753759). For example, genetic mutations in mMafA can be identified in two-dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the mMafA gene and detect mutations by comparing the sequence of the sample mMafA with the corresponding wild-type (control) sequence. Automated sequencing procedures can be utilized when performing the diagnostic assays ((1995) *Biotechniques* 19:448), including sequencing by mass spectrometry.

Other methods for detecting mutations in the mMafA gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol*. 217:286-295).

In still another embodiment, the mismatch cleavage reaction employs one or more proteins that recognize mismatched base pairs in double-stranded DNA (so called "DNA mismatch repair" enzymes) in defined systems for detecting and mapping point mutations in mMafA cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662; U.S. Pat. No. 5,459,039).

In other embodiments, alterations in electrophoretic mobility will be used to identify mutations in mMafA genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res*. 285:125-144; and Hayashi (1992) *Genet. Anal. Tech. Appl.* 9:73-79). Single-stranded DNA fragments of sample and control mMafA nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) Nature 324:163); Saiki et al. (1989) *Proc. Natl Acad. Sci USA* 86:6230). A further method of detecting point mutations is the chemical ligation of oligonucleotides as described in Xu et al. ((2001) Nature Biotechnol. 19:148). Adjacent oligonucleotides, one of which selectively anneals to the query site, are ligated together if the nucleotide at the query site of the sample nucleic acid is complementary to the query oligonucleotide; ligation can be monitored, e.g., by fluorescent dyes coupled to the oligonucleotides.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res*. 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another aspect, the invention features a set of oligonucleotides. The set includes a plurality of oligonucleotides, each of which is at least partially complementary (e.g., at least 50%, 60%, 70%, 80%, 90%, 92%, 95%, 97%, 98%, or 99% complementary) to a mMafA nucleic acid.

In a preferred embodiment the set includes a first and a second oligonucleotide. The first and second oligonucleotide can hybridize to the same or to different locations of SEQ ID NO:1 or the complement of SEQ ID NO:1. Different locations can be different but overlapping, or non-overlapping on the same strand. The first and second oligonucleotide can hybridize to sites on the same or on different strands.

The set can be useful, e.g., for identifying SNP's, or identifying specific alleles of mMafA. In a preferred embodiment, each oligonucleotide of the set has a different nucleotide at an interrogation position. In one embodiment, the set includes two oligonucleotides, each complementary to a different allele at a locus, e.g., a biallelic or polymorphic locus.

In another embodiment, the set includes four oligonucleotides, each having a different nucleotide (e.g., adenine, guanine, cytosine, or thymidine) at the interrogation position. The interrogation position can be a SNP or the site of a mutation. In another preferred embodiment, the oligonucleotides of the plurality are identical in sequence to one another (except for differences in length). The oligonucleotides can be provided with differential labels, such that an oligonucleotide that hybridizes to one allele provides a signal that is distinguishable from an oligonucleotide that hybridizes to a second allele. In still another embodiment, at least one of the oligonucleotides of the set has a nucleotide change at a position in addition to a query position, e.g., a destabilizing mutation to decrease the $T_m$ of the oligonucleotide. In another embodiment, at least one oligonucleotide of the set has a non-natural nucleotide, e.g., inosine. In a preferred embodiment, the oligonucleotides are attached to a solid support, e.g., to different addresses of an array or to different beads or nanoparticles.

In a preferred embodiment the set of oligo nucleotides can be used to specifically amplify, e.g., by PCR, or detect, a mMafA nucleic acid.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving a mMafA gene.

Use of mMafA Molecules as Surrogate Markers

The mMafA molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the mMafA molecules of the invention may be detected, and may be correlated with one or more biological states in vivo. For example, the mMafA molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258-264; and James (1994) *AIDS Treatment News Archive* 209.

The mMafA molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a mMafA marker) transcription or expression, the amplified marker may be in a quantity which is more readily detectable than the drug itself. Also, the marker may be more easily detected due to the nature of the marker itself; for example, using the methods described herein, anti-mMafA antibodies may be employed in an immune-based detection system for a mMafA protein marker, or mMafA-specific radiolabeled probes may be used to detect a mMafA mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229-238; Schentag (1999) *Am. J. Health-Syst. Pharm.* 56 Suppl. 3: S21-S24; and Nicolau (1999) *Am, J. Health-Syst. Pharm.* 56 Suppl. 3: S16-S20.

The mMafA molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., mMafA protein or RNA) for specific tumor markers in a subject, a drug or course of treatment may be selected that is optimized for the treatment of the specific tumor likely to be present in the subject. Similarly, the presence or absence of a specific sequence mutation in mMafA DNA may correlate mMafA drug response. The use of pharmacogenomic markers therefore permits the application of the most appropriate treatment for each subject without having to administer the therapy.

Pharmaceutical Compositions

The nucleic acid and polypeptides, fragments thereof, as well as anti-mMafA antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with, e.g., insufficient, aberrant, or unwanted mMafA expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the mMafA molecules of the present invention or mMafA modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted mMafA expression or activity, by administering to the subject a mMafA or an agent which modulates mMafA expression or at least one mMafA activity. Subjects at risk for a disease which is caused or contributed to by aberrant or unwanted mMafA expression or activity can be identified by, for example, any or a combination of diagnostic or prognostic assays as described herein. Administration of a prophylactic agent can occur prior to the manifestation of symptoms characteristic of the mMafA aberrance, such that a disease or disorder is prevented or, alternatively, delayed in its progression. Depending on the type of mMafA aberrance, for example, a mMafA, mMafA agonist or mMafA antagonist agent can be used for treating the subject. The appropriate agent can be determined based on screening assays described herein.

It is possible that some mMafA disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of mMafA disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of mMafA disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, $F(ab')_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by mMafA expression is through the use of aptamer molecules specific for mMafA protein. Aptamers are nucleic acid molecules having a tertiary structure which permits them to specifically bind to protein ligands (see, e.g., Osborne, et al. (1997) Curr. Opin. Chem Biol. 1: 5-9; and Patel, D. J. (1997) Curr Opin Chem Biol 1:32-46). Since nucleic acid molecules may in many cases be more conveniently introduced into target cells than therapeutic protein molecules may be, aptamers offer a method by which mMafA protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of mMafA disorders. For a description of antibodies, see the Antibody section above.

In circumstances wherein injection of an animal or a human subject with a mMafA protein or epitope for stimulating antibody production is harmful to the subject, it is possible to generate an immune response against mMafA through the use of anti-idiotypic antibodies (see, for example, Herlyn, D. (1999) Ann Med 31:66-78; and Bhattacharya-Chattejee, M., and Foon, K. A. (1998) Cancer Treat Res. 94:51-68). If an anti-idiotypic antibody is introduced into a mammal or human subject, it should stimulate the production of anti-anti-idiotypic antibodies, which should be specific to the mMafA protein. Vaccines directed to a disease characterized by mMafA expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889-7893).

The identified compounds that inhibit target gene expression, synthesis and/or activity can be administered to a patient at therapeutically effective doses to prevent, treat or ameliorate mMafA disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography. Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate mMafA activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al (1996) *Current Opinion in Biotechnology* 7:89-94 and in Shea, K. J. (1994) *Trends in Polymer Science* 2:166-173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al (1993) *Nature* 361:645-647. Through the use of isotope-labeling, the "free" concentration of compound which modulates the expression or activity of mMafA can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz, D. et al (1995) *Analytical Chemistry* 67:2142-2144.

Another aspect of the invention pertains to methods of modulating mMafA expression or activity for therapeutic purposes, e.g., for use as therapeutics in β-cell or insulin related disorders, e.g., diabetes (e.g., insulin-dependent diabetes mellitus or non insulin-dependent diabetes mellitus) and its associated disorders, e.g., hypertension and retinopathy, persistent hyperinsulinemic hypoglycaemia of infancy (PHHI), insulin resistance, hyperglycemia, glucose intolerance, glucotoxicity. Accordingly, in an exemplary embodiment, the modulatory method of the invention involves contacting a cell with a mMafA or agent that modulates one or more of the activities of mMafA protein activity associated with the cell. An agent that modulates mMafA protein activity can be an agent as described herein, such as a nucleic acid or a protein, a naturally-occurring target molecule of a mMafA protein (e.g., a mMafA substrate or receptor), a mMafA antibody, a mMafA agonist or antagonist, a peptidomimetic of a mMafA agonist or antagonist, or other small molecule.

In one embodiment, the agent stimulates one or more mMafA activities. Examples of such stimulatory agents include active mMafA protein and a nucleic acid molecule encoding mMafA. In another embodiment, the agent inhibits one or more mMafA activities. Examples of such inhibitory agents include antisense mMafA nucleic acid molecules, anti-mMafA antibodies, and mMafA inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a mMafA protein or nucleic acid molecule. In one embodiment, the method involves administering an agent (e.g., an agent identified by a screening assay described herein), or combination of agents that modulates (e.g., up regulates or down regulates) mMafA expression or activity. In another embodiment, the method involves administering a mMafA protein or nucleic acid molecule as therapy to compensate for reduced, aberrant, or unwanted mMafA expression or activity.

Stimulation of mMafA activity is desirable in situations in which mMafA is abnormally downregulated and/or in which increased mMafA activity is likely to have a beneficial effect. For example, stimulation of mMafA activity is desirable in situations in which a mMafA is downregulated and/or in which increased mMafA activity is likely to have a beneficial effect. Likewise, inhibition of mMafA activity is desirable in situations in which mMafA is abnormally upregulated and/or in which decreased mMafA activity is likely to have a beneficial effect.

Pharmacogenomics

The mMafA molecules of the present invention, as well as agents, or modulators which have a stimulatory or inhibitory effect on mMafA activity (e.g., mMafA gene expression) as identified by a screening assay described herein can be administered to individuals to treat (prophylactically or therapeutically) mMafA associated, e.g., β-cell or insulin related disorder, e.g., diabetes, glucose intolerance or glucotoxicity disorders, associated with aberrant or unwanted mMafA activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a mMafA molecule or mMafA modulator as well as tailoring the dosage and/or therapeutic regimen of treatment with a mMafA molecule or mMafA modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23:983-985 and Linder, M. W. et al. (1997) Clin. Chem. 43:254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach," can be utilized to identify genes that predict drug response. According to this method, if a gene that encodes a drug's target is known (e.g., a mMafA protein of the present invention), all common variants of that gene can be fairly easily identified in the population and it can be determined if having one version of the gene versus another is associated with a particular drug response.

Alternatively, a method termed the "gene expression profiling," can be utilized to identify genes that predict drug response. For example, the gene expression of an animal dosed with a drug (e.g., a mMafA molecule or mMafA modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a mMafA molecule or mMafA modulator, such as a modulator identified by one of the exemplary screening assays described herein.

The present invention further provides methods for identifying new agents, or combinations, that are based on identifying agents that modulate the activity of one or more of the gene products encoded by one or more of the mMafA genes of the present invention, wherein these products may be associated with resistance of the cells to a therapeutic agent. Specifically, the activity of the proteins encoded by the mMafA genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of a mMafA protein can be applied in clinical trials. For example, the effectiveness of an agent determined by a screening assay as described herein to increase mMafA gene expression, protein levels, or upregulate mMafA activity, can be monitored in clinical trials of subjects exhibiting decreased mMafA gene expression, protein levels, or downregulated mMafA activity. Alternatively, the effectiveness of an agent determined by a screening assay to decrease mMafA gene expression, protein levels, or downregulate mMafA activity, can be monitored in clinical trials of subjects exhibiting increased mMafA gene expression, protein levels, or upregulated mMafA activity. In such clinical trials, the expression or activity of a mMafA gene, and preferably, other genes that have been implicated in, for example, a mMafA-associated disorder can be used as a "read out" or markers of the phenotype of a particular cell.

mMafA Informatics

The sequence of a mMafA molecule is provided in a variety of media to facilitate use thereof. A sequence can be provided as a manufacture, other than an isolated nucleic acid or amino acid molecule, which contains a mMafA. Such a manufacture can provide a nucleotide or amino acid sequence, e.g., an open reading frame, in a form which allows examination of the manufacture using means not directly applicable to examining the nucleotide or amino acid sequences, or a subset thereof, as they exists in nature or in purified form. The sequence information can include, but is not limited to, mMafA full-length nucleotide and/or amino acid sequences, partial nucleotide and/or amino acid sequences, polymorphic sequences including single nucleotide polymorphisms (SNPs), epitope sequence, and the like. In a preferred embodiment, the manufacture is a machine-readable medium, e.g., a magnetic, optical, chemical or mechanical information storage device.

As used herein, "machine-readable media" refers to any medium that can be read and accessed directly by a machine, e.g., a digital computer or analogue computer. Non-limiting examples of a computer include a desktop PC, laptop, mainframe, server (e.g., a web server, network server, or server farm), handheld digital assistant, pager, mobile telephone, and the like. The computer can be stand-alone or connected to a communications network, e.g., a local area network (such as a VPN or intranet), a wide area network (e.g., an Extranet or the Internet), or a telephone network (e.g., a wireless, DSL, or ISDN network). Machine-readable media include, but are not limited to: magnetic storage media, such as floppy discs, hard disc storage medium, and magnetic tape; optical storage media such as CD-ROM; electrical storage media such as RAM, ROM, EPROM, EEPROM, flash memory, and the like; and hybrids of these categories such as magnetic/optical storage media.

A variety of data storage structures are available to a skilled artisan for creating a machine-readable medium having recorded thereon a nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

In a preferred embodiment, the sequence information is stored in a relational database (such as Sybase or Oracle). The database can have a first table for storing sequence (nucleic acid and/or amino acid sequence) information. The sequence information can be stored in one field (e.g., a first column) of a table row and an identifier for the sequence can be store in another field (e.g., a second column) of the table row. The database can have a second table, e.g., storing annotations. The second table can have a field for the sequence identifier, a field for a descriptor or annotation text (e.g., the descriptor can refer to a functionality of the sequence, a field for the initial position in the sequence to which the annotation refers, and a field for the ultimate position in the sequence to which the annotation refers. Non-limiting examples for annotation to nucleic acid sequences include polymorphisms (e.g., SNP's) translational regulatory sites and splice junctions. Non-limiting examples for annotations to amino acid sequence include polypeptide domains, e.g., a domain described herein; active sites and other functional amino acids; and modification sites.

By providing the nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif. The search can be a BLAST search or other routine sequence comparison, e.g., a search described herein.

Thus, in one aspect, the invention features a method of analyzing mMafA, e.g., analyzing structure, function, or relatedness to one or more other nucleic acid or amino acid sequences. The method includes: providing a mMafA nucleic acid or amino acid sequence; comparing the mMafA sequence with a second sequence, e.g., one or more preferably a plurality of sequences from a collection of sequences, e.g., a nucleic acid or protein sequence database to thereby analyze mMafA. The method can be performed in a machine, e.g., a computer, or manually by a skilled artisan.

The method can include evaluating the sequence identity between a mMafA sequence and a database sequence. The method can be performed by accessing the database at a second site, e.g., over the Internet.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a mMafA sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features, a method of analyzing a sequence. The method includes: providing a mMafA sequence, or record, in machine-readable form; comparing a second sequence to the mMafA sequence; thereby analyzing a sequence. Comparison can include comparing to sequences for sequence identity or determining if one sequence is included within the other, e.g., determining if the mMafA sequence includes a sequence being compared. In a preferred embodiment the mMafA or second sequence is stored on a first computer, e.g., at a first site and the comparison is performed, read, or recorded on a second computer, e.g., at a second site. E.g., the mMafA or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention provides a machine-readable medium for holding instructions for performing a method for determining whether a subject has a mMafA-associated disease or disorder or a pre-disposition to a mMafA-associated disease or disorder, wherein the method comprises the steps of determining mMafA sequence information associated with the subject and based on the mMafA sequence information, determining whether the subject has a mMafA-associated disease or disorder or a pre-disposition to a mMafA-associated disease or disorder and/or recommending a particular treatment for the disease, disorder or pre-disease condition.

The invention further provides in an electronic system and/or in a network, a method for determining whether a subject has a mMafA-associated disease or disorder or a predisposition to a disease associated with a mMafA wherein the method comprises the steps of determining mMafA sequence information associated with the subject, and based on the mMafA sequence information, determining whether the subject has a mMafA-associated disease or disorder or a pre-disposition to a mMafA-associated disease or disorder, and/or recommending a particular treatment for the disease, disorder or pre-disease condition. In a preferred embodiment, the method further includes the step of receiving information, e.g., phenotypic or genotypic information, associated with the subject and/or acquiring from a network phenotypic information associated with the subject. The information can be stored in a database, e.g., a relational database. In another embodiment, the method further includes accessing the database, e.g., for records relating to other subjects, comparing the mMafA sequence of the subject to the mMafA sequences in the database to thereby determine whether the subject as a mMafA-associated disease or disorder, or a pre-disposition for such.

The present invention also provides in a network, a method for determining whether a subject has a mMafA associated disease or disorder or a pre-disposition to a mMafA-associated disease or disorder associated with mMafA, said method comprising the steps of receiving mMafA sequence information from the subject and/or information related thereto, receiving phenotypic information associated with the subject, acquiring information from the network corresponding to mMafA and/or corresponding to a mMafA-associated disease or disorder (e.g., a β-cell or insulin related disorder, e.g., diabetes, glucose intolerance or glucotoxicity), and based on one or more of the phenotypic information, the mMafA information (e.g., sequence information and/or information related thereto), and the acquired information, determining whether the subject has a mMafA-associated disease or disorder or a pre-disposition to a mMafA-associated disease or disorder. The method may further comprise the step of recommending a particular treatment for the disease, disorder or pre-disease condition.

The present invention also provides a method for determining whether a subject has a mMafA-associated disease or disorder or a pre-disposition to a mMafA-associated disease or disorder, said method comprising the steps of receiving information related to mMafA (e.g., sequence information and/or information related thereto), receiving phenotypic information associated with the subject, acquiring information from the network related to mMafA and/or related to a mMafA-associated disease or disorder, and based on one or more of the phenotypic information, the mMafA information, and the acquired information, determining whether the subject has a mMafA-associated disease or disorder or a pre-disposition to a mMafA-associated disease or disorder. The method may further comprise the step of recommending a particular treatment for the disease, disorder or pre-disease condition.

This invention is further illustrated by the following examples that should not be construed as limiting. The contents of all references, patents and published patent applications cited throughout this application are incorporated herein by reference.

EXAMPLES

Example 1

Cloning of the RIPE3b1 Factor

A two-step purification approach was established to clone the β-cell specific RIPE3b1 activator from hamster insulinoma cell line HIT T-15. As a first step, HIT T-15 nuclear extract was partially purified using HiTrap Heparin column (Pharmacia). Purified fractions containing RIPE3b1 binding activity were pooled into one heparin-pooled fraction (HP). This HP fraction contained about 85% of the recovered RIPE3b 1 factor with a 2.5-fold purification. The RIPE3b binding factor was then affinity purified from the HP fraction using a 5' biotinylated RIPE3b oligonucleotide and streptavidin agarose. The purified fractions were analyzed for binding to a rat insulin II-139 to -101 bp probe by EMSA [FIG. 3, (24)]. The -139 to -101 bp probe contains the RIPE3b and overlapping A2 elements. Five distinct factors (RIPE3b1, RIPE3b2 and three A2 specific complexes) can bind the -139 to -101 bp probe. Thus the -139 to -101 bp probe serves as a good indicator of the purification process. The RIPE3b1 binding activity was eluted in two fractions and was the predominant DNA binding activity in these fractions. RIPE3b1 binding activity was purified 95-fold as compared to the HP fraction and over 200-fol. The purified fraction was next analyzed on a 10% SDS-PAGE gel along with the starting HIT T-15 nuclear extract and HP fraction. Results showed a significant purification after affinity column, although the purified fraction still contained at least 10 bands as detected by silver staining (FIG. 4). The regions corresponding to the individual protein bands were cut; the proteins were then eluted and analyzed for the RIPE3b1 binding activity. One of the eluted proteins (approx. 47-kDa) formed a RIPE3b binding complex with identical electrophoretic mobility and competition profile as the RIPE3b1 complex [FIG. 5, (24)], demonstrating that the 47-kDa protein is highly enriched in the RIPE3b1 factor.

Amino acid sequences of the 47-kDa-protein were determined using HPLC tandem mass spectrometry at Harvard Microchemistry Facility. Results from this analysis identified the chicken transcription factor L-Maf (Gene Bank Accession number AF034570) as sharing identity with five tryptic peptides of the 47-kDa protein. L-Maf was originally cloned from a chicken embryonic lens cDNA library (22) but has also been cloned from quail and termed MafA (23). The transcription factor MafA/L-Maf regulates lens cell-specific expression of crystallin genes and triggers the lens differentiation program. Thus far, no mammalian homologue of MafA/L-Maf has been identified. Maf proteins are subdivided into two classes, "large" (236-370 AA; c-Maf, MafB, NRL and MafA/L-Maf) and "small" (149-162 AA; MafF, MafG and MafK) (22;25;29;30). All "large Maf" proteins have a N-terminal serine/proline/threonine rich acidic activation domain that is absent in the "small Maf" proteins (29;31). However, both "large" and "small Maf" proteins have a high degree of similarity in the C-terminal basic and leucine zipper domains. Although all five tryptic peptides are from the C-terminal domain of MafA, several of the amino acids in these peptides discriminate this factor from the other Maf factors, suggesting that the RIPE3b1 factor is a novel mammalian homologue of MafA (mMafA).

Example 2

Identification of the RIPE3b1 Factor as mMafA

To confirm that RIPE3b1 factor is mMafA, the expression of mMafA was determined in insulin-producing cells and demonstrated that the RIPE3b1 factor can specifically bind a Maf binding site. Furthermore, the endogenous RIPE3b1 complex was recognized by a "large-Maf" specific antibody (FIG. 6). Degenerate oligonucleotides were designed from the amino acid sequences of two tryptic peptides, such that the PCR product would contain the sequence corresponding to the remaining three peptides. Since RIPE3b1 binding activity is only detected in pancreatic β-cells and not α-cells, cDNAs from the insulinoma cell lines HIT T-15 and MIN-6 as well as from a glucagon-producing cell line αTC1.6 were used with degenerate oligonucleotide primers in a PCR reaction. An approximately 300 bp long PCR product was amplified in this reaction from insulin-producing cell lines but not from αTC1.6 cells (FIG. 6A). This PCR product was cloned and sequenced. Then specific internal primers were designed and used in similar PCR reactions, again demonstrating expression of MafA only in insulin-producing cells. The deduced amino acid sequence obtained from the PCR product demonstrated the presence of the expected internal peptides establishing that the avian MafA homologue is selectively expressed in insulin-producing cells.

MafA can bind chicken αA-crystallin Maf element (which is nearly identical to mouse αA-crystallin element), and mutations in this element inhibits DNA binding of MafA and transcriptional activation of αA-crystallin gene (22;25). To demonstrate that the RIPE3b 1 factor can specifically bind the Maf binding site (FIG. 6B), nuclear extract from HIT T-15 cells was incubated with the RIPE3b probe in the absence or presence of wild type or mutant RIPE3b oligonucleotide (24); with wild type or mutant Maf binding oligonucleotides from mouse αA-crystallin gene as cold competitors (22;25). The RIPE3b1 and RIPE3b2 factors can bind rat insulin II oligonucleotides RIPE3b, −139 to −101 bp, −114-113 m, −125-124 m, but not the oligonucleotides −139-113 bp, −110-109 m and −125-124 m (24), and thus showed the expected competition profile (FIG. 6). Importantly, both the RIPE3b1 and RIPE3b2 complexes were successfully competed by the wild type but not by an oligonucleotide containing a single base substitution mutation in the Maf binding site (FIG. 6B). Similar results were obtained in a converse experiment using the Maf binding site from the αA-crystallin gene as a probe. The Maf family of factors recognize the extended DNA element, TGC(N)6-7GCA, (SEQ ID NO: 23) but show a significant variation in DNA binding specificity for individual family members (29;30;32). The RIPE3b element shows modest homology with the MAF binding site of the mouse αA-crystallin gene (CTGN6CAGCC; SEQ ID NO:23) and the MAF consensus sequence (TGCN7GC; SEQ ID NO:24). Conserved GC nucleotides between Maf and RIPE3b element (−118, −117 bp and −109, −108 bp in rat insulin II gene) are important for the binding of RIPE3b1 and RIPE3b2 factors (24). Interestingly, nucleotides upstream of the conserved region (−122 and −122 bp) are also critical for binding of these factors (24). These results show that the RIPE3b element shares a reasonable homology with the consensus MAF binding element and that the RIPE3b1 and RIPE3b2 factors belong to the Maf family of transcription factors.

To confirm that the RIPE3b binding factors belong to the Maf family of transcription factors, DNA binding reactions were preincubated in the presence of anti-c-Maf (that recognizes only the "large Maf" family members), anti-nucleolin and anti-PDX-1 antibodies (FIG. 6C). While, as shown in FIG. 6B, both RIPE3b1 and RIPE3b2 complexes specifically competed with wild-type but not mutant αA-crystallin oligonucleotides, anti-cMaf antibody specifically recognizes only the RIPE3b1 complex and not the RIPE3b2 complex. This result demonstrates that the RIPE3b1 factor is a member of "large Maf" family of transcription factor and that the RIPE3b2 factor is most likely a "small Maf" factor. Of the four large Maf family members, MafB and c-Maf have broad cellular distributions, while NRL and MafA have more restrictive expression (22;25;29;3 1). By RT-PCR, we could detect expression of MafB in pancreatic α- and β-cells and that of c-Maf in α-cells. However, expression of NRL could not be detected in either of the pancreatic cell types (data not shown). mMafA is the only large Maf family member that is selectively expressed in pancreatic β-cells, and amino acid sequencing identifies it as the 47-kDa RIPE3b binding factor. Therefore, RIPE3b1 factor is mMafA.

Figure 7C:
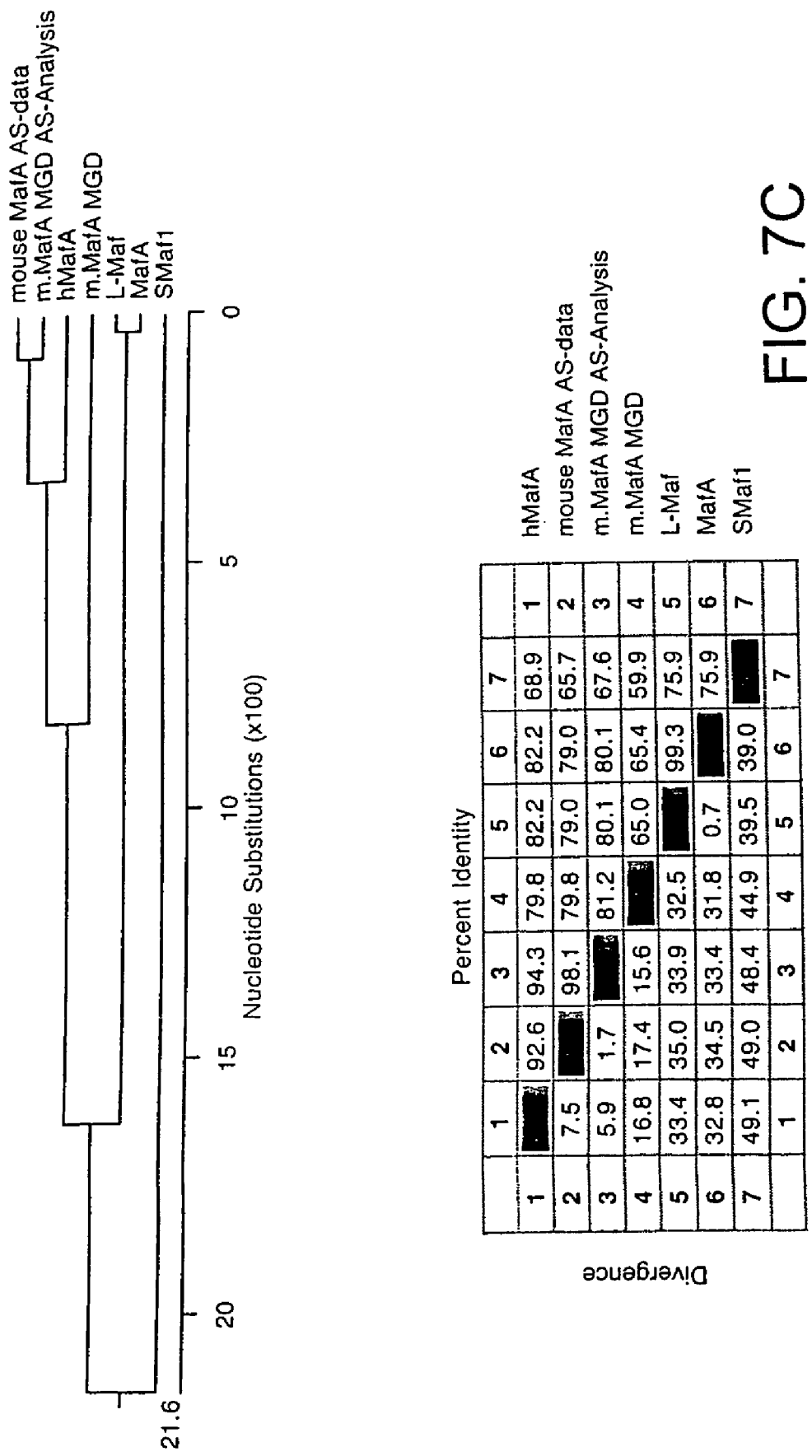

To clone the full-length gene, the nucleotide sequence of the PCR fragment amplified using degenerate oligonucleotide primers was compared with the public human genome database. Results from BLAST analysis showed significant homology to all known Maf genes but the highest homology with a "non-Maf" region of the human genome on chromosome 8q24. Although there was significant sequence homology between human genomic contig and our fragment, annotation of human genome (build 24) did not identify the human mafA (hmafA) gene in this region. Additionally, the publicly available Celera genomic assembly (GA_X54KRCEUARB) contained a gap in the N-terminal region of the hmafA gene. Oligonucleotide primers based on human genome sequence were designed to amplify the sequence around the region of homology, resulting in identification of an intronless ORF (352 amino acid) corresponding to hmafA (FIG. 7). The coding region corresponding to human MafA was PCR amplified using human genomic DNA as a template. The predicted molecular weight of hMafA is approximately 36,850 Da, which is less than the purified protein band (47, 000 Da). The apparent difference may be due to post-translational modification of the hMafA. Quail MafA, a 286 amino acid protein with approximate molecular weight of 32,450 Da, is highly phosphorylated and has multiple isoforms range in size from 35 to 43 kDa (31). Hence, it is quite likely that hMafA (352 amino acids), which is larger than quail MafA, can have an isoform with a molecular weight of 47 kDa. Amino acid sequence alignment of hMafA with other human large and small Maf family members, chicken L-Maf, quail MafA and zebra fish Smaf1 clearly shows that RIPE3b1 factor is more closely related to the chicken and quail protein than to other human Maf factors (FIGS. 7A, B). hMafA is a member of the large Maf family of transcription factor containing an N-terminal activation domain and c-terminal bZIP domain (FIG. 7C). These observations demonstrate that a novel mammalian Maf factor, mMafA, is selectively expressed in insulin-producing cells.

Example 3

Expression of mMafA

Sequence analysis of the human genomic contig NT_023684 using programs FGENESH 1.0 and FGENES-M 1.5 genomic.sanger.ac.uk) indicated the presence of possible transcription start and stop sites, predicting a full-length hMafA mRNA to be approximately 2.7 Kb in size. To demonstrate that the hMafA homologue is expressed in other mammalian systems, approximately 10 μg of total RNA from insulin-producing and non-insulin-producing cells was used in Northern analysis with the N-terminal fragment of the hMafA as a probe. An approximately 2.8 Kb message from insulin-producing cells hybridized with the hMafA probe (FIG. 8B), but no such signal was detected in the lane from glucagon-producing αTC1.6 cells, even though ethidium bromide staining showed equal amounts of RNA (FIG. 8A). To further characterize the expression profile of mMafA, mouse (2 μg poly(A) RNA) multiple tissue Northern blot (Ambion, Austin, Tex.) was hybridized with the same N-terminal hMafA probe (FIG. 8C). RNA from E14 mouse embryo showed two faint bands corresponding to 1.9 and 2.8 Kb transcripts. The presence of 1.9 kb transcript in E14 embryo may result from an alternative transcription start site suggesting a novel regulation of this gene during embryonic development. In addition to expression in E14 embryo, a faint 2.8 Kb band was also seen in RNA from thymus, but no signal was detected from other tissues (heart, brain, liver, spleen, kidney, lung, testes and ovary). Results from this analysis demonstrate that, like its avian counterpart, mMafA has a very restrictive cellular expression profile.

Example 4

Activation of Insulin Expression

The ability of hMafA to bind the RIPE3b element and activate insulin gene expression was confirmed (FIG. 9). Both the full length factor and an N-terminal deletion derivative (ΔN) that lacks the first 138 amino acid and the activation domain (based on comparision with other "large Maf" family members (29) were cloned in frame with HSV.tag in expression vector pETBlue-2. The presence of the tag sequence increases the molecular size of full-length and ΔN constructs (by approximately 3.5 kDa) to 40.4 and 26.8 kDa respectively. In vitro transcribed and translated full-length hMafA (TnT Kit Promega, Madison, Wis.) has an approximate molecular size of 50 kDa, while the ΔN-hMafA protein runs at 28 kDa (FIG. 9B). These observations demonstrate that the expressed mMafA protein is significantly larger than that predicted from the primary amino acid sequence. Furthermore, most of the post-translational modification that alters the molecular size of the protein appears to affect the N-terminal 138 amino acids. These results support our observation that 36.8 kDa mMafA is present as a 47-kDa protein in HIT T-15 nuclear extract.

To determine whether the hMafA can bind the RIPE3b element, rabbit reticulocyte lysates from in vitro translated full-length and ΔN-hMafA constructs were used in EMSA (FIG. 9A). Both full-length and ΔN-hMafA bound the RIPE3b probe with identical DNA binding specificity as the RIPE3b1 factor, and specific DNA binding complexes were recognized by anti HSV.tag antibody. By running the EMSA gel for an extended length of time, we could demonstrate a slight difference in the migration of the full-length DNA binding complex and that of the endogenous RIPE3b1 factor present in HIT T-15 nuclear extract. The difference in the migration of these complexes is possibly due to the presence of the sequence tag. Interestingly, the DNA binding reaction with co-translated hMafA and ΔN-hMafA resulted in formation of three DNA binding complexes: two corresponding to the full-length and ΔN-hMafA, and one with an intermediate migration. Similarly, a combination of translated ΔN-hMafA and HIT T-15 nuclear extract formed RIPE3b binding complexes that migrated between the endogenous RIPE3b1 complex and the faster migrating ΔN-hMafA complex. These results clearly demonstrate that hMafA most likely binds the RIPE3b element as a homo-dimer.

To demonstrate that mMafA can activate insulin gene expression, full-length and ΔN-hMafA constructs were co-transfected with the wild-type (−238 WT LUC) and mutant (122.121 m LUC) insulin promoter:luciferase reporter constructs (24) in non-insulin producing HeLa cells (FIG. 9C). Alone insulin reporters had very low-level expression in HeLa cells, and the mutation in the insulin enhancer at −122.121 bp, which prevents binding of the RIPE3b1 factor, had no effect on the basal luciferase expression. Co-transfection of the full-length hMafA induced luciferase gene expression by several hundred fold over the −238 WT LUC construct alone. However, co-expression of hMafA with the mutant reporter construct activated reporter gene expression by only 15-20% of that of the WT construct. Interestingly, co-expression of ΔN-hMafA did not activate either the WT or mutant constructs. These observations were visually confirmed using an insulin:GFP reporter construct (−410 rINS I:GFP) and immunostaining with anti-HSV.tag antibody to detect expression of the full-length and ΔN-hMafA. Both full-length and ΔN-hMafA proteins are expressed in HeLa cells and have nuclear localization but that only the full-length hMafA construct activated insulin gene expression. These results demonstrate that mMafA can specifically bind the insulin enhancer element RIPE3b and activate expression of insulin gene, thus establishing the mMafA as the insulin gene transcription factor RIPE3b1.

Maf factors play important roles in cell-determination and control of cellular differentiation. The mafB gene is important for the segmentation of the hindbrain (33) and contributes to monoblast and macrophage differentiation (34). The transcription factor c-Maf has been implicated in lymphopoiesis and lens development (35;36). Expression of NRL (mouse) and MafA/L-Maf (quail/chicken) is crucial for lens development (22;25;31). Our demonstration of the insulin gene transcription factor RIPE3b1 as the mMafA is the first report for a role for Maf family of transcription factors in regulating pancreatic β-cell function. Based on the important developmental role of the avian MafA factor, we suggest that mMafA (RIPE3b1) will regulate the development and differentiation of pancreatic β-cells. In addition, earlier results showed that the RIPE3b1 factor regulates β-cell specific and glucose-responsive expression of insulin, thus cloning of the RIPE3b1/mMafA should lead to better understanding of β-cell function during the development of diabetes.

The human mMafA cDNA sequence is shown in FIG. 1 (SEQ ID NO:1). The initiation codon (ATG) is underlined. The coding sequence encodes a 352 amino acid protein which is shown as SEQ ID NO:2 (FIG. 2).

The mouse mMafA coding sequence is shown as SEQ ID NO:5 (FIG. 12A), and the corresponding protein sequence as SEQ ID NO:6 (FIG. 7A).

Example 5 mMafA Assays mMafA activity, e.g., DNA binding activity or transactivation activity, can be assayed by any of several methods known in the art. An exemplary assay is antibody super-shift analysis, in which an anti-mMafA antibody can recognize mMafA present in a mMafA-DNA complex or a mMafA-bZip protein complex and super-shift or inhibit the formation of the complex. EMSA analysis can also be used to detect complexes of mMafA and mMAfA binding partners, e.g., other mMafA molecules, other bZip proteins or DNA. In another approach, commercial in vitro transcription-translation kits (e.g., TnT kit, Promega) can be used. mMafA is synthesized from an mMafA encoding DNA and incubated with a labeled RIPE3b probe, and binding activity is analyzed by EMSA.

Example 6

Materials and Methods

Electrophoretic Mobility Shift Assays:

Wild type and the mutant rat insulin II oligonucleotides used in the study have been described before (24). The RIPE3b1 and RIPE3b2 factors can bind rat insulin II oligonucleotides RIPE3b, −139 to −101 bp, −114-113 m, −125-124 m, but not the oligonucleotides −139-113 bp, −110-109 m and −125-124 m (24). Other oligonucleotides used in the EMSA are wild type (5' ACGTAGCATTCCAGCTGCT-GACGGTGCAGCCTCTCCCCCGAG 3'), or mutant αA-Crystallin (5' ACGTAGCATTCCAGCTGCTGCCGGT-GCAGCCTCTCCCCCGAG 3') (25). Competition experiments were performed by simultaneous addition of radiolabelled probe and 50-fold excess unlabelled competitors to the binding reaction. For antibody super-shift experiments, antibodies were preincubated with the nuclear extract for 20 min at room temperature, followed by another 20-min incubation in the presence of the radiolabelled probe and analysis by EMSA. Dr. Joel Habener generously provided the anti-IDX-1 (PDX-1) antibody, while anti-cMaf and anti-nucleolin antibodies were from Santa Cruz Biotechnology (Santa Cruz, Calif.).

Purification of the RIPE3b1

For large-scale purification, 20 ml of nuclear extract (26) (about 90 mg total protein containing at least 100 pmol of the RIPE3b 1 factor) from hamster insulinoma cell line HIT T15 was loaded onto HiTrap Heparin column (Pharmacia, Piscataway, N.J.), and fractions were eluted with binding buffer containing increasing amounts of salt. Fractions containing the RIPE3b1 binding activity were pooled into one heparin-pooled (HP) fraction. For affinity purification, annealed 5' biotinylated (top strand) RIPE3b (−126 to −101 bp) dimer oligonucleotide (5' TGA CTG GAA ACT GCA GCT TCA GCC CCT CTG GAA ACT GCA GCT TCA GCC CCA C 3';SEQ ID NO:14) was incubated for 1 h with the HP fraction followed by addition of three ml of streptavidin agarose (Pierce, Rockford, Ill.). The mixture was packed into a column and washed with RIPE3b1 buffer containing increasing concentration of salt. Proteins present in the affinity-purified fractions were concentrated using the Orgosol protein concentration kit (GenoTech, St. Louis, Mo.). The concentrated fraction was run on a 10% SDS-PAGE gel and protein bands were detected using Silver stain kit (BioRad, Hercules, Calif.).

To identify that the protein band contained the RIPE3b1 factor, SDS-PAGE fractionation was performed (27). An unheated purified fraction was run in duplicate on a 10 %/SDS-PAGE gel. The gel was allowed to renature for 30 min and was then transferred onto a PVDF membrane. The membrane was cut into two, and one half was stained with Colloidal Gold Stain (BioRad, Hercules, Calif.) the protein bands were cut from the other half and proteins were eluted in a buffer containing Triton X-100.

Concentrated purified protein fractions were run on a SDS-PAGE gel, and the 47-kDa protein band (approximately 45 pmol) was cut. In gel reduction, alkylation and trypsin digestion were performed. Approximately 10% of the digested sample was used to determine the amino acid sequence of the tryptic peptides by microcapillary reverse-phase HPLC nano-electrospray tandem mass spectrometry (µLC/MS/MS) with a Finnigan LCQ quadrupole ion trap mass spectrometer at Harvard Microchemistry Facility.

Cloning of the Human MafA:

Degenerate oligonucleotide primers corresponding to peptide sequences, SDDQLV (SEQ ID NO:15) (WSIGAYGAY-CARYTIGTIWS; SEQ ID NO:16) and LYKEKY (SEQ IID NO:17) (TCRTAYTTYTCYTTRTAIAR; SEQ ID NO:18), of the 47-kDa protein were used in a RT-PCR reaction with cDNAs from insulin-producing (HIT T-l 5 and MTN-6) and glucagon-producing (αTC 1.6) cell lines. PCR product from HIT T- 15 cDNA was isolated, cloned, sequenced and used to design specific internal oligonucleotide primers (5' primer GATGTCGGTGCGGGAGCTGAACC (SEQ ID NO:19) and 3' primer CCCACCTCCAGCTTCAGCTGCTC (SEQ ID NO:20); cyclophilin primers have been described (28). To clone the complete coding region of human MafA, genomic DNA (Clontech, Palo Alto. CA) was used as a template with the 5'primer (ATGGCCGCGGAGCTGGCGATG SEQ ID NO:21) and 3 ' primer (CAGGAAGAAGTCGGCCGTGC-CCT; SEQ ID NO:22) in a PCR reaction.

Northern Analysis:

Approximately 10 µg of total RNA from mouse islets, insulin-producing (MIN6 and HIT-T15) and non-insulin-producing αTC1.6 cell lines were used for Northern blot analysis. N-terminal fragment (1-473 bp) of human MafA was labeled using Strip-EZ kit (Ambion, Austin, Tex.) for Northern analysis.

Determination of Insulin Gene Expression:

HeLa cells were transfected with 2 µg of luciferase reporter plasmid (−238 WT LUC or −122.121 m LUC) (24), 0.5 µg of pcDNA3.1 vector or full-length hMafA or an N-terminal deletion derivative of hMafA lacking first 138 amino acids (ΔN-hMafA) cloned into pcDNA3.1, and 0.5 µg of pSV-β-galactosidase plasmid (Promega, Madison, Wis.). Luciferase and β-galactosidase activities were determined 48 h after transfection. For immunostaining HeLa cells were transfected with 1 µg of rat insulin I:GFP reporter (−410 rINSI: GFP) and 1.5 µg of hMafA, ΔN-hMafA or pcDNA3.1 expression plasmids. 48 h after transfection, HeLa cells were fixed with 10% buffered formalin, and fusion proteins were detected using αHSV.tag monoclonal antibody and a secondary Texas Red conjugated anti mouse antibody.

REFERENCES

1. Boam, D. S. W. & Docherty, K. (1989) *Biochem. J.* 264, 233-239.
2. Shieh, S. -Y. & Tsai, M. -J. (1991) *J. Biol. Chem.* 266, 16708-16714.
3. Sharma, A. & Stein, R. (1994) *Mol Cell Biol* 14,871-879.
4. Karisson, O., Edlund, T., Barnett Moss, J., Rutter, W. J., & Walker, M. D. (1987) *Proc. Natl. Acad. Sci. USA* 84, 8819.
5. Crowe, D. T. & Tsai, M. -J. (1989) *Mol. Cell Biol.* 9, 1784-1789.
6. Ohlsson, H., Karlsson, K., & Edlund, T. (1993) *EMBO J.* 12, 4251-4259.
7. Leonard, J., Peers, B., Johnson, T., Ferreri, K., Lee, S., & Montminy, M. R. (1993) *Mol. Endocrinology* 1275-1283.
8. Miller, C. P., McGehee, R. E., & Habener, J. F. (1994) *EMBO J.* 13, 1145-1156.
9. Jonsson, J., Carlsson, L., Edlund, T., & Edlund, H. (1994) *Nature* 371, 606-609.

10. Offield, M. F., Jetton, T. L., Labosky, P., Ray, M., Stein, R., Magnuson, M., Hogan, B. L. M., & Wright, C. V. E. (1996) *Development* 122, 983-985.
11. Lee, J. E., Hollenberg, S. M., Snider, L., Turner, D. L., Lipnick, N., & Weintraub, H. (1995) *Science* 268, 836.
12. Naya, F. J., Stellrecbt, C. M. M., & Tsai, M. -J. (1995) *Genes Dev.* 9, 1009-1019.
13. Naya, F. J., Huang, H. P., Qiu, Y., Mutoh, H., DeMayo, F. J., Leiter, A. B., & Tsai, M. J. (1997) *Genes Dev* 11, 2323-2334.
14. Ahlgren, U., Jonsson, J., & Edlund, H. (1996) *Development* 122, 1409-1416.
15. Shieh, S. Y., Stellrecht, C. M. M., & Tsai, M. J. (1995) *J. Biol. Chem.* 270, 21503-21508.
16. Zhao, L., Cissell, M. A., Henderson, E., Colbran, R., & Stein, R. (2000) *J. Biol. Chem.* 275, 10532-10537.
17. MacFarlane, W. M., Read, M. L., Gilligan, M., Bujalska, I., & Docherty, K. (1994) *Biochem. J.* 303, 625-631.
18. Melloul, D., Ben-Neriah, Y., & Cerasi, E. (1993) *Proc. Natl. Acad. Sci. USA* 90, 3865-3869.
19. German, M. S. & Wang, J. (1994) *Mol. Cell. Biol.* 14, 4067-4075.
20. Sharma, A., Olson, L. K., Robertson, R. P., & Stein, R. (1995) *Mol. Endocrinology* 9, 1127-1134.
21. Olson, L. K., Sharma, A., Peshavaria, M., Wright, C. V. E., Towle, H. C., Robertson, R. P., & Stein, R. (1995) *Proc. Natl. Acad. Sci. USA* 92, 9127-9131.
22. Ogino, H. & Yasuda, K. (1998) *Science* 280, 115-118.
23. Benkhelifa, S., Provot, S., Lecoq, O., Pouponnot, C., Calothy, G., & Felder-Schmittbuhl, M. P. (1998) *Oncogene* 17, 247-254.
24. Harrington, R. H. & Sharma, A. (2001) *J. Biol. Chem.* 276, 104-113.
25. Ring, B. Z., Cordes, S. P., Overbeek, P. A., & Barsh, G. S. (2000) *Development* 127, 307-317.
26. Dignam, J. D., Lebovitz, R. M., & Roeder, R. G. (1983) *Nucleic Acids Res.* 11, 1475-1489.
27. Silva, C. M., Tully, D. B., Petch, L. A., & Jewell, C. M. (1987) *Proc. Natl. Acad. Sci. USA* 84, 1744-1748.
28. Jonas, J. -C., Sharma, A., Hasenkamp, W., Ilkova, H., Patane, G., Laybutt, R., Bonner-Weir, S., & Weir, G. C. (1999) *J. Biol. Chem.* 274, 14112-14121.
29. Blank, V. & Andrews, N.C. (1997) *TIBS* 22, 437-441.
30. Matsushima-Hibiya, Y., Nishi, S., & Sakai, M. (1998) *Biochem. Biophys. Res. Com.* 245, 412-418.
31. Benkhelifa, S., Provot, S., Nabais, E., Eychene, A., Calothy, G., & Felder-Schmittbuhl, M. -P. (2001) *Mol. Cell. Biol.* 21, 4441-4452.
32. Dlakic, M., Grinberg, A. V., Leonard, D. A., & Kerppola, T. K. (2001) *EMBO J.* 20, 828-840.
33. Manzanares, M., Cordes, S., Kwan, C. -T., Sham, M. H., Barsh, G. S., & Krumlauf, R. (1997) *Nature* 387, 191-195.
34. Sieweke, M. H., Tekotte, H., Frampton, J., & Graf, T. (1996) *Cell* 85, 49-60.
35. Kim, J. I., Li, T., Ho, I. -C., Grusby, M. J., & Glimcher, L. H. (1999) *Proc. Natl. Acad. Sci. USA* 96, 3781-3785.
36. Ho, I. C., Hodge, M. R., Rooney, J. W., & Glimcher, L. H. (1996) *Cell* 85, 973-983.
37. Huang, H. P., M. Liu, H. M. El-Hodiri, K. Chu, M. Jamrich, and M. J. Tsai. 2000. Regulation of the pancreatic islet-specific gene BETA2 (neuroD) by neurogenin 3. Mol. Cell.Biol. 20:3292-3307.
38. Crowe, D. T. and M. -J. Tsai. 1989. Mutagenesis of the rat insulin II 5'-flanking region defines sequences important for expression in HIT cells. Mol. Cell. Biol. 9:1784-1789.
39. Samaras, S. E., M. A. Cissell, K. Gerrish, C. V. Wright, M. Gannon, and R. Stein. 2002. Conserved sequences in a tissue-specific regulatory region of the pdx-1 gene mediate transcription in Pancreatic beta cells: role for hepatocyte nuclear factor 3 beta and Pax6. Mol Cell Biol 22:4702-4713.
40. Gerrish, K., M. Gannon, D. Shih, E. Henderson, M. Stoffel, C. V. Wright, and R. Stein. 2000. Pancreatic beta cell-specific transcription of the pdx-1 gene. The role of conserved upstream control regions and their hepatic nuclear factor 3beta sites. J Biol Chem 275:3485-3492.
41. Wu, K. L., M. Gannon, M. Peshavaria, M. F. Offield, E. Henderson, M. Ray, A. Marks, L. W. Gamer, C. V. Wright, and R. Stein. 1997. Hepatocyte nuclear factor 3beta is involved in pancreatic beta-cell-specific transcription of the pdx-1 gene. Mol Cell Biol 17:6002-6013.
42. Marshak, S., E. Benshushan, M. Shoshkes, L. Havin, E. Cerasi, and D. Melloul. 2000. Functional conservation of regulatory elements in the pdx-1 gene: PDX-1 and hepatocyte nuclear factor 3beta transcription factors mediate beta-cell-specific expression. Mol Cell Biol 20:7583-7590.
43. Gerrish, K., M. A. Cissell, and R. Stein. 2001. The role of hepatic nuclear factor 1 alpha and PDX-1 in transcriptional regulation of the pdx-1 gene. J Biol Chem 276 :47775-47784.
44. Marshak, S., E. Ben-Shushan, M. Shoshkes, L. Havin, E. Cerasi, and D. Melloul. 2001. Regulatory elements involved in human pdx-1 gene expression. Diabetes 50 Suppl 1:S37-38.
45. Sharma, S., U. S. Jhala, T. Johnson, K. Ferreri, J. Leonard, and M. Montminy. 1997. Hormonal regulation of an islet-specific enhancer in the pancreatic homeobox gene STF-1. Mol Cell Biol 17:2598-2604.
46. Ben-Shushan, E., S. Marshak, M. Shoshkes, E. Cerasi, and D. Melloul. 2001. A pancreatic beta -cell-specific enhancer in the human PDX-1 gene is regulated by hepatocyte nuclear factor 3beta (HNF-3beta), HNF-1alpha, and SPs transcription factors. J Biol Chem 276:17533-17540.
47. Sharma, S., J. Leonard, S. Lee, H. D. Chapman, E. H. Leiter, and M. R. Montminy. 1996. Pancreatic islet expression of the homeobox factor STF-1 relies on an E-box motif that binds USF. J Biol Chem 271:2294-2299.
48. Carty, M. D., J. S. Lillquist, M. Peshavaria, R. Stein, and W. C. Soeller. 1997. Identification of cis- and trans-active factors regulating human islet amyloid polypeptide gene expression in pancreatic beta-cells. J Biol Chem 272: 11986-11993.
49. Gannon, M., L. W. Gamer, and C. V. Wright. 2001. Regulatory regions driving developmental and tissue-specific expression of the essential pancreatic gene pdxl. Dev Biol 238:185-201.
50. Watada, H., R. G. Mirmira, J. Leung, and M. S. German. 2000. Transcriptional and translational regulation of beta-cell differentiation factor Nkx6.1. J Biol Chem 275:34224-34230.
51. Karlsson et al. 1987. A mutational analysis of the insulin gene transcription control region: expression in beta cells is dependent on two related sequences within the enhancer. PNAS USA 84:8819-8823.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method of providing a human insulin-producing cell, the method comprising:
providing an isolated human cell comprising an insulin gene; and
inducing the expression in said cell of a Maf polypeptide comprising a DNA binding domain that is at least 95% identical to amino acids 227-281 of SEQ ID NO:2, wherein the Maf polypeptide increases transcription of the insulin gene,
wherein the cell also expresses one or both of PDX-1 and BETA2, thereby providing a human insulin-producing cell.

2. The method of claim 1, wherein the cell is selected from the group consisting of stem cells, pancreatic ductal cells, pancreatic acinar cells, pancreatic endocrine cells, enteroendocrine cells, and hepatic cells.

3. The method of claim 2, wherein the stem cell is an adult or embryonic stem cell.

4. The method of claim 2, wherein the stem cell is pluripotent, multipotent, or totipotent.

5. The method of claim 2, wherein the stem cell expresses an endodermal marker.

6. The method of claim 1, wherein the cell is a pancreatic β-cell.

7. The method of claim 1, wherein the cell is a pancreatic precursor cell.

8. The method of claim 1, wherein the cell is a dedifferentiated duct or exocrine cell.

9. The method of claim 1, wherein the cell is from a cell line.

10. The method of claim 1, wherein the Maf polypeptide comprises an amino acid sequence that is at least 95% identical to SEQ ID NO: 2.

11. The method of claim 1, wherein the Maf polypeptide comprises SEQ ID NO: 2.

12. The method of claim 1, wherein the Maf polypeptide consists of SEQ ID NO: 2.

13. The method of claim 1, further comprising the step of inducing the expression of one or more of PDX-1, E2A, HEB or BETA2 in the cell.

14. A method of providing an insulin-producing cell, the method comprising:
providing an isolated mammalian cell comprising an insulin gene, wherein the cell is selected from the group consisting of stem cells, pancreatic ductal cells, pancreatic acinar cells, pancreatic endocrine cells, enteroendocrine cells, and hepatic cells; and
transfecting the cell with a nucleic acid encoding a Maf polypeptide comprising a DNA binding domain that is at least 95% identical to amino acids 227-281 of SEQ ID NO: 2 wherein the polypeptide increases transcription of the insulin gene, in an amount sufficient to increase insulin expression in the cell, thereby providing an insulin-producing cell.

15. The method of claim 14, wherein the cell is transiently transfected.

16. The method of claim 14, wherein the cell is stably transfected.

17. The method of claim 14, wherein the cell is transfected with a nucleic acid encoding a full length Maf protein that is at least 95% identical to SEQ ID NO:2.

18. The method of claim 14, wherein the cell is transfected with a nucleic acid encoding a Maf fusion protein, wherein the fusion protein has the ability to increase transcription of a responsive gene.

19. The method of claim 18, wherein the fusion protein comprises a DNA binding domain from a Maf protein, and a transcriptional activation domain from another transcription factor.

20. The method of claim 19, wherein the transcriptional activation domain is from simplex virus transcriptional regulatory protein (VP16).

21. The method of claim 14, wherein the stem cell is an adult or embryonic stem cell.

22. The method of claim 14, wherein the stem cell is pluripotent, multipotent, or totipotent.

23. The method of claim 14, wherein the stem cell expresses an endodermal marker.

24. The method of claim 14, wherein the cell is a pancreatic β-cell.

25. The method of claim 14, wherein the cell is a pancreatic precursor cell.

26. The method of claim 14, wherein the cell is a dedifferentiated duct or exocrine cell.

27. The method of claim 14, further comprising the step of inducing the expression of one or more of PDX-1, E2A, HEB or BETA2 in the cell.

28. The method of claim 1, wherein the cell is an insulin producing cell or a cell with potential to differentiate into an insulin producing cell.

29. The method of claim 14, wherein the mammalian cell is a mammalian insulin producing cell or a mammalian cell with potential to differentiate into an insulin producing cell.

30. The method of claim 14, wherein the Maf DNA binding domain is at least 99% identical to amino acids 227-281 of SEQ ID NO: 2.

31. The method of claim 14, wherein the Maf DNA binding domain comprises amino acids 227-281 of SEQ ID NO: 2.

32. A method of providing an insulin-producing cell, the method comprising:

providing an isolated mammalian cell comprising an insulin gene;

transfecting the cell with a nucleic acid encoding a Maf polypeptide comprising a DNA binding domain that is at least 95% identical to amino acids 227-281 of SEQ ID NO: 2, wherein the polypeptide can increase transcription of the insulin gene, in an amount sufficient to increase insulin expression in the cell; and assaying insulin production in the cell; thereby providing an insulin-producing cell.

33. The method of claim 32, wherein the Maf is at least 95% identical to SEQ ID NO: 2.

34. The method of claim 32, wherein the Maf polypeptide comprises SEQ ID NO: 2.

35. The method of claim 32, wherein the Maf DNA binding domain is at least 99% identical to amino acids 227-281 of SEQ ID NO: 2.

36. The method of claim 32, wherein the Maf DNA binding domain comprises amino acids 227-281 of SEQ ID NO: 2.

37. The method of claim 32, wherein the Maf DNA binding domain consists of amino acids 227-281 of SEQ ID NO: 2.

38. The method of claim 32, wherein the mammalian cell is a mammalian insulin producing cell or a mammalian cell with potential to differentiate into an insulin producing cell.

39. The method of claim 32, further comprising transfecting the cell with a nucleic acid encoding one or more of PDX-1, E2A, HEB or BETA2.

40. A method of increasing transcription of insulin in a mammalian cell, the method comprising:

selecting a vector on the basis that it comprises a nucleic acid encoding a polypeptide sequence that is at least 95% identical to SEQ ID NO: 2 operably linked to a regulatory region, wherein the encoded polypeptide can increase transcription of an endogenous insulin gene in the cell; and transfecting an isolated mammalian cell with the vector, thereby increasing transcription of insulin in the cell.

41. The method of claim 40, further comprising assaying insulin production in the cell.

42. The method of claim 40, wherein the mammalian cell is a mammalian insulin producing cell or a mammalian cell with potential to differentiate into an insulin producing cell.

43. The method of claim 40, wherein the mammalian cell is a human cell.

44. The method of claim 1, wherein the method comprises transfecting a population of cells with a purified preparation of the vector.

45. The method of claim 1, wherein the cell expresses both of PDX-1 and Beta-2.

46. The method of claim 14, wherein the cell expresses one or both of PDX-1 or Beta-2.

47. The method of claim 32, further comprising transfecting the cell with one or both of a nucleic acid encoding PDX-1 or a nucleic acid encoding Beta-2.

48. The method of claim 40, wherein the cell expresses one or both of PDX-1 and Beta-2.

49. The method of claim 40, further comprising transfecting the cell with one or both of a nucleic acid encoding PDX-1 or a nucleic acid encoding Beta-2.

* * * * *